United States Patent
Doherty et al.

(10) Patent No.: US 6,277,824 B1
(45) Date of Patent: Aug. 21, 2001

(54) COMPOUNDS AND METHODS FOR MODULATING ADHESION MOLECULE FUNCTION

(75) Inventors: Patrick Doherty, Twickenham (GB); Orest W. Blaschuk, Westmount; Barbara J. Gour, Montreal, both of (CA)

(73) Assignee: Adherex Technologies, Ottawa (CA)

( * ) Notice: Subject to any disclaimer, the term of this patent is extended or adjusted under 35 U.S.C. 154(b) by 0 days.

(21) Appl. No.: 09/113,977

(22) Filed: Jul. 10, 1998

(51) Int. Cl.[7] .............................. A61K 38/00; C07K 17/00
(52) U.S. Cl. ................................ 514/13; 514/14; 514/15; 514/16; 514/17; 530/326; 530/327; 530/328; 530/329; 530/345; 530/350; 530/402
(58) Field of Search .................................. 530/387.9, 300, 530/326, 327, 328, 329, 388.22, 391.1, 391.3, 391.7, 402, 345, 350; 536/23.5; 424/139.1, 143.1; 514/2, 13–17

(56) References Cited

U.S. PATENT DOCUMENTS

| | | |
|---|---|---|
| 5,231,082 | 7/1993 | Schasteen . |
| 5,300,630 * | 4/1994 | Matsura et al. ...................... 530/329 |
| 5,352,667 | 10/1994 | Lider et al. . |
| 5,510,628 | 4/1996 | Georger, Jr. et al. . |
| 5,585,351 | 12/1996 | Ranscht . |
| 5,591,432 | 1/1997 | Bronson et al. . |
| 5,643,781 * | 7/1997 | Suzuki ............................... 435/69.1 |
| 5,646,250 | 7/1997 | Suzuki . |
| 5,665,590 | 9/1997 | Yang . |
| 5,708,143 * | 1/1998 | Suzuki ............................... 530/350 |
| 5,854,044 * | 12/1998 | Pasten et al. ........................ 435/194 |
| 5,863,804 * | 1/1999 | Ranscht ............................. 436/547 |
| 5,900,404 * | 5/1999 | Gegg et al. ........................... 514/12 |

FOREIGN PATENT DOCUMENTS

| | | |
|---|---|---|
| 0410539A1 * | 1/1991 | (EP) . |
| 411 503 A1 | 2/1991 | (EP) . |
| 406 428 B1 | 3/1995 | (EP) . |
| 8-151396 | 6/1996 | (JP) . |
| WO 89/05150 * | 6/1989 | (WO) . |
| WO 90/11297 * | 10/1990 | (WO) . |
| WO 91/04745 | 4/1991 | (WO) . |
| WO 92/08731 | 5/1992 | (WO) . |
| WO 94/11401 | 5/1994 | (WO) . |
| WO 96/40781 | 12/1996 | (WO) . |
| WO 97/07209 | 2/1997 | (WO) . |
| WO 98/02452 | 1/1998 | (WO) . |
| WO 98/45319 | 10/1998 | (WO) . |

OTHER PUBLICATIONS

Tanihara et al., "Cloning of Five Human Cadherins Clarifies Characteristic Features of Cadherin Extracellular Domain and Provides Further Evidence for Two Structurally Different Types of Cadherin," *Cell Adhesion and Communication* 2: 15–26, 1994.

Horn et al. Geneseq. Acc. #P91888, Jan. 1991.*
Hodgson et al. Geneseq. Acc. #W22709, Sep. 1997.*
Reid. PIR Acc. #A38870, Jun. 1993.*
Liaw et al. PIR Acc. #S11693, Jun. 1993.*
Hatta et al. PIR Acc. #A29964, Jun. 1993.*
Ginsberg et al. PIR Acc. #A43785, Jun. 1993.*
Blaschuk et al., "Identification of a Conserved Region Common to Cadherins and Influenza Strain A Hemagglutinins," *J. Mol. Biol.* 211: 679–682, 1990.
Blaschuk et al., "Identification of a Cadherin Cell Adhesion Recognition Sequence," *Developmental Biology* 139: 227–229, 1990.
Lutz et al., "Secondary Structure of the HAV Peptide Which Regulates Cadherin–Cadherin Interaction," *Journal of Biomolecular Structure & Dynamics* 13(3): 447–455, 1995.
Munro et al. *Cell Adhesion and Invasion in Cancer Metastasis*, R.G. Landes Company, Austin, TX, 1996, Chapter 3, "The Structure, Function and Regulation of Cadherins," pp. 17–34.
Newton et al., "N–Cadherin Mediates Sertoli Cell–Spermatogenic Cell Adhesion," *Developmental Dynamics* 197: 1–13, 1993.
Overduin et al., "Solution Structure of the Epithelial Cadherin Domain Responsible for Selective Cell Adhesion," *Science* 267: 386–389, 1995.
Redies et al . "Cadherins in the Developing Central Nervous System: An Adhesive Code for Segmental and Functional Subdivisions," *Developmental Biology* 180: 413–423, 1996.
Willems et al., "Cadherin–dependent cell aggregation is affected by decapeptide derived from rat extracellular super–oxide dismutase," *FEBS Letters* 363: 289–292, 1995.
Shapiro et al., "Structural basis of cell–cell adhesion by cadherins," *Nature* 374: 327–337, 1995.
Alexander et al., "An N–Cadherin–Like Protein Contributes to Solute Barrier Maintenance in Cultured Endothelium," *Journal of Cellular Physiology* 156: 610–618, 1993.
Ali et al., "Conformationally Constrained Peptides and Semipeptides Derived from RGD as Potent Inhibitors of the Platelet Fibrinogen Receptor and Platelet Aggregation," *J. Med. Chem.* 37(6): 769–780, 1994.
Blaschuk et al. "Estradiol Stimulates Cadherin Expression in Rat Granulosa Cells," *Developmental Biology* 136: 564–567, 1989.

(List continued on next page.)

*Primary Examiner*—Christina Y. Chan
*Assistant Examiner*—Marianne DiBrino
(74) *Attorney, Agent, or Firm*—Seed IP Law Group PLLC

(57) ABSTRACT

Modulating agents and methods for enhancing or inhibiting cadherin-mediated functions are provided. The modulating agents comprise at least an HAV binding motif, an analogue or peptidomimetic thereof, or an antibody or fragment thereof that specifically binds to such a motif. Modulating agents may additionally comprise one or more cell adhesion recognition sequences recognized by cadherins and/or other adhesion molecules. Such modulating agents may, but need not, be linked to a targeting agent, drug and/or support material.

11 Claims, 11 Drawing Sheets

OTHER PUBLICATIONS

Byers et al., "Fibroblast Growth Factor Receptors Contain a Conserved HAV Region Common to Cadherins and Influenza Strain A Hemagglutinins: A Role in Protein–Protein Interactions?," *Developmental Biology 152*: 411–414, 1992.

Craig et al., "Concept and Progress in the Development of RGD–Containing Peptide Pharmaceuticals," *Biopolymers (Peptide Science) 37*: 157–175, 1995.

Letourneau et al., "Interactions of Schwann Cells with Neurites and with Other Schwann Cells Involve the Calcium–dependant Adhesion Molecule, N–cadherin," *Journal of Neurobiology 22*(7): 707–720, 1991.

Samanen et al., "Development of a Small RGD Peptide Fibrinogen Receptor Antagonist with Potent Antiaggregatory Activity in Vitro," *J. Med. Chem. 34*(10): 3114–3125, 1991.

Cardarelli et al., "The Collagen Receptor α2β1, from MG–63 and HT1080 Cells, Interacts with a Cyclic RGD Peptide," *The Journal of Biological Chemistry 267*(32): 23159–23164, 1992.

Cepek et al., "Expression of a candidate cadherin in T lymphocytes," *Proc. Natl. Acad. Sci. USA 93*: 6567–6571, 1996.

Doherty and Walsh, "Signal transduction events underlying neurite outgrowth stimulated by cell adhesion molecules," *Current Opinion in Neurobiology 4*: 49–55, 1994.

Laird et al., "Gap Junction Turnover, Intracellular Trafficking, and Phosphorylation of Connexin43 in Brefeldin A–treated Rat Mammary Tumor Cells," *The Journal of Cell Biology 131*(5): 1193–1203, 1995.

Lee et al., "Expression of the Homotypic Adhesion Molecule E–Cadherin by Immature Murine Thymocytes and Thymic Epithelial Cells," *Journal of Immunology 152*: 5653–5659, 1994.

Moran, "The Protein Delivery Service. Advances in technologies for delivering proteins and peptides in therapeutically useful forms," *Pharmaceutical Forum Issue 6*: 4–7, 1996.

Munro et al., "Characterization of Cadherins Expressed by Murine Thymocytes," *Cellular Immunology 169* 309–312, 1996.

Tsutsui et al., "Expression of Cadherin–Catenin Complexes in Human Leukemia Cell Lines," *J. Biochem. 120*: 1034–1039, 1996.

Wickelgren,I."Breaking the Skin Barrier," *PS 12*: 86–88, 1996.

Williams et al., "Activation of the FGF Receptor Underlies Neurite Outgrowth Stimulated by L1, N–CAM, and N–Cadherin," *Neuron 13*: 583–594, 1994.

Blakemore, "Remyelination of CNS axons by Schwann cells transplanted from the sciatic nerve," *Nature 266*: 68–69, 1977.

Bottenstein and Sato, "Growth of a rat neuroblastoma cell line in serum–free supplemented medium," *Proc.Natl. Acad. Sci. USA 76*(1): 514–517, 1979.

Brecknell et al., "Bridge grafts of Fibroblast Growth Factor–4–Secreting Schwannoma Cells Promote Functional Axonal Regeneration in the Nigrostriatal Pathway of the Adult Rat," *Neuroscience 74*(3): 775–784, 1996.

Brockes et al., "Studies on Cultured Rat Schwann Cells. I. Establishment of Purified Populations from Cultures of Peripheral Nerve," *Brain Research 165*: 105–118, 1979.

Brook et al., "Morphology and Migration of Cultured Schwann Cells Transplanted Into the Fimbria and Hippocampus in Adult Rats," *GLIA 9*: 292–304, 1993.

Carlstedt et al., "Nerve Fibre Regeneration Across the PNS–CNS Interface at the Root–Spinal Cord Junction," *Brain Research Bulletin 22*: 93–102, 1989.

Doherty and Walsh, "CAM–FGF Receptor Interactions: A Model for Axonal Growth," *Molecular and Cellular Neuroscience 8* 99–111, 1996.

Saffell et al., "Expression of a Dominant Negative FGF Receptor Inhibits Axonal Growth and FGF Receptor Phosphorylation Stimulated by CAMs," *Neuron*, pp. 231–242, Feb. 1997.

Blaschuk et al., "E–Cadherin, estrogens and cancer: is there a connection?" *The Canadian Journal of Oncology 4*(4): 291–301, 1994.

Chuah et al., "Differentiation and survival of rat olfactory epithelial neurons in dissociated cell culture," *Developmental Brain Research 60*: 123–132, 1991.

Doherty et al., "Neurite Outgrowth in Response to Transfected N–CAM and N–Cadherin Reveals Fundamental Differences in Neuronal Responsiveness to CAMS," *Neuron 6*: 247–258, 1991.

Gumbiner et al., "The Role of the Cell Adhesion Molecule Uvomorulin in the Formation and Maintenance of the Epithelial Junctional Complex," *The Journal of Cell Biology 107*: 1575–1587, 1988.

Matsuzaki et al., "cDNAs of Cell Adhesion Molecules of Different Specificity Induce Changes in Cell Shape and Border Formation in Cultured S180 Cells," *The Journal of Cell Biology 110*: 1239–1252, 1990.

Mege et al., "Construction of epithelioid sheets by transfection of mouse sarcoma cells with cDNAs for chicken cell adhesion molecules," *Proc. Natl. Acad. Sci. USA 85*: 7274–7278, 1988.

Nose et al., "Localization of Specificity Determining Sites in Cadherin Cell Adhesion Molecules," *Cell 61*: 147–155, 1990.

Duncan et al., "Transplantation of oligodendrocytes and Schwann cells into the spinal cord of the myelin–deficient rat," *Journal of Neurocytology 17*: 351–360, 1988.

Fok–Seang et al., "An analysis of astrocytic cell lines with different abilities to promote axon growth," *Brain Research 689*: 207–223, 1995.

Fok–Seang et al., "Migration of Oligodendrocyte Precursors on Astrocytes and Meningeal Cells," *Developmental Biology 171*: 1–15, 1995.

Franz, "Percutaneous Absorption. On The Relevance Of In Vitro Data," *The Journal of Investigative Dermatology 64*(3): 190–195, 1975.

Franz, "The Finite Dose Technique as a Valid in Vitro Model for the Study of Percutaneous Absorption in Man," *Curr. Probl. Dermatol. 7*: 58–68, 1978.

Ghirnikar and Eng, "Astrocyte–Schwann Cell Interactions in Culture," *GLIA 11*: 367–377, 1994.

Iruela–Arispe et al., "Expression of SPARC during Development of the Chicken Chorioallantoic Membrane: Evidence for Regulated Proteolysis In Vivo," *Molecular Biology of the Cell 6*: 327–343, 1995.

Liuzzi and Lasek, "Astrocytes Block Axonal Regeneration in Mammals by Activating the Physiological Stop Pathway," *Science 237*: 642–645, 1987.

McCarthy and Vellis, "Preparation of Separate Astroglial and Oligodendroglial Cell Cultures from Rat Cerebral Tissue," *J. Cell Biology 85*: 890–902, 1980.

Orr, "Angiogenesis Research Offers New Approaches to Treatment of Disease," *Genetic Engineering News*, pp. 15–16, 42, May 1, 1996.

* cited by examiner

```
human n-cad    D W V I P P I N L P E N S R G P F P Q E L V R I R S D R D K N L S L R I R V T G P G A D
mouse n-cad    D W V I P P I N L P E N S R G P F P Q E L V R I R S D R D K N L S L R Y S V T G P G A D
bovine n-cad   D W V I P P I N L P E N S R G P F P Q E L V R I R S D R D K N L S L R Y S V T G P G A D
human e-cad    D W V I P P I S C P E N E K G P F P K N L V Q I K S N K D K E G K V F Y S I T G Q G A D
mouse e-cad    D W V I P P I S C P E N E K G E F P K N L V Q I K S N R D K E T K V F Y S I T G Q G A D
human p-cad    D W V V A P I S V P E N G K G P F P Q R L N Q L K S N K D R D T K I F Y S I T G P G A D
mouse p-cad    E W V M P P I F V P E N G K G P F P Q R L N Q L K S N K D R G T K I F Y S I T G P G A D
human r-cad    D W V I P P I N V P E N S R G P F P Q Q L V R I R S D K D N D I P I R Y S I T G V G A D
mouse r-cad    D W V I P P I N V P E N S R G P F P Q Q L V R I R S D K D N D I P I R Y S I T G V G A D
identity         : :       : :     : : :     :   : :     :         :         :           : :   : : :
consensus      d W V i p P I . . P E N . . G p F P q . L v . i . S . . D . . . . . . y s i T G . G A D human n-cad    Q P P T G I F I L N P I S G Q L S V T K P L D R Q Q N A R F H L G A H A V D I N G N Q V
mouse n-cad    Q P P T G I F I I N P I S G Q L S V T K P L D R E L I A R F H L R A H A V D I N G N Q V
bovine n-cad   Q P P T G I F I I N P I S G Q L S V T K P L D R E L I A R F H L R A H A V D I N G N Q V
human e-cad    T P P V G V F I I E R E T G W L K V T E P L D R E R I A T Y T L F S H A V S S N G N A V
mouse e-cad    K P P V G V F I I E R E T G W L K V T Q P L D R E A I A K Y I L Y S H A V S S N G E A V
human p-cad    S P P E G V F A V E K E T G W L L L N K P L D R E E I A K Y E L F G H A V S E N G A S V
mouse p-cad    S P P E G V F T I E K E S G W L L L H M P L D R E K I V K Y E L Y G H A V S E N G A S V
human r-cad    Q P P M E V F S I N S M S G R M Y V T R P M D R E E H A S Y H L R A H A V D M N G N K V
mouse r-cad    Q P P M E V F N I D S M S G R M Y V T R P M D R E E R A S Y H L R A H A V D M N G N K V
identity         : :       :                 :           : :           : : :     : :     :
consensus      . P P . g v F . i . . . s G . I . v t . P I D R e . i a . y . L . . H A V . . N G n . V human n-cad    E T P I D I V I N V I D M N D N R P E F
mouse n-cad    E N P I D I V I N V I D M N D N R P E F
bovine n-cad   E N P I D I V I N V I D M N D N R P E F
human e-cad    E D P M E I L I T V T D Q N D N K P E F
mouse e-cad    E D P M E I V I T V T D Q N D N R P E F
human p-cad    E D P M N I S I I V T D Q N D H K P K F
mouse p-cad    E E P M N I S I I V T D Q N D N K P K F
human r-cad    E N P I D L Y I Y V I D M N D N H P E F
mouse r-cad    E N P I D L Y I Y V I D M N D N R P E F
identity         :       :   :   :   :   : :         :   :
consensus      E . P . . i . I . V . D . N D n . P e F
```

*Fig. 2*

```
human n-cad   A P N P K I I R Q E E G L H A G T M L T T F T A Q D P D R Y M Q Q K Y L R Y T K L S D P
mouse n-cad   A P N P K I I R Q E E G L H A G T M L T T L T A Q D P D R Y M Q Q N - I R Y T K L S D P
bovine n-cad  A P N P K I I R Q E E G L H A G T V L T T F T A Q D P D R Y M Q Q N - I R Y T K L S D P
human e-cad   V P P E K R V E V S E D F G V G Q E I T S Y T A Q E P D T F M E Q K - I T Y R I W R D T
mouse e-cad   M P A E R R V E V P E D F G V G Q E I T S Y T A R E P D T F M D Q K - I T Y R I W R D T
human p-cad   V P P S K V V E V Q E G I P T G E P V C V Y T A E D P D - K E N Q K - I S Y R I L R D P
mouse p-cad   V P P S K V I E A Q E G I S I G E L V C I Y T A Q D P D - K E D Q K - I S Y T I S R D P
human r-cad   P S N H K L I R L E E G V P P G T V L T T F S A V D P D R F M Q Q A - V R Y S K L S D P
mouse r-cad   P S N H K L I R L E E G V P A G T A L T T F S A V D P D R P M Q Q A - V R Y S K L S D P
identity                          :                :           :                  :           :
consensus     . p . . . k . i . . . E g . . . G . . . t . . t A . d P D r . m . Q . . . i . Y . . I . D p human n-cad   A N W L K I D P V N G Q I T T I A V L D R E S - P N V K N N I Y N A T F L A S D N G I P
mouse n-cad   A N W L K I D P V N G Q I T T I A V L D R E S - P Y V Q N N I Y N A T F L A S D N G I P
bovine n-cad  A N W L K I D S V N G Q I T T I A V L D R E S - P N V K A N I Y N A T F L A S D N G I P
human e-cad   R N W L E I N P D T G A I S T R A E L D R E D F E H V K N S T Y T A L I I A T D N G S P
mouse e-cad   A N W L E I N P E T G A I F T R A E M D R E D A E H V K N S T Y V A L I I A T D D G S P
human p-cad   A G W L A M D P D S G Q V T A V G T L D R E D E Q F V R N N I Y E V M V L A M D N G S P
mouse p-cad   A N W L A V D P D S G Q I T A A G I L D R E D E Q F V K N N V Y E V M V L A T D S G N P
human r-cad   A S W L H I N A T N G Q I T T V A V L D R E S - L Y T K N N V Y E A T F L A A D N G I P
mouse r-cad   A N W L H I N T S N G Q I T T A A I L D R E S - L Y T K N N V Y E A T F L A A D N G I P
identity         : :                :             : : :                :         :   :   :   :
consensus     a n W L . i . p . . G q i t t . a . I D R E . . . . v k n n . Y . a . . I A . D n G . P human n-cad   P M S G T G T L Q I Y L L D I N D N A P
mouse n-cad   P M S G T G T L Q I Y L L D I N D N A P
bovine n-cad  P M S G T G T L Q I Y L L D I N D N A P
human e-cad   V A T G T G T L L L I L S D V N D N A P
mouse e-cad   I A T G T G T L L L V L L D V N D N A P
human p-cad   P T T G T G T L L L T L I D V N D H G P
mouse p-cad   P T T G T G T L L L T L T D I N D H G P
human r-cad   P A S G T G T L Q I Y L I D I N D N A P
mouse r-cad   P A S G T G T L Q I Y L I D I N D N A P
identity         : : : : :       :   :   : :           :
consensus     p . . G T G T L . . . L . D i N D n a P
```

*Fig. 3*

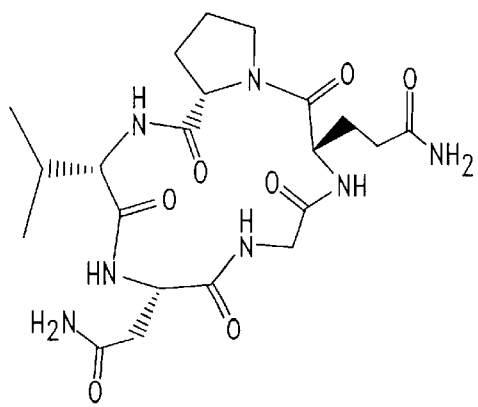
PVNGQ
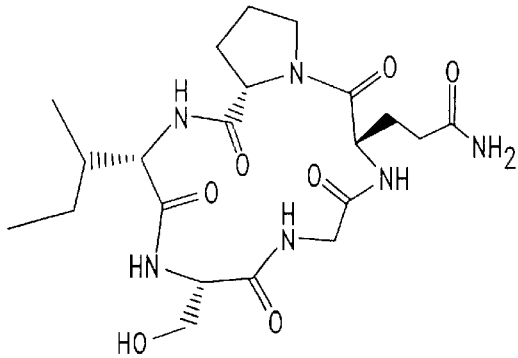
PISGQ
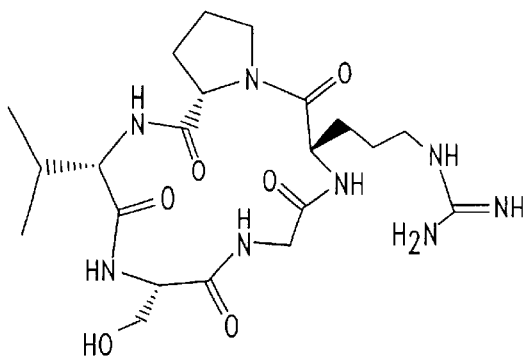
PVSGR
*Fig. 4A*

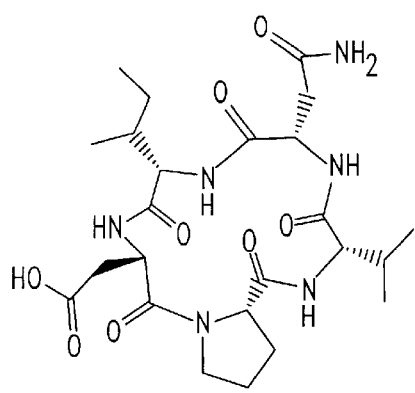
IDPVN
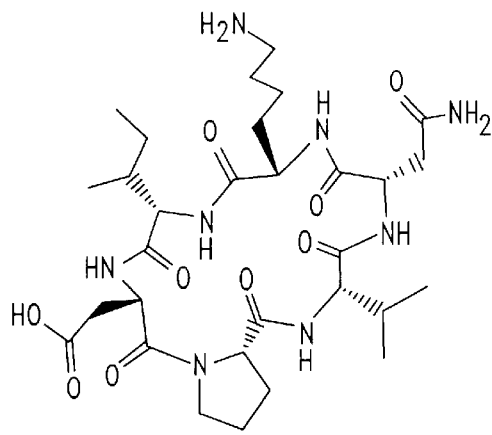
KIDPVN
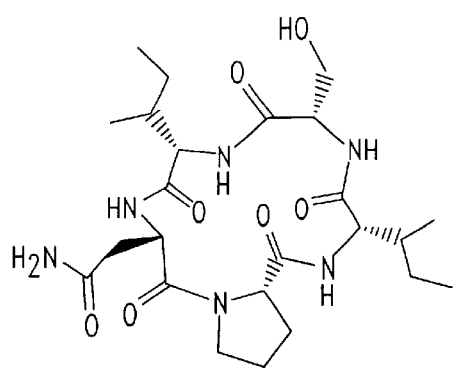
INPIS
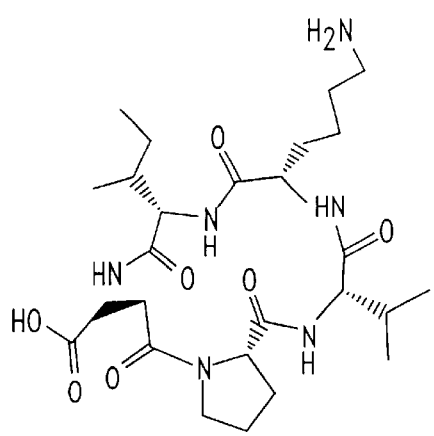
KIDPV
Fig. 4B

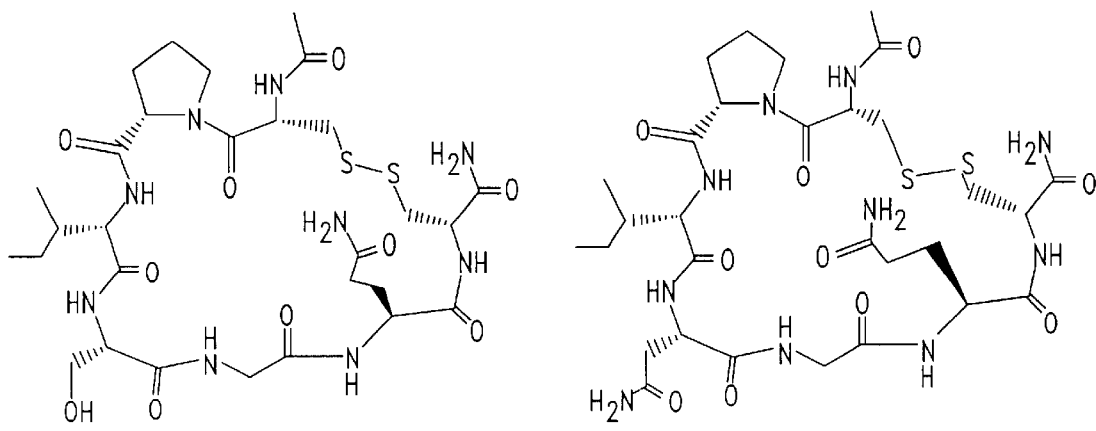
N-Ac-CPISGQC-NH$_2$     N-Ac-CPVNGQC-NH$_2$
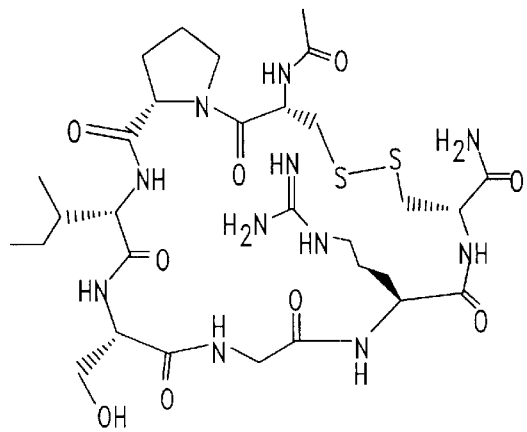
N-Ac-CPVSGRC-NH$_2$
Fig. 4C

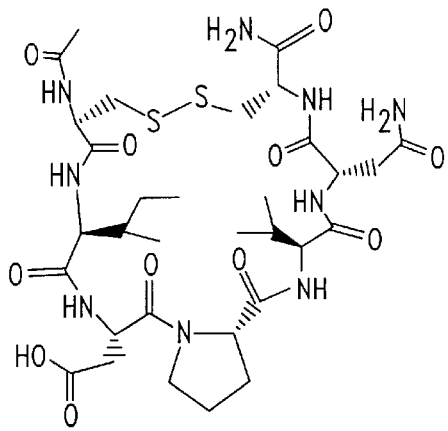
N-Ac-CIDPVNC-NH₂
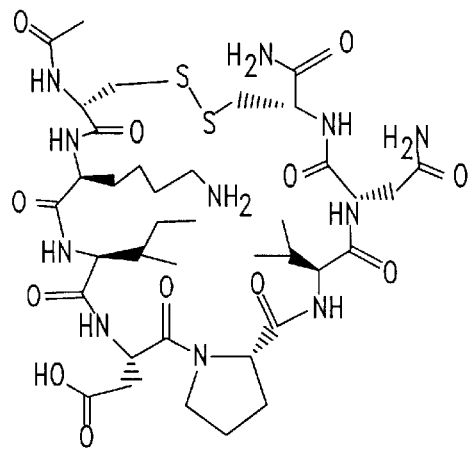
N-Ac-CKIDPVNC-NH₂
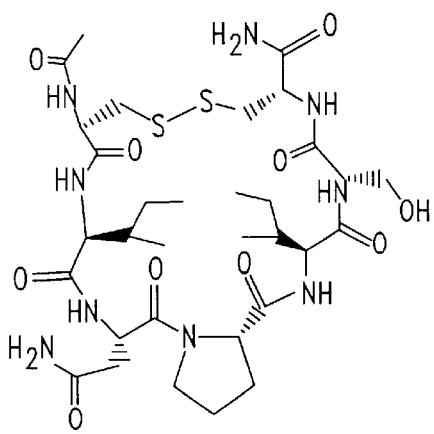
N-Ac-CINPISC-NH₂
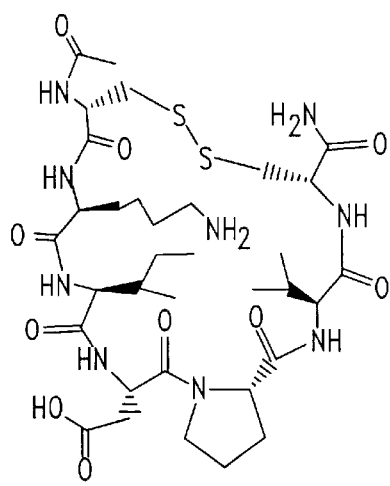
N-Ac-CKIDPVC-NH₂
Fig. 4D

SEQUENCE LISTING

<160> NUMBER OF SEQ ID NOS: 87

<210> SEQ ID NO: 1
<211> LENGTH: 5
<212> TYPE: PRT
<213> ORGANISM: Artificial Sequence
<220> FEATURE:
<223> OTHER INFORMATION: Description of Artificial Sequence: Solid
      Phase Synthesis
<221> NAME/KEY: MOD_RES
<222> LOCATION: (2)
<223> OTHER INFORMATION: Where Xaa is Independently Selected from the
      Group Consisting of Amino Acids

<400> SEQUENCE: 1

Asp Xaa Asn Asp Asn
 1               5

<210> SEQ ID NO: 2
<211> LENGTH: 4
<212> TYPE: PRT
<213> ORGANISM: Artificial Sequence
<220> FEATURE:
<223> OTHER INFORMATION: Description of Artificial Sequence: Solid
      Phase Synthesis

<400> SEQUENCE: 2

Leu Asp Arg Glu
 1

<210> SEQ ID NO: 3
<211> LENGTH: 11
<212> TYPE: PRT
<213> ORGANISM: Artificial Sequence
<220> FEATURE:
<223> OTHER INFORMATION: Description of Artificial Sequence: Solid
      Phase Synthesis
<221> NAME/KEY: MOD_RES
<222> LOCATION: (1)
<223> OTHER INFORMATION: Where Xaa is either Isoleucine or Valine
<221> NAME/KEY: MOD_RES
<222> LOCATION: (3)
<223> OTHER INFORMATION: Where Xaa is independently selected from the
      group consisting of amino acid residues
<221> NAME/KEY: MOD_RES
<222> LOCATION: (5)
<223> OTHER INFORMATION: Where Xaa is independently selected from the
      group consisting of amino acid residues
<221> NAME/KEY: MOD_RES
<222> LOCATION: (6)
<223> OTHER INFORMATION: Where Xaa is independently selected from the
      group consisting of amino acid residues
<221> NAME/KEY: MOD_RES
<222> LOCATION: (7)
<223> OTHER INFORMATION: Where Xaa is independently selected from the
      group consisting of amino acid residues
<221> NAME/KEY: MOD_RES
<222> LOCATION: (8)
<223> OTHER INFORMATION: Where Xaa is either Serine or Threonine
<221> NAME/KEY: MOD_RES
<222> LOCATION: (10)
<223> OTHER INFORMATION: Where Xaa is independently selected from the
      group consisting of amino acid residues
<221> NAME/KEY: MOD_RES
<222> LOCATION: (11)
<223> OTHER INFORMATION: Where Xaa is either Leucine or Methionine

<400> SEQUENCE: 3

Xaa Phe Xaa Ile Xaa Xaa Xaa Xaa Gly Xaa Xaa
 1               5                  10

```
<210> SEQ ID NO: 4
<211> LENGTH: 11
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (3)
<223> OTHER INFORMATION: Where Xaa is independently selected from the
      group consisting of amino acid residues
<221> NAME/KEY: MOD_RES
<222> LOCATION: (5)
<223> OTHER INFORMATION: Where Xaa is either Aspartic Acid or Asparagine
<221> NAME/KEY: MOD_RES
<222> LOCATION: (6)
<223> OTHER INFORMATION: Where Xaa is independently selected from the
      group consisting of amino acid residues
<221> NAME/KEY: MOD_RES
<222> LOCATION: (7)
<223> OTHER INFORMATION: Where Xaa is independently selected from the
      group consisting of amino acid residues
<221> NAME/KEY: MOD_RES
<222> LOCATION: (8)
<223> OTHER INFORMATION: Where Xaa is independently selected from the
      group consisting of amino acid residues

<400> SEQUENCE: 4

Trp Leu Xaa Ile Xaa Xaa Xaa Xaa Gly Gln Ile
 1               5                  10

<210> SEQ ID NO: 5
<211> LENGTH: 11
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (11)...(11)
<223> OTHER INFORMATION: Residue may be native or modified

<400> SEQUENCE: 5

Ile Phe Ile Ile Asn Pro Ile Ser Gly Gln Leu
 1               5                  10

<210> SEQ ID NO: 6
<211> LENGTH: 11
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (11)...(11)
<223> OTHER INFORMATION: Residue may be native or modified

<400> SEQUENCE: 6

Ile Phe Ile Leu Asn Pro Ile Ser Gly Gln Leu
 1               5                  10

<210> SEQ ID NO: 7
<211> LENGTH: 11
<212> TYPE: PRT
<213> ORGANISM: Artificial Sequence
<220> FEATURE:
```

```
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (11)...(11)
<223> OTHER INFORMATION: Residue may be native or modified

<400> SEQUENCE: 7

Val Phe Ala Val Glu Lys Glu Thr Gly Trp Leu
 1               5                  10

<210> SEQ ID NO: 8
<211> LENGTH: 11
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (11)...(11)
<223> OTHER INFORMATION: Residue may be native or modified

<400> SEQUENCE: 8

Val Phe Ser Ile Asn Ser Met Ser Gly Arg Met
 1               5                  10

<210> SEQ ID NO: 9
<211> LENGTH: 11
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (11)...(11)
<223> OTHER INFORMATION: Residue may be native or modified

<400> SEQUENCE: 9

Val Phe Ile Ile Glu Arg Glu Thr Gly Trp Leu
 1               5                  10

<210> SEQ ID NO: 10
<211> LENGTH: 11
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (11)...(11)
<223> OTHER INFORMATION: Residue may be native or modified

<400> SEQUENCE: 10

Val Phe Thr Ile Glu Lys Glu Ser Gly Trp Leu
 1               5                  10

<210> SEQ ID NO: 11
<211> LENGTH: 11
<212> TYPE: PRT
<213> ORGANISM: Artificial Sequence
```

```
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (11)...(11)
<223> OTHER INFORMATION: Residue may be native or modified

<400> SEQUENCE: 11

Val Phe Asn Ile Asp Ser Met Ser Gly Arg Met
 1               5                  10

<210> SEQ ID NO: 12
<211> LENGTH: 11
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (11)...(11)
<223> OTHER INFORMATION: Residue may be native or modified

<400> SEQUENCE: 12

Trp Leu Lys Ile Asp Ser Val Asn Gly Gln Ile
 1               5                  10

<210> SEQ ID NO: 13
<211> LENGTH: 11
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (11)...(11)
<223> OTHER INFORMATION: Residue may be native or modified

<400> SEQUENCE: 13

Trp Leu Lys Ile Asp Pro Val Asn Gly Gln Ile
 1               5                  10

<210> SEQ ID NO: 14
<211> LENGTH: 11
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (11)...(11)
<223> OTHER INFORMATION: Residue may be native or modified

<400> SEQUENCE: 14

Trp Leu Ala Met Asp Pro Asp Ser Gly Gln Val
 1               5                  10

<210> SEQ ID NO: 15
<211> LENGTH: 11
<212> TYPE: PRT
```

```
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (11)...(11)
<223> OTHER INFORMATION: Residue may be native or modified

<400> SEQUENCE: 15

Trp Leu His Ile Asn Ala Thr Asn Gly Gln Ile
  1               5                  10

<210> SEQ ID NO: 16
<211> LENGTH: 11
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (11)...(11)
<223> OTHER INFORMATION: Residue may be native or modified

<400> SEQUENCE: 16

Trp Leu Glu Ile Asn Pro Asp Thr Gly Ala Ile
  1               5                  10

<210> SEQ ID NO: 17
<211> LENGTH: 11
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (11)...(11)
<223> OTHER INFORMATION: Residue may be native or modified

<400> SEQUENCE: 17

Trp Leu Ala Val Asp Pro Asp Ser Gly Gln Ile
  1               5                  10

<210> SEQ ID NO: 18
<211> LENGTH: 11
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (11)...(11)
<223> OTHER INFORMATION: Residue may be native or modified

<400> SEQUENCE: 18

Trp Leu Glu Ile Asn Pro Glu Thr Gly Ala Ile
  1               5                  10

<210> SEQ ID NO: 19
<211> LENGTH: 11
```

```
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (11)...(11)
<223> OTHER INFORMATION: Residue may be native or modified

<400> SEQUENCE: 19

Trp Leu His Ile Asn Thr Ser Asn Gly Gln Ile
 1               5                  10

<210> SEQ ID NO: 20
<211> LENGTH: 11
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (11)...(11)
<223> OTHER INFORMATION: Residue may be native or modified

<400> SEQUENCE: 20

Asn Leu Lys Ile Asp Pro Val Asn Gly Gln Ile
 1               5                  10

<210> SEQ ID NO: 21
<211> LENGTH: 10
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (10)...(10)
<223> OTHER INFORMATION: Residue may be native or modified

<400> SEQUENCE: 21

Leu Lys Ile Asp Pro Val Asn Gly Gln Ile
 1               5                  10

<210> SEQ ID NO: 22
<211> LENGTH: 7
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (7)...(7)
<223> OTHER INFORMATION: Residue may be native or modified

<400> SEQUENCE: 22

Ile Asn Pro Ile Ser Gly Gln
 1               5

<210> SEQ ID NO: 23
```

```
<211> LENGTH: 7
<212> TYPE: PRT
<213> ORGANISM: Artificial Sequence
<220> FEATURE:
<223> OTHER INFORMATION: Description of Artificial Sequence: Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (7)...(7)
<223> OTHER INFORMATION: Residue may be native or modified

<400> SEQUENCE: 23

Leu Asn Pro Ile Ser Gly Gln
 1               5

<210> SEQ ID NO: 24
<211> LENGTH: 7
<212> TYPE: PRT
<213> ORGANISM: Artificial Sequence
<220> FEATURE:
<223> OTHER INFORMATION: Description of Artificial Sequence: Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (7)...(7)
<223> OTHER INFORMATION: Residue may be native or modified

<400> SEQUENCE: 24

Ile Asp Pro Val Ser Gly Gln
 1               5

<210> SEQ ID NO: 25
<211> LENGTH: 8
<212> TYPE: PRT
<213> ORGANISM: Artificial Sequence
<220> FEATURE:
<223> OTHER INFORMATION: Description of Artificial Sequence: Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (8)...(8)
<223> OTHER INFORMATION: Residue may be native or modified

<400> SEQUENCE: 25

Lys Ile Asp Pro Val Asn Gly Gln
 1               5

<210> SEQ ID NO: 26
<211> LENGTH: 5
<212> TYPE: PRT
<213> ORGANISM: Artificial Sequence
<220> FEATURE:
<223> OTHER INFORMATION: Description of Artificial Sequence: Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (5)...(5)
<223> OTHER INFORMATION: Residue may be native or modified

<400> SEQUENCE: 26

Pro Ile Ser Gly Gln
 1               5
```

```
<210> SEQ ID NO: 27
<211> LENGTH: 5
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (5)...(5)
<223> OTHER INFORMATION: Residue may be native or modified

<400> SEQUENCE: 27

Pro Val Asn Gly Gln
 1               5

<210> SEQ ID NO: 28
<211> LENGTH: 5
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (5)...(5)
<223> OTHER INFORMATION: Residue may be native or modified

<400> SEQUENCE: 28

Pro Val Ser Gly Arg
 1               5

<210> SEQ ID NO: 29
<211> LENGTH: 5
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (5)...(5)
<223> OTHER INFORMATION: Residue may be native or modified

<400> SEQUENCE: 29

Ile Asp Pro Val Asn
 1               5

<210> SEQ ID NO: 30
<211> LENGTH: 5
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (5)...(5)
<223> OTHER INFORMATION: Residue may be native or modified

<400> SEQUENCE: 30

Ile Asn Pro Ile Ser
 1               5
```

```
<210> SEQ ID NO: 31
<211> LENGTH: 5
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (5)...(5)
<223> OTHER INFORMATION: Residue may be native or modified

<400> SEQUENCE: 31

Lys Ile Asp Pro Val
 1               5

<210> SEQ ID NO: 32
<211> LENGTH: 108
<212> TYPE: PRT
<213> ORGANISM: Homo sapiens

<400> SEQUENCE: 32

Asp Trp Val Ile Pro Pro Ile Asn Leu Pro Glu Asn Ser Arg Gly Pro
 1               5                  10                  15

Phe Pro Gln Glu Leu Val Arg Ile Arg Ser Asp Arg Asp Lys Asn Leu
                20                  25                  30

Ser Leu Arg Ile Arg Val Thr Gly Pro Gly Ala Asp Gln Pro Pro Thr
            35                  40                  45

Gly Ile Phe Ile Leu Asn Pro Ile Ser Gly Gln Leu Ser Val Thr Lys
        50                  55                  60

Pro Leu Asp Arg Gln Gln Asn Ala Arg Phe His Leu Gly Ala His Ala
 65                  70                  75                  80

Val Asp Ile Asn Gly Asn Gln Val Glu Thr Pro Ile Asp Ile Val Ile
                85                  90                  95

Asn Val Ile Asp Met Asn Asp Asn Arg Pro Glu Phe
               100                 105

<210> SEQ ID NO: 33
<211> LENGTH: 108
<212> TYPE: PRT
<213> ORGANISM: Mus musculus

<400> SEQUENCE: 33

Asp Trp Val Ile Pro Pro Ile Asn Leu Pro Glu Asn Ser Arg Gly Pro
 1               5                  10                  15

Phe Pro Gln Glu Leu Val Arg Ile Arg Ser Asp Arg Asp Lys Asn Leu
                20                  25                  30

Ser Leu Arg Tyr Ser Val Thr Gly Pro Gly Ala Asp Gln Pro Pro Thr
            35                  40                  45

Gly Ile Phe Ile Ile Asn Pro Ile Ser Gly Gln Leu Ser Val Thr Lys
        50                  55                  60

Pro Leu Asp Arg Glu Leu Ile Ala Arg Phe His Leu Arg Ala His Ala
 65                  70                  75                  80

Val Asp Ile Asn Gly Asn Gln Val Glu Asn Pro Ile Asp Ile Val Ile
                85                  90                  95

Asn Val Ile Asp Met Asn Asp Asn Arg Pro Glu Phe
               100                 105
```

```
<210> SEQ ID NO: 34
<211> LENGTH: 108
<212> TYPE: PRT
<213> ORGANISM: Bos taurus

<400> SEQUENCE: 34

Asp Trp Val Ile Pro Pro Ile Asn Leu Pro Glu Asn Ser Arg Gly Pro
 1               5                   10                  15

Phe Pro Gln Glu Leu Val Arg Ile Arg Ser Asp Arg Asp Lys Asn Leu
                20                  25                  30

Ser Leu Arg Tyr Ser Val Thr Gly Pro Gly Ala Asp Gln Pro Pro Thr
            35                  40                  45

Gly Ile Phe Ile Ile Asn Pro Ile Ser Gly Gln Leu Ser Val Thr Lys
        50                  55                  60

Pro Leu Asp Arg Glu Leu Ile Ala Arg Phe His Leu Arg Ala His Ala
 65                 70                  75                  80

Val Asp Ile Asn Gly Asn Gln Val Glu Asn Pro Ile Asp Ile Val Ile
                85                  90                  95

Asn Val Ile Asp Met Asn Asp Asn Arg Pro Glu Phe
            100                 105

<210> SEQ ID NO: 35
<211> LENGTH: 108
<212> TYPE: PRT
<213> ORGANISM: Homo sapiens

<400> SEQUENCE: 35

Asp Trp Val Ile Pro Pro Ile Ser Cys Pro Glu Asn Glu Lys Gly Pro
 1               5                   10                  15

Phe Pro Lys Asn Leu Val Gln Ile Lys Ser Asn Lys Asp Lys Glu Gly
                20                  25                  30

Lys Val Phe Tyr Ser Ile Thr Gly Gln Gly Ala Asp Thr Pro Pro Val
            35                  40                  45

Gly Val Phe Ile Ile Glu Arg Glu Thr Gly Trp Leu Lys Val Thr Glu
        50                  55                  60

Pro Leu Asp Arg Glu Arg Ile Ala Thr Tyr Thr Leu Phe Ser His Ala
 65                 70                  75                  80

Val Ser Ser Asn Gly Asn Ala Val Glu Asp Pro Met Glu Ile Leu Ile
                85                  90                  95

Thr Val Thr Asp Gln Asn Asp Asn Lys Pro Glu Phe
            100                 105

<210> SEQ ID NO: 36
<211> LENGTH: 108
<212> TYPE: PRT
<213> ORGANISM: Mus musculus

<400> SEQUENCE: 36

Asp Trp Val Ile Pro Pro Ile Ser Cys Pro Glu Asn Glu Lys Gly Glu
 1               5                   10                  15

Phe Pro Lys Asn Leu Val Gln Ile Lys Ser Asn Arg Asp Lys Glu Thr
                20                  25                  30

Lys Val Phe Tyr Ser Ile Thr Gly Gln Gly Ala Asp Lys Pro Pro Val
            35                  40                  45

Gly Val Phe Ile Ile Glu Arg Glu Thr Gly Trp Leu Lys Val Thr Gln
        50                  55                  60

Pro Leu Asp Arg Glu Ala Ile Ala Lys Tyr Ile Leu Tyr Ser His Ala
 65                 70                  75                  80
```

Val Ser Ser Asn Gly Glu Ala Val Glu Asp Pro Met Glu Ile Val Ile
                85                  90                  95

Thr Val Thr Asp Gln Asn Asp Asn Arg Pro Glu Phe
            100                 105

<210> SEQ ID NO: 37
<211> LENGTH: 108
<212> TYPE: PRT
<213> ORGANISM: Homo sapiens

<400> SEQUENCE: 37

Asp Trp Val Val Ala Pro Ile Ser Val Pro Glu Asn Gly Lys Gly Pro
 1               5                  10                  15

Phe Pro Gln Arg Leu Asn Gln Leu Lys Ser Asn Lys Asp Arg Asp Thr
            20                  25                  30

Lys Ile Phe Tyr Ser Ile Thr Gly Pro Gly Ala Asp Ser Pro Pro Glu
            35                  40                  45

Gly Val Phe Ala Val Glu Lys Glu Thr Gly Trp Leu Leu Leu Asn Lys
        50                  55                  60

Pro Leu Asp Arg Glu Glu Ile Ala Lys Tyr Glu Leu Phe Gly His Ala
65                  70                  75                  80

Val Ser Glu Asn Gly Ala Ser Val Glu Asp Pro Met Asn Ile Ser Ile
                85                  90                  95

Ile Val Thr Asp Gln Asn Asp His Lys Pro Lys Phe
            100                 105

<210> SEQ ID NO: 38
<211> LENGTH: 108
<212> TYPE: PRT
<213> ORGANISM: Mus musculus

<400> SEQUENCE: 38

Glu Trp Val Met Pro Pro Ile Phe Val Pro Glu Asn Gly Lys Gly Pro
 1               5                  10                  15

Phe Pro Gln Arg Leu Asn Gln Leu Lys Ser Asn Lys Asp Arg Gly Thr
            20                  25                  30

Lys Ile Phe Tyr Ser Ile Thr Gly Pro Gly Ala Asp Ser Pro Pro Glu
            35                  40                  45

Gly Val Phe Thr Ile Glu Lys Glu Ser Gly Trp Leu Leu Leu His Met
        50                  55                  60

Pro Leu Asp Arg Glu Lys Ile Val Lys Tyr Glu Leu Tyr Gly His Ala
65                  70                  75                  80

Val Ser Glu Asn Gly Ala Ser Val Glu Glu Pro Met Asn Ile Ser Ile
                85                  90                  95

Ile Val Thr Asp Gln Asn Asp Asn Lys Pro Lys Phe
            100                 105

<210> SEQ ID NO: 39
<211> LENGTH: 108
<212> TYPE: PRT
<213> ORGANISM: Homo sapiens

<400> SEQUENCE: 39

Asp Trp Val Ile Pro Pro Ile Asn Val Pro Glu Asn Ser Arg Gly Pro
 1               5                  10                  15

Phe Pro Gln Gln Leu Val Arg Ile Arg Ser Asp Lys Asp Asn Asp Ile
            20                  25                  30

```
Pro Ile Arg Tyr Ser Ile Thr Gly Val Gly Ala Asp Gln Pro Pro Met
            35                  40                  45

Glu Val Phe Ser Ile Asn Ser Met Ser Gly Arg Met Tyr Val Thr Arg
         50                  55                  60

Pro Met Asp Arg Glu Glu His Ala Ser Tyr His Leu Arg Ala His Ala
 65                  70                  75                  80

Val Asp Met Asn Gly Asn Lys Val Glu Asn Pro Ile Asp Leu Tyr Ile
                 85                  90                  95

Tyr Val Ile Asp Met Asn Asp Asn His Pro Glu Phe
            100                 105
```

<210> SEQ ID NO: 40
<211> LENGTH: 108
<212> TYPE: PRT
<213> ORGANISM: Mus musculus

<400> SEQUENCE: 40

```
Asp Trp Val Ile Pro Pro Ile Asn Val Pro Glu Asn Ser Arg Gly Pro
 1               5                  10                  15

Phe Pro Gln Gln Leu Val Arg Ile Arg Ser Asp Lys Asp Asn Asp Ile
                 20                  25                  30

Pro Ile Arg Tyr Ser Ile Thr Gly Val Gly Ala Asp Gln Pro Pro Met
            35                  40                  45

Glu Val Phe Asn Ile Asp Ser Met Ser Gly Arg Met Tyr Val Thr Arg
         50                  55                  60

Pro Met Asp Arg Glu Glu Arg Ala Ser Tyr His Leu Arg Ala His Ala
 65                  70                  75                  80

Val Asp Met Asn Gly Asn Lys Val Glu Asn Pro Ile Asp Leu Tyr Ile
                 85                  90                  95

Tyr Val Ile Asp Met Asn Asp Asn Arg Pro Glu Phe
            100                 105
```

<210> SEQ ID NO: 41
<211> LENGTH: 107
<212> TYPE: PRT
<213> ORGANISM: Homo sapiens

<400> SEQUENCE: 41

```
Ala Pro Asn Pro Lys Ile Ile Arg Gln Glu Glu Gly Leu His Ala Gly
 1               5                  10                  15

Thr Met Leu Thr Thr Phe Thr Ala Gln Asp Pro Asp Arg Tyr Met Gln
                 20                  25                  30

Gln Lys Tyr Leu Arg Tyr Thr Lys Leu Ser Asp Pro Ala Asn Trp Leu
            35                  40                  45

Lys Ile Asp Pro Val Asn Gly Gln Ile Thr Thr Ile Ala Val Leu Asp
         50                  55                  60

Arg Glu Ser Pro Asn Val Lys Asn Asn Ile Tyr Asn Ala Thr Phe Leu
 65                  70                  75                  80

Ala Ser Asp Asn Gly Ile Pro Pro Met Ser Gly Thr Gly Thr Leu Gln
                 85                  90                  95

Ile Tyr Leu Leu Asp Ile Asn Asp Asn Ala Pro
            100                 105
```

<210> SEQ ID NO: 42
<211> LENGTH: 106
<212> TYPE: PRT
<213> ORGANISM: Mus musculus -continued

<400> SEQUENCE: 42

Ala Pro Asn Pro Lys Ile Ile Arg Gln Glu Glu Gly Leu His Ala Gly
1               5                   10                  15

Thr Met Leu Thr Thr Leu Thr Ala Gln Asp Pro Asp Arg Tyr Met Gln
            20                  25                  30

Gln Asn Ile Arg Tyr Thr Lys Leu Ser Asp Pro Ala Asn Trp Leu Lys
        35                  40                  45

Ile Asp Pro Val Asn Gly Gln Ile Thr Thr Ile Ala Val Leu Asp Arg
    50                  55                  60

Glu Ser Pro Tyr Val Gln Asn Asn Ile Tyr Asn Ala Thr Phe Leu Ala
65                  70                  75                  80

Ser Asp Asn Gly Ile Pro Pro Met Ser Gly Thr Gly Thr Leu Gln Ile
                85                  90                  95

Tyr Leu Leu Asp Ile Asn Asp Asn Ala Pro
            100                 105

<210> SEQ ID NO: 43
<211> LENGTH: 106
<212> TYPE: PRT
<213> ORGANISM: Bos taurus

<400> SEQUENCE: 43

Ala Pro Asn Pro Lys Ile Ile Arg Gln Glu Glu Gly Leu His Ala Gly
1               5                   10                  15

Thr Val Leu Thr Thr Phe Thr Ala Gln Asp Pro Asp Arg Tyr Met Gln
            20                  25                  30

Gln Asn Ile Arg Tyr Thr Lys Leu Ser Asp Pro Ala Asn Trp Leu Lys
        35                  40                  45

Ile Asp Ser Val Asn Gly Gln Ile Thr Thr Ile Ala Val Leu Asp Arg
    50                  55                  60

Glu Ser Pro Asn Val Lys Ala Asn Ile Tyr Asn Ala Thr Phe Leu Ala
65                  70                  75                  80

Ser Asp Asn Gly Ile Pro Pro Met Ser Gly Thr Gly Thr Leu Gln Ile
                85                  90                  95

Tyr Leu Leu Asp Ile Asn Asp Asn Ala Pro
            100                 105

<210> SEQ ID NO: 44
<211> LENGTH: 107
<212> TYPE: PRT
<213> ORGANISM: Homo sapiens

<400> SEQUENCE: 44

Val Pro Pro Glu Lys Arg Val Glu Val Ser Glu Asp Phe Gly Val Gly
1               5                   10                  15

Gln Glu Ile Thr Ser Tyr Thr Ala Gln Glu Pro Asp Thr Phe Met Glu
            20                  25                  30

Gln Lys Ile Thr Tyr Arg Ile Trp Arg Asp Thr Arg Asn Trp Leu Glu
        35                  40                  45

Ile Asn Pro Asp Thr Gly Ala Ile Ser Thr Arg Ala Glu Leu Asp Arg
    50                  55                  60

Glu Asp Phe Glu His Val Lys Asn Ser Thr Tyr Thr Ala Leu Ile Ile
65                  70                  75                  80

Ala Thr Asp Asn Gly Ser Pro Val Ala Thr Gly Thr Gly Thr Leu Leu
                85                  90                  95

Leu Ile Leu Ser Asp Val Asn Asp Asn Ala Pro

-continued

```
                    100                 105

<210> SEQ ID NO: 45
<211> LENGTH: 107
<212> TYPE: PRT
<213> ORGANISM: Mus musculus

<400> SEQUENCE: 45

Met Pro Ala Glu Arg Arg Val Glu Val Pro Glu Asp Phe Gly Val Gly
  1               5                  10                  15

Gln Glu Ile Thr Ser Tyr Thr Ala Arg Glu Pro Asp Thr Phe Met Asp
             20                  25                  30

Gln Lys Ile Thr Tyr Arg Ile Trp Arg Asp Thr Ala Asn Trp Leu Glu
         35                  40                  45

Ile Asn Pro Glu Thr Gly Ala Ile Phe Thr Arg Ala Glu Met Asp Arg
     50                  55                  60

Glu Asp Ala Glu His Val Lys Asn Ser Thr Tyr Val Ala Leu Ile Ile
 65                  70                  75                  80

Ala Thr Asp Asp Gly Ser Pro Ile Ala Thr Gly Thr Gly Thr Leu Leu
                 85                  90                  95

Leu Val Leu Leu Asp Val Asn Asp Asn Ala Pro
            100                 105

<210> SEQ ID NO: 46
<211> LENGTH: 106
<212> TYPE: PRT
<213> ORGANISM: Homo sapiens

<400> SEQUENCE: 46

Val Pro Pro Ser Lys Val Val Glu Val Gln Glu Gly Ile Pro Thr Gly
  1               5                  10                  15

Glu Pro Val Cys Val Tyr Thr Ala Glu Asp Pro Asp Lys Glu Asn Gln
             20                  25                  30

Lys Ile Ser Tyr Arg Ile Leu Arg Asp Pro Ala Gly Trp Leu Ala Met
         35                  40                  45

Asp Pro Asp Ser Gly Gln Val Thr Ala Val Gly Thr Leu Asp Arg Glu
     50                  55                  60

Asp Glu Gln Phe Val Arg Asn Asn Ile Tyr Glu Val Met Val Leu Ala
 65                  70                  75                  80

Met Asp Asn Gly Ser Pro Pro Thr Thr Gly Thr Gly Thr Leu Leu Leu
                 85                  90                  95

Thr Leu Ile Asp Val Asn Asp His Gly Pro
            100                 105

<210> SEQ ID NO: 47
<211> LENGTH: 106
<212> TYPE: PRT
<213> ORGANISM: Mus musculus

<400> SEQUENCE: 47

Val Pro Pro Ser Lys Val Ile Glu Ala Gln Glu Gly Ile Ser Ile Gly
  1               5                  10                  15

Glu Leu Val Cys Ile Tyr Thr Ala Gln Asp Pro Asp Lys Glu Asp Gln
             20                  25                  30

Lys Ile Ser Tyr Thr Ile Ser Arg Asp Pro Ala Asn Trp Leu Ala Val
         35                  40                  45

Asp Pro Asp Ser Gly Gln Ile Thr Ala Ala Gly Ile Leu Asp Arg Glu
     50                  55                  60
```

Asp Glu Gln Phe Val Lys Asn Asn Val Tyr Glu Val Met Val Leu Ala
65                  70                  75                  80

Thr Asp Ser Gly Asn Pro Pro Thr Thr Gly Thr Gly Thr Leu Leu Leu
                85                  90                  95

Thr Leu Thr Asp Ile Asn Asp His Gly Pro
            100                 105

<210> SEQ ID NO: 48
<211> LENGTH: 106
<212> TYPE: PRT
<213> ORGANISM: Homo sapiens

<400> SEQUENCE: 48

Pro Ser Asn His Lys Leu Ile Arg Leu Glu Glu Gly Val Pro Pro Gly
1               5                   10                  15

Thr Val Leu Thr Thr Phe Ser Ala Val Asp Pro Asp Arg Phe Met Gln
                20                  25                  30

Gln Ala Val Arg Tyr Ser Lys Leu Ser Asp Pro Ala Ser Trp Leu His
            35                  40                  45

Ile Asn Ala Thr Asn Gly Gln Ile Thr Thr Val Ala Val Leu Asp Arg
50                  55                  60

Glu Ser Leu Tyr Thr Lys Asn Asn Val Tyr Glu Ala Thr Phe Leu Ala
65                  70                  75                  80

Ala Asp Asn Gly Ile Pro Pro Ala Ser Gly Thr Gly Thr Leu Gln Ile
                85                  90                  95

Tyr Leu Ile Asp Ile Asn Asp Asn Ala Pro
            100                 105

<210> SEQ ID NO: 49
<211> LENGTH: 106
<212> TYPE: PRT
<213> ORGANISM: Mus musculus

<400> SEQUENCE: 49

Pro Ser Asn His Lys Leu Ile Arg Leu Glu Glu Gly Val Pro Ala Gly
1               5                   10                  15

Thr Ala Leu Thr Thr Phe Ser Ala Val Asp Pro Asp Arg Pro Met Gln
                20                  25                  30

Gln Ala Val Arg Tyr Ser Lys Leu Ser Asp Pro Ala Asn Trp Leu His
            35                  40                  45

Ile Asn Thr Ser Asn Gly Gln Ile Thr Thr Ala Ala Ile Leu Asp Arg
50                  55                  60

Glu Ser Leu Tyr Thr Lys Asn Asn Val Tyr Glu Ala Thr Phe Leu Ala
65                  70                  75                  80

Ala Asp Asn Gly Ile Pro Pro Ala Ser Gly Thr Gly Thr Leu Gln Ile
                85                  90                  95

Tyr Leu Ile Asp Ile Asn Asp Asn Ala Pro
            100                 105

<210> SEQ ID NO: 50
<211> LENGTH: 6
<212> TYPE: PRT
<213> ORGANISM: Artificial Sequence
<220> FEATURE:
<223> OTHER INFORMATION: Description of Artificial Sequence: Solid
      Phase Synthesis
<221> NAME/KEY: MOD_RES
<222> LOCATION: (1)...(1)
<223> OTHER INFORMATION: Residue may be native or modified

```
<221> NAME/KEY: MOD_RES
<222> LOCATION: (6)...(6)
<223> OTHER INFORMATION: Residue may be native or modified

<400> SEQUENCE: 50

Lys Ile Asp Pro Val Asn
 1               5

<210> SEQ ID NO: 51
<211> LENGTH: 5
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (5)...(5)
<223> OTHER INFORMATION: Residue may be native or modified

<400> SEQUENCE: 51

Pro Val Asn Gly Gln
 1               5

<210> SEQ ID NO: 52
<211> LENGTH: 5
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (5)...(5)
<223> OTHER INFORMATION: Residue may be native or modified

<400> SEQUENCE: 52

Pro Ile Ser Gly Gln
 1               5

<210> SEQ ID NO: 53
<211> LENGTH: 5
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (5)...(5)
<223> OTHER INFORMATION: Residue may be native or modified

<400> SEQUENCE: 53

Pro Val Ser Gly Arg
 1               5

<210> SEQ ID NO: 54
<211> LENGTH: 5
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
```

```
<223> OTHER INFORMATION: Residue may be native or modified
<221> NAME/KEY: MOD_RES
<222> LOCATION: (5)...(5)
<223> OTHER INFORMATION: Residue may be native or modified

<400> SEQUENCE: 54

Lys Ile Asp Pro Val
 1               5

<210> SEQ ID NO: 55
<211> LENGTH: 6
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (5)...(5)
<223> OTHER INFORMATION: Residue may be native or modified

<400> SEQUENCE: 55

Lys Ile Asp Pro Val Asn
 1               5

<210> SEQ ID NO: 56
<211> LENGTH: 5
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (5)...(5)
<223> OTHER INFORMATION: Residue may be native or modified

<400> SEQUENCE: 56

Ile Asp Pro Val Asn
 1               5

<210> SEQ ID NO: 57
<211> LENGTH: 5
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (5)...(5)
<223> OTHER INFORMATION: Residue may be native or modified

<400> SEQUENCE: 57

Ile Asn Pro Ile Ser
 1               5

<210> SEQ ID NO: 58
<211> LENGTH: 7
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
```

```
<222> LOCATION: (1)...(1)
<223> OTHER INFORMATION: Residue may be native or modified
<221> NAME/KEY: MOD_RES
<222> LOCATION: (7)...(7)
<223> OTHER INFORMATION: Residue may be native or modified

<400> SEQUENCE: 58

Cys Pro Val Asn Gly Gln Cys
  1               5

<210> SEQ ID NO: 59
<211> LENGTH: 7
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (7)...(7)
<223> OTHER INFORMATION: Residue may be native or modified

<400> SEQUENCE: 59

Cys Pro Ile Ser Gly Gln Cys
  1               5

<210> SEQ ID NO: 60
<211> LENGTH: 7
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (7)...(7)
<223> OTHER INFORMATION: Residue may be native or modified

<400> SEQUENCE: 60

Cys Pro Val Ser Gly Arg Cys
  1               5

<210> SEQ ID NO: 61
<211> LENGTH: 8
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (8)...(8)
<223> OTHER INFORMATION: Residue may be native or modified

<400> SEQUENCE: 61

Cys Lys Ile Asp Pro Val Asn Cys
  1               5

<210> SEQ ID NO: 62
<211> LENGTH: 7
<212> TYPE: PRT
<213> ORGANISM: Artificial Sequence
<220> FEATURE:
<223> OTHER INFORMATION: Description of Artificial Sequence:  Solid
      Phase Synthesis
```

```
<221> NAME/KEY: MOD_RES
<222> LOCATION: (1)...(1)
<223> OTHER INFORMATION: Residue may be native or modified
<221> NAME/KEY: MOD_RES
<222> LOCATION: (7)...(7)
<223> OTHER INFORMATION: Residue may be native or modified

<400> SEQUENCE: 62

Cys Ile Asp Pro Val Asn Cys
 1               5

<210> SEQ ID NO: 63
<211> LENGTH: 7
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (7)...(7)
<223> OTHER INFORMATION: Residue may be native or modified

<400> SEQUENCE: 63

Cys Ile Asn Pro Ile Ser Cys
 1               5

<210> SEQ ID NO: 64
<211> LENGTH: 10
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (10)...(10)
<223> OTHER INFORMATION: Residue may be native or modified

<400> SEQUENCE: 64

Leu Lys Ile Asp Pro Ala Asn Gly Gln Ile
 1               5                  10

<210> SEQ ID NO: 65
<211> LENGTH: 10
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (10)...(10)
<223> OTHER INFORMATION: Residue may be native or modified

<400> SEQUENCE: 65

Leu Lys Ile Asp Ala Val Asn Gly Gln Ile
 1               5                  10

<210> SEQ ID NO: 66
<211> LENGTH: 5
<212> TYPE: PRT
<213> ORGANISM: Artificial Sequence
<220> FEATURE:
<223> OTHER INFORMATION: Description of Artificial Sequence:  Solid
```

Phase Synthesis

<400> SEQUENCE: 66

Tyr Ile Gly Ser Arg
 1               5

<210> SEQ ID NO: 67
<211> LENGTH: 10
<212> TYPE: PRT
<213> ORGANISM: Artificial Sequence
<220> FEATURE:
<223> OTHER INFORMATION: Description of Artificial Sequence:  Solid
      Phase Synthesis

<400> SEQUENCE: 67

Lys Tyr Ser Phe Asn Tyr Asp Gly Ser Glu
 1               5                  10

<210> SEQ ID NO: 68
<211> LENGTH: 17
<212> TYPE: PRT
<213> ORGANISM: Artificial Sequence
<220> FEATURE:
<223> OTHER INFORMATION: Description of Artificial Sequence:  Solid
      Phase Synthesis

<400> SEQUENCE: 68

Ile Trp Lys His Lys Gly Arg Asp Val Ile Leu Lys Lys Asp Val Arg
 1               5                  10                  15
Phe

<210> SEQ ID NO: 69
<211> LENGTH: 48
<212> TYPE: PRT
<213> ORGANISM: Artificial Sequence
<220> FEATURE:
<223> OTHER INFORMATION: Description of Artificial Sequence:  Solid
      Phase Synthesis

<400> SEQUENCE: 69

Gly Val Asn Pro Thr Ala Gln Ser Ser Gly Ser Leu Tyr Gly Ser Gln
 1               5                  10                  15

Ile Tyr Ala Leu Cys Asn Gln Phe Tyr Thr Pro Ala Thr Gly Leu
                20                  25                  30

Tyr Val Asp Gln Tyr Leu Tyr His Tyr Cys Val Val Asp Pro Gln Glu
            35                  40                  45

<210> SEQ ID NO: 70
<211> LENGTH: 4
<212> TYPE: PRT
<213> ORGANISM: Artificial Sequence
<220> FEATURE:
<223> OTHER INFORMATION: Description of Artificial Sequence:  Solid
      Phase Synthesis

<400> SEQUENCE: 70

Leu Tyr His Tyr
 1

<210> SEQ ID NO: 71
<211> LENGTH: 4
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES

```
<222> LOCATION: (1)...(1)
<223> OTHER INFORMATION: Residue may be native or modified
<221> NAME/KEY: MOD_RES
<222> LOCATION: (4)...(4)
<223> OTHER INFORMATION: Residue may be native or modified

<400> SEQUENCE: 71

Ile Asp Asp Lys
 1

<210> SEQ ID NO: 72
<211> LENGTH: 4
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (4)...(4)
<223> OTHER INFORMATION: Residue may be native or modified

<400> SEQUENCE: 72

Asp Asp Lys Ser
 1

<210> SEQ ID NO: 73
<211> LENGTH: 5
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (5)...(5)
<223> OTHER INFORMATION: Residue may be native or modified

<400> SEQUENCE: 73

Val Ile Asp Asp Lys
 1               5

<210> SEQ ID NO: 74
<211> LENGTH: 5
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (5)...(5)
<223> OTHER INFORMATION: Residue may be native or modified

<400> SEQUENCE: 74

Ile Asp Asp Lys Ser
 1               5

<210> SEQ ID NO: 75
<211> LENGTH: 6
<212> TYPE: PRT
<213> ORGANISM: Artificial Sequence
<220> FEATURE:
<223> OTHER INFORMATION: Description of Artificial Sequence:  Solid
      Phase Synthesis
```

```
<221> NAME/KEY: MOD_RES
<222> LOCATION: (1)...(1)
<223> OTHER INFORMATION: Residue may be native or modified
<221> NAME/KEY: MOD_RES
<222> LOCATION: (6)...(6)
<223> OTHER INFORMATION: Residue may be native or modified

<400> SEQUENCE: 75

Val Ile Asp Asp Lys Ser
 1               5

<210> SEQ ID NO: 76
<211> LENGTH: 5
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (5)...(5)
<223> OTHER INFORMATION: Residue may be native or modified

<400> SEQUENCE: 76

Asp Asp Lys Ser Gly
 1               5

<210> SEQ ID NO: 77
<211> LENGTH: 6
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (6)...(6)
<223> OTHER INFORMATION: Residue may be native or modified

<400> SEQUENCE: 77

Ile Asp Asp Lys Ser Gly
 1               5

<210> SEQ ID NO: 78
<211> LENGTH: 7
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (7)...(7)
<223> OTHER INFORMATION: Residue may be native or modified

<400> SEQUENCE: 78

Val Ile Asp Asp Lys Ser Gly
 1               5

<210> SEQ ID NO: 79
<211> LENGTH: 6
<212> TYPE: PRT
<213> ORGANISM: Artificial Sequence
<220> FEATURE:
<223> OTHER INFORMATION: Description of Artificial Sequence:  Solid
```

```
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (6)...(6)
<223> OTHER INFORMATION: Residue may be native or modified

<400> SEQUENCE: 79

Phe Val Ile Asp Asp Lys
  1               5

<210> SEQ ID NO: 80
<211> LENGTH: 7
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (7)...(7)
<223> OTHER INFORMATION: Residue may be native or modified

<400> SEQUENCE: 80

Phe Val Ile Asp Asp Lys Ser
  1               5

<210> SEQ ID NO: 81
<211> LENGTH: 8
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (8)...(8)
<223> OTHER INFORMATION: Residue may be native or modified

<400> SEQUENCE: 81

Phe Val Ile Asp Asp Lys Ser Gly
  1               5

<210> SEQ ID NO: 82
<211> LENGTH: 7
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (7)...(7)
<223> OTHER INFORMATION: Residue may be native or modified

<400> SEQUENCE: 82

Ile Phe Val Ile Asp Asp Lys
  1               5

<210> SEQ ID NO: 83
<211> LENGTH: 8
<212> TYPE: PRT
<213> ORGANISM: Artificial Sequence
<220> FEATURE:
```

```
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (8)...(8)
<223> OTHER INFORMATION: Residue may be native or modified

<400> SEQUENCE: 83

Ile Phe Val Ile Asp Asp Lys Ser
 1               5

<210> SEQ ID NO: 84
<211> LENGTH: 9
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (9)...(9)
<223> OTHER INFORMATION: Residue may be native or modified

<400> SEQUENCE: 84

Ile Phe Val Ile Asp Asp Lys Ser Gly
 1               5

<210> SEQ ID NO: 85
<211> LENGTH: 7
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)...(1)
<223> OTHER INFORMATION: Residue may be native or modified
<221> NAME/KEY: MOD_RES
<222> LOCATION: (7)...(7)
<223> OTHER INFORMATION: Residue may be native or modified

<400> SEQUENCE: 85

Cys Lys Ile Asp Pro Val Cys
 1               5

<210> SEQ ID NO: 86
<211> LENGTH: 4
<212> TYPE: PRT
<213> ORGANISM: Artificial Sequence
<220> FEATURE:
<223> OTHER INFORMATION: Description of Artificial Sequence:  Solid
      Phase Synthesis
<221> NAME/KEY: MOD_RES
<222> LOCATION: (1)
<223> OTHER INFORMATION: Where Xaa is Independently Selected from the
      Group Consisting of Amino Acids
<221> NAME/KEY: MOD_RES
<222> LOCATION: (3)
<223> OTHER INFORMATION: Where Xaa is Independently Selected from the
      Group Consisting of Amino Acids

<400> SEQUENCE: 86

Xaa Asp Xaa Glu
 1

<210> SEQ ID NO: 87
<211> LENGTH: 4
```

-continued

```
<212> TYPE: PRT
<213> ORGANISM: Artificial Sequence
<220> FEATURE:
<223> OTHER INFORMATION: Description of Artificial Sequence:  Solid
      Phase Synthesis

<400> SEQUENCE: 87

Asp Val Asn Glu
```

COMPOUNDS AND METHODS FOR MODULATING ADHESION MOLECULE FUNCTION

TECHNICAL FIELD

The present invention relates generally to methods for modulating cadherin-mediated processes, and more particularly to the use of modulating agents comprising a cadherin cell adhesion recognition sequence, or an antibody that specifically recognizes such a sequence, for inhibiting or enhancing functions such as cell adhesion.

BACKGROUND OF THE INVENTION

Cell adhesion is a complex process that is important for maintaining tissue integrity and generating physical and permeability barriers within the body. All tissues are divided into discrete compartments, each of which is composed of a specific cell type that adheres to similar cell types. Such adhesion triggers the formation of intercellular junctions (i.e., readily definable contact sites on the surfaces of adjacent cells that are adhering to one another), also known as tight junctions, gap junctions and belt desmosomes. The formation of such junctions gives rise to physical and permeability barriers that restrict the free passage of cells and other biological substances from one tissue compartment to another. For example, the blood vessels of all tissues are composed of endothelial cells. In order for components in the blood to enter a given tissue compartment, they must first pass from the lumen of a blood vessel through the barrier formed by the endothelial cells of that vessel. Similarly, in order for substances to enter the body via the gut, the substances must first pass through a barrier formed by the epithelial cells of that tissue. To enter the blood via the skin, both epithelial and endothelial cell layers must be crossed.

Cell adhesion is mediated by specific cell surface adhesion molecules (CAMs). There are many different families of CAMs, including the immunoglobulin, integrin, selectin and cadherin superfamilies, and each cell type expresses a unique combination of these molecules. Cadherins are a rapidly expanding family of calcium-dependent CAMs (Munro et al., *In: Cell Adhesion and Invasion in Cancer Metastasis*, P. Brodt, ed., pp. 17≅34, RG Landes Co. (Austin Tex., 1996). The classical cadherins (abbreviated CADs) are integral membrane glycoproteins that generally promote cell adhesion through homophilic interactions (a CAD on the surface of one cell binds to an identical CAD on the surface of another cell), although CADs also appear to be capable of forming heterotypic complexes with one another under certain circumstances and with lower affinity. Cadherins have been shown to regulate epithelial, endothelial, neural and cancer cell adhesion, with different CADs expressed on different cell types. N (neural) - cadherin is predominantly expressed by neural cells, endotbelial cells and a variety of cancer cell types. E (epithelial) - cadherin is predominantly expressed by epithelial cells. Other CADs are P (placental) - cadherin, which is found in human skin and R (retinal) - cadherin. A detailed discussion of the classical cadherins is provided in Munro SB et al., 1996, *In: Cell Adhesion and Invasion in Cancer Metastasis*, P. Brodt, ed., pp.17–34 (RG Landes Company, Austin Tex.).

The structures of the CADs are generally similar. As illustrated in FIG. 1, CADs are composed of five extracellular domains (EC1–EC5), a single hydrophobic domain (TM) that transverses the plasma membrane (PM), and two cytoplasmic domains (CP1 and CP2). The calcium binding motifs DXNDN (SEQ ID NO:1), DXD and LDRE (SEQ ID NO:2) are interspersed throughout the extracellular domains. The first extracellular domain (EC1) contains the classical cadherin cell adhesion recognition (CAR) sequence, HAV (His-Ala-Val), along with flanking sequences on either side of the CAR sequence that may play a role in conferring specificity. Synthetic peptides containing the CAR sequence and antibodies directed against the CAR sequence have been shown to inhibit CAD-dependent processes (Munro et al., supra; Blaschuk et al., *J. Mol. Biol.* 211:679–82, 1990; Blaschuk et al., *Develop. Biol.* 139:227–29, 1990; Alexander et al., *J. Cell. Physiol.* 156:610–18, 1993). However, the determination of the three-dimensional solution and crystal structures of the EC1 domain of classical cadherins (Overduin et al., *Science* 267:386–389, 1995; Shapiro et al., *Nature* 374:327–337, 1995) suggest that amino acid residues other than HAV may be directly involved in mediating the interactions between cadherins.

Although cell adhesion is required for certain normal physiological functions, there are situations in which the level of cell adhesion is undesirable. For example, many pathologies (such as autoimmune diseases, cancer and inflammatory diseases) involve abnormal cellular adhesion. Cell adhesion may also play a role in graft rejection. In such circumstances, modulation of cell adhesion may be desirable.

In addition, permeability barriers arising from cell adhesion create difficulties for the delivery of drugs to specific tissues and tumors within the body. For example, skin patches are a convenient tool for administering drugs through the skin. However, the use of skin patches has been limited to small, hydrophobic molecules because of the epithelial and endothelial cell barriers. Similarly, endothelial cells render the blood capillaries largely impermeable to drugs, and the blood/brain barrier has hampered the targeting of drugs to the central nervous system. In addition, many solid tumors develop internal barriers that limit the delivery of anti-tumor drugs and antibodies to inner cells.

Attempts to facilitate the passage of drugs across such barriers generally rely on specific receptors or carrier proteins that transport molecules across barriers in vivo. However, such methods are often inefficient, due to low endogenous transport rates or to the poor functioning of a carrier protein with drugs. While improved efficiency has been achieved using a variety of chemical agents that disrupt cell adhesion, such agents are typically associated with undesirable side-effects, may require invasive procedures for administration and may result in irreversible effects.

Accordingly, there is a need in the art for compounds that modulate cell adhesion and improve drug delivery across permeability barriers without such disadvantages. The present invention fulfills this need and further provides other related advantages.

SUMMARY OF THE INVENTION

The present invention provides compositions and methods for modulating cadherin-mediated functions. Within certain aspects, the present invention provides cell adhesion modulating agents capable of binding to the cadherin CAR sequence HAV, wherein the agent does not comprise an antibody or antigen-binding fragment thereof.

Within related aspects, the present invention provides cell adhesion modulating agents, comprising: (a) an HAV-BM sequence or peptidomimetic thereof; (b) a polynucleotide encoding an HAV-BM sequence; or (c) an antibody or antigen-binding fragment thereof that specifically binds to an HAV-BM sequence; wherein the agent modulates a cadherin-mediated process. Within certain specific embodiments, the HAV-BM sequence is: (a) Ile/Val-Phe-Aaa-Ile-Baa-Caa-Daa-Ser/Thr-Gly-Eaa-Leu/Met (SEQ ID NO:3), wherein Aaa, Baa, Caa, Daa and Eaa are independently selected from the group consisting of amino acid residues; (b) Trp-Leu-Aaa-Ile-Asp/Asn-Baa-Caa-Daa-Gly-Gln-Ile (SEQ ID NO:4), wherein Aaa, Baa, Caa and Daa are independently selected from the group consisting of amino acid residues; or (c) an analogue of any of the foregoing sequences that retains at least seven consecutive amino acid residues, wherein the ability of the analogue to modulate a cadherin-mediated process is not diminished. For example, a cell adhesion modulating agent may comprise an HAV-BM sequence is selected from the group consisting of: IFIINPISGQL (SEQ ID NO:5), IFILNPISGQL (SEQ ID NO:6), VFAVEKETGWL (SEQ ID NO:7), VFSINSMSGRM (SEQ ID NO:8), VFIIERETGWL (SEQ ID NO:9), VFTIEKESGWL (SEQ ID NO:10), VFNIDSMSGRM (SEQ ID NO:11), WLKIDSVNGQI (SEQ ID NO:12), WLKIDPVNGQI (SEQ ID NO: 13), WLAMDPDSGQV (SEQ ID NO:14), WLHINATNGQI (SEQ ID NO:15), WLEINPDTGAI (SEQ ID NO:16), WLAVDPDSGQI (SEQ ID NO:17), WLEINPETGAI (SEQ ID NO:18), WLHINTSNGQI (SEQ ID NO:19), NLKIDPVNGQI (SEQ ID NO:20), LKIDPVNGQI (SEQ ID NO:21) and analogues of the foregoing sequences that retain at least seven consecutive residues (e.g., INPISGQ (SEQ ID NO:22), LNPISGQ (SEQ ID NO:23), IDPVSGQ (SEQ ID NO:24) or KIDPVNGQ (SEQ ID NO:25)), wherein the ability of the analogue to modulate a cadherin-mediated process is not diminished. Alternatively, a modulating agent may comprise an HAV-BM sequence that comprises at least five consecutive residues of a peptide selected from the group consisting of INPISGQ (SEQ ID NO:22), LNPISGQ (SEQ ID NO:23), NLKIDPVNGQI (SEQ ID NO:20) and WLKIDPVNGQI (SEQ ID NO:13). For example, the agent may comprise a sequence selected from the group consisting of PISGQ (SEQ ID NO:26), PVNGQ (SEQ ID NO:27), PVSGR (SEQ ID NO:28), IDPVN (SEQ ID NO:29), INPIS (SEQ ID NO:30) and KIDPV (SEQ ID NO:31). Within such modulating agents, an HAV-BM sequence may be present within a linear peptide or a cyclic peptide. Certain modulating agents comprise a cyclic peptide having one of the formulas:

$$(Z_1)-(Y_1)-(X_1)-PISGQ-(X_2)-(Y_2)-(Z_2); \quad (i)$$

$$(Z_1)-(Y_1)-(X_1)-PVNGQ-(X_2)-(Y_2)-(Z_2); \quad (ii)$$

$$(Z_1)-(Y_1)-(X_1)-PVSGR-(X_2)-(Y_2)-(Z_2); \quad (iii)$$

$$(Z_1)-(Y_1)-(X_1)-IDPVN-(X_2)-(Y_2)-(Z_2); \quad (iv)$$

$$(Z_1)-(Y_1)-(X_1)-INPIS-(X_2)-(Y_2)-(Z_2); \text{ or} \quad (v)$$

$$(Z_1)-(Y_1)-(X_1)-KIDPV-(X_2)-(Y_2)-(Z_2) \quad (vi)$$

wherein $X_1$, and $X_2$ are optional, and if present, are independently selected from the group consisting of amino acid residues and combinations thereof in which the residues are linked by peptide bonds, and wherein $X_1$ and $X_2$ independently range in size from 0 to 10 residues, such that the sum of residues contained within $X_1$ and $X_2$ ranges from 1 to 12; wherein $Y_1$ and $Y_2$ are independently selected from the group consisting of amino acid residues, and wherein a covalent bond is formed between residues $Y_1$ and $Y_2$; and wherein $Z_1$ and $Z_2$ are optional, and if present, are independently selected from the group consisting of amino acid residues and combinations thereof in which the residues are linked by peptide bonds. Such cyclic peptides may contain modifications. For example, $Y_1$ may comprise an N-acetyl group and/or $Y_2$ may comprise a C-terminal amide group. Cyclization may be achieved in any of a variety of ways, such as covalent linkage of $Y_1$ and $Y_2$ via a disulfide, amide or thioether bond.

Within certain embodiments, modulating agents as described above may be linked to one or more of a drug, a solid support, a detectable marker or a targeting agent.

Within other embodiments, a modulating agents as described above may further comprise one or more of: (a) a cell adhesion recognition sequence other than an HAV-BM sequence, wherein the cell adhesion recognition sequence is separated from any HAV-BM sequence(s) by a linker; and/or (b) an antibody or antigen-binding fragment thereof that specifically binds to a cell adhesion recognition sequence other than an HAV-BM sequence. For example, the adhesion molecule may be selected from the group consisting of cadherins, integrins, occludin, N-CAM, desmogleins, desmocollins, fibronectin, laminin and other extracellular matrix proteins.

Within further aspects, the present invention provides pharmaceutical compositions comprising a cell adhesion modulating agent as described above, in combination with a pharmaceutically acceptable carrier. Such compositions may further comprise one or more of a drug and/or a modulator of cell adhesion, wherein the modulator comprises one or more of: (a) a peptide comprising a cell adhesion recognition sequence other than an HAV-BM sequence; and/or (b) an antibody or antigen-binding fragment thereof that specifically binds to a cell adhesion recognition sequence other than an HAV-BM sequence. For example, the adhesion molecule may be selected from the group consisting of cadherins, integrins, occludin, N-CAM, desmogleins, desmocollins, fibronectin, laminin and other extracellular matrix proteins.

The present invention further provides, within other aspects, methods for modulating a cadherin-mediated function, comprising contacting a cadherin-expressing cell with a cell adhesion modulating agent as described above. Cadherin-mediated functions include cell adhesion, neurite outgrowth, Schwann cell migration and synaptic stability. Cadherin-expressing cells include epithelial cells, endothelial cells, neural cells, tumor cells and lymphocytes. Within such aspects, the cell adhesion modulating agent may inhibit or enhance a cadherin-mediated function.

Within other aspects, the present invention provides methods for reducing unwanted cellular adhesion in a mammal, comprising administering to a mammal a modulating agent as described above, wherein the modulating agent inhibits cadherin-mediated cell adhesion. The cell may be selected from the group consisting of epithelial cells, endothelial cells, neural cells, tumor cells and lymphocytes.

The present invention further provides, within other aspects, methods for enhancing the delivery of a drug through the skin of a mammal, comprising contacting epithelial cells of a mammal with a drug and a modulating agent as described above, wherein the step of contacting is performed under conditions and for a time sufficient to allow passage of the drug across the epithelial cells, and wherein the modulating agent inhibits cadherin-mediated cell adhesion. The modulating agent may, but need not, be linked to the drug and may, within certain embodiments, pass into the blood stream of the mammal. The step of contacting may be performed via a skin patch comprising the modulating agent and the drug.

Within further aspects, methods are provided for enhancing the delivery of a drug to a tumor in a mammal, comprising administering to a mammal a modulating agent as described above, wherein the modulating agent inhibits cadherin-mediated cell adhesion. Suitable tumors include, but are not limited to, bladder tumors, ovarian tumors and melanomas, and the modulating agent may be administered to the tumor or systemically.

Within other aspects, the present invention provides methods for treating cancer and/or inhibiting metastasis in a mammal, comprising administering to a mammal a modulating agent as described above, wherein the modulating agent inhibits cadherin-mediated cell adhesion. The mammal may be afflicted with a cancer such as a carcinoma, leukemia or melanoma, and the modulating agent may be administered to the tumor or systemically.

The present invention further provides, within other aspects, methods for inducing apoptosis in a cadherin-expressing cell, comprising contacting a cadherin-expressing cell with a modulating agent as described above, wherein the modulating agent inhibits cadherin-mediated cell adhesion.

Within other aspects, methods are provided for inhibiting angiogenesis in a mammal, comprising administering to a mammal a modulating agent as described above, wherein the modulating agent inhibits cadherin-mediated cell adhesion.

The present invention further provides, within other aspects, methods for enhancing drug delivery to the central nervous system of a mammal, comprising administering to a mammal a modulating agent as described above, wherein the modulating agent inhibits cadherin-mediated cell adhesion.

Within further aspects, the present invention provides methods for facilitating wound healing in a mammal, comprising contacting a wound in a mammal with a modulating agent as described above, wherein the modulating agent enhances cadherin-mediated cell adhesion.

Methods are also provided, within other aspects, for enhancing adhesion of foreign tissue implanted within a mammal, comprising contacting a site of implantation of foreign tissue in a mammal with a modulating agent as described above, wherein the modulating agent enhances cadherin-mediated cell adhesion. Such foreign tissue may be a skin graft or organ implant. Within certain embodiments, the modulating agent is linked to a support material.

The present invention further provides, in other aspects, methods for enhancing and/or directing neurite outgrowth, comprising contacting a neuron with a modulating agent as described above, wherein the modulating agent enhances cadherin-mediated cell adhesion.

Within other aspects, the present invention provides methods for treating spinal cord injuries in a mammal, comprising administering to a mammal a modulating agent as described above, wherein the modulating agent enhances cadherin-mediated cell adhesion.

Methods are also provided, within further aspects, for treating a demyelinating neurological disease such as multiple sclerosis in a mammal, comprising administering to a mammal a modulating agent as described above. Within certain embodiments, the modulating agent is administered by implantation with Schwann cells, oligodendrocyte progenitor cells and/or oligodendrocytes.

Within further aspects, methods are provided for modulating the immune system of a mammal, comprising administering to a mammal a modulating agent as described above, wherein the modulating agent inhibits cadherin-mediated cell adhesion.

Within other aspects, the present invention provides methods for preventing pregnancy in a mammal, comprising administering to a mammal a modulating agent as described above, wherein the modulating agent inhibits cadherin-mediated cell adhesion.

Methods are further provided for increasing vasopermeability in a mammal, comprising administering to a mammal a modulating agent as described above, wherein the modulating agent inhibits cadherin-mediated cell adhesion.

Within further aspects, the present invention provides methods for inhibiting synaptic stability in a mammal, comprising administering to a mammal a modulating agent as described above, wherein the modulating agent inhibits cadherin-mediated cell adhesion.

The present invention further provides methods for detecting the presence of cadherin-expressing cells in a sample, comprising: (a) contacting a sample with an antibody or antigen-binding fragment thereof that binds to an HAV-BM sequence under conditions and for a time sufficient to allow formation of an antibody-cadherin complex; and (b) detecting the level of antibody-cadherin complex, and therefrom detecting the presence of cadherin expressing cells in a sample. The antibody may be linked to a support material or a detectable marker such as a fluorescent marker. In certain embodiments, the step of detecting is performed using fluorescence activated cell sorting.

The present invention also provides, within further aspects, kits for enhancing transdermal drug delivery, comprising: (a) a skin patch; and (b) a modulating agent as described above. The skin patch may be impregnated with the modulating agent, and the kit may further comprise a drug.

Kits for detecting the presence of cadherin-expressing cells in a sample are also provided. Such kits may comprise: (a) an antibody or antigen-binding fragment thereof that specifically binds to an HAV-BM sequence; and (b) a detection reagent.

Within other aspects, the present invention provides methods for identifying a compound capable of modulating cadherin-mediated cell adhesion, comprising: (a) contacting an antibody or antigen-binding fragment thereof that specifically binds to an HAV-BM sequence with a test compound; and (b) detecting the level of antibody or fragment that binds to the test compound, and therefrom identifying a compound capable of modulating cadherin-mediated cell adhesion.

Methods are also provided, within other aspects, for facilitating blood sampling in a mammal, comprising contacting epithelial cells of a mammal with a cell adhesion modulating agent as described above, wherein the modulating agent inhibits cadherin-mediated cell adhesion, and wherein the step of contacting is performed under conditions and for a time sufficient to allow passage of one or more blood components across the epithelial cells. The step of contacting may be performed via a skin patch comprising the modulating agent, and the skin patch may further comprise a reagent for detecting a blood component of interest. Within certain embodiments, the epithelial cells are skin cells or gum cells.

Within related aspects, the present invention provides kits for sampling blood via the skin or gum of a mammal, comprising: (a) a skin patch; (b) a cell adhesion modulating agent comprising a cyclic peptide that comprises a cadherin CAR sequence; and (c) a reagent for detecting a blood component of interest. The skin patch may be impregnated with the cell adhesion modulating agent.

Within other aspects, the present invention provides methods for screening for a compound that interacts with an HAV-BM sequence, comprising the steps of: (a) contacting a candidate compound with an HAV-BM sequence; and (b) evaluating the ability of the candidate compound to bind to the HAV-BM sequence, and therefrom determining whether the candidate compound interacts with an HAV-BM sequence. Within certain embodiments, the ability of the candidate compound to bind to the HAV-BM sequence is evaluated using an affinity column or a Western blot analysis. Within certain embodiments, the candidate compound is encoded by a polynucleotide in an expression library, or the candidate compound is a cellular protein, and step (b) is performed using whole cells.

These and other aspects of the invention will become evident upon reference to the following detailed description and attached drawings. All references disclosed herein are hereby incorporated by reference in their entirety as if each were individually noted for incorporation.

BRIEF DESCRIPTION OF THE DRAWINGS

FIG. 2 provides the amino acid sequences of mammalian classical cadherin EC1 domains: human N-cadherin (SEQ ID NO:32), mouse N-cadherin (SEQ ID NO:33), cow N-cadherin (SEQ ID NO:34), human E-cadherin (SEQ ID NO:35), mouse E-cadherin (SEQ ID NO:36), human P-cadherin (SEQ ID NO:37), mouse P-cadherin (SEQ ID NO:38), human R-cadherin (SEQ ID NO:39) and mouse R-cadherin (SEQ ID NO:40).

FIG. 3 provides the amino acid sequences of mammalian classical cadherin EC4 domains: human N-cadherin (SEQ ID NO:41), mouse N-cadherin (SEQ ID NO:42), cow N-cadherin (SEQ ID NO:43), human E-cadherin (SEQ ID NO:44), mouse E-cadherin (SEQ ID NO:45), human P-cadherin (SEQ ID NO:46), mouse P-cadherin (SEQ ID NO:47), human R-cadherin (SEQ ID NO:48) and mouse R-cadherin (SEQ ID NO:49).

FIGS. 4A–4D provide structures of representative cyclic peptide modulating agents (SEQ ID NOs: 51–63 and 85).

FIG. 8B shows the cells 24 hours after being cultured in the presence of 1 mg/mL of N-Ac-INPISGQ (SEQ ID NO:22).

DETAILED DESCRIPTION OF THE INVENTION

Figure 1:
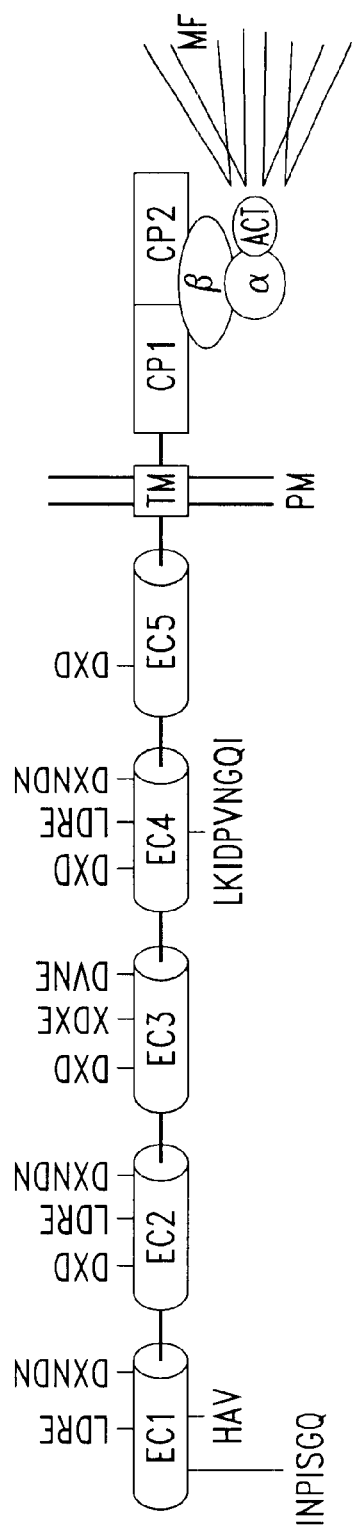
FIG. 1 is a diagram depicting the structure of classical CADs. The five extracellular domains are designated EC1–EC5, the hydrophobic domain that transverses the plasma membrane (PM) is represented by TM, and the two cytoplasmic domains are represented by CP1 and CP2. The calcium binding motifs are shown by DXNDN (SEQ ID NO:1), DXD XDXE (SEQ ID NO:86), DVNE (SEQ ID NO:87) and LDRE (SEQ ID NO:2). The CAR sequence, HAV, is shown within EC1. The sequences, INPISGQ (SEQ ID NO:22) and LKIDPVNGQI (SEQ ID NO:21) are shown within EC1 and EC4, respectively. Cytoplasmic proteins β-catenin (β), α-catenin (α) and α-actinin (ACT), which mediate the interaction between CADs and microfilaments (MF) are also shown.

As noted above, the present invention provides methods for modulating cadherin-mediated processes, such as cell adhesion. The present invention is based upon the identification of a previously unknown cell adhesion recognition (CAR) sequence in classical cadherins. This CAR sequence is referred to herein as the "HAV binding motif" (or "HAV-BM"). The HAV-BM appears to interact directly with the HAV CAR sequence and/or flanking regions in homophilic and heterophilic interactions.

In general, to modulate cadherin-mediated cell adhesion, a cell that expresses a classical cadherin is contacted with a cell adhesion modulating agent (also referred to herein as a "modulating agent") either in vivo or in vitro. A modulating agent may comprise one or more HAV-BM sequences (which may be native sequences or analogues thereof) or a peptidomimetic of such a sequence, with or without one or more additional CAR sequences (which may be derived from classical cadherins or from other adhesion molecules), as described below. HAV-BM sequences may be present within a linear or cyclic peptide. Alternatively, or in addition, a modulating agent may comprise a polynucleotide encoding a peptide comprising one or more HAV-BM sequences (such that the encoded peptide is produced in vivo) and/or a substance (such as an antibody or antigen-binding fragment thereof) that specifically binds an HAV-BM sequence.

Certain methods provided herein employ cell adhesion modulating agents for inhibiting or enhancing cadherin-mediated cell adhesion. Inhibition of cell adhesion may generally be used, for example, to treat diseases or other conditions characterized by undesirable cell adhesion or to facilitate drug delivery to a specific tissue or tumor. Within other aspects, the methods provided herein may be used to enhance cell adhesion (e.g., to supplement or replace stitches or to facilitate wound healing). Within still further aspects, methods are provided for enhancing and/or directing neurite outgrowth.

CELL ADHESION MODULATING AGENTS

As noted above, the term "cell adhesion modulating agent," as used herein, generally refers to a compound that is capable of binding to a classical cadherin (i.e., the compound interacts detectably with one or more amino acid residues within a classical cadherin such that a cadherin-mediated process is modulated, as described herein). Preferably, a modulating agent binds in or near a classical cadherin CAR sequence HAV (i.e., the agent interacts detectably with one or more amino acid residues present within the HAV sequence and/or one or more amino acid residues present within ten amino acid residues, and more preferably within five amino acid residues, of the HAV sequence in a native cadherin). Within specific embodiments, a modulating agent comprises at least one of the following:

(a) an HAV-BM sequence (i.e., a native HAV-BM sequence or an analogue thereof), or a peptidomimetic thereof;

(b) a polynucleotide encoding an HAV-BM sequence; or (c) an antibody or antigen-binding fragment thereof that specifically binds to an HAV-BM sequence.

A modulating agent may consist entirely of an HAV-BM sequence (within a linear or cyclic peptide), peptidomimetic, polynucleotide or antibody, or may additionally comprise further peptide and/or non-peptide regions.

An "HAV-BM sequence" is an HAV-binding sequence that exists in a naturally occurring cadherin, or an analogue of such a sequence in which the ability to modulate a cadherin-mediated process is not diminished. Such sequences generally comprise at least five amino acid residues, preferably 6–16 amino acid residues, and may be identified based on sequence homology to known HAV-BM sequences, which are provided herein, and based on the ability of a peptide comprising such a sequence to bind to an HAV sequence and modulate a cadherin-mediated function, within a representative assay as described herein. Within certain embodiments, the HAV-BM sequence is:

(a) Ile/Val-Phe-Aaa-Ile-Baa-Caa-Daa-Ser/Thr-Gly-Eaa-Leu/Met (SEQ ID NO:3), wherein Aaa, Baa, Caa, Daa and Eaa are independently selected from the group consisting of amino acid residues;

(b) Trp-Leu-Aaa-Ile-Asp/Asn-Baa-Caa-Daa-Gly-Gln-Ile (SEQ ID NO:4), wherein Aaa, Baa, Caa and Daa are independently selected from the group consisting of amino acid residues; or (c) an analogue of any of the foregoing sequences that retains at least seven consecutive amino acid residues.

Representative known HAV-BM sequences are provided in Table I. These sequences are not intended to limit the scope of HAV-BM sequences encompassed by the present invention. In particular, a modulating agent may comprise a portion or other analogue of such sequences, provided that the ability of the analogue to modulate a cadherin-mediated function is not substantially diminished.

TABLE I

Representative HAV-BM Sequences

| Cadherin | HAV-BM |
|---|---|
| EC1 Domains | |
| BTCADHN | IFIINPISGQL (SEQ ID NO: 5) |
| HSNCADHER | IFILNPISGQL (SEQ ID NO: 6) |
| HSPCAD | VFAVBKETGWL (SEQ ID NO: 7) |
| HUMCA4A | VFSINSNSGRM (SEQ ID NO: 8) |
| HUMUVOECAD | VFIIERETGWL (SEQ ID NO: 9) |
| MMCADHP | VFTIEKESGWL (SEQ ID NO: 10) |
| MMECADH | VFIIERETGWL (SEQ ID NO: 9) |
| MMRCADA | VFNIDSNSGRM (SEQ ID NO: 11) |
| MUSCADNA | IEIINPISGQL (SEQ ID NO: 5) |
| CONSENSUS | IFXIXXXSGXL (SEQ ID NO: 3)<br>V    T    M |
| EC4 Domains | |
| BTCADHN | WLKIDSVNGQI (SEQ ID NO: 12) |
| HSNCADHER | WLYIDPVNGQI (SEQ ID NO: 13) |
| HSPCAD | WLAMDPDSGQV (SEQ ID NO: 14) |
| HUMCA4A | WLHINATNGQI (SEQ ID NO: 15) |
| HUMUVOECAD | WLEINPDTGAI (SEQ TD NO: 16) |
| MMCADHP | WLAVDPDSGQI (SEQ ID NO: 17) |
| MMECADH | WLEINPETGAI (SEQ ID NO: 18) |
| MMRCADA | WLHINTSNGQI (SEQ ID NO: 19) |
| MUSCADNA | WLKIDPVNGQI (SEQ ID NO: 13) |
| CONSENSUS | WLXIDXXXGQI (SEQ ID NO: 4)<br>N |

Within certain specific embodiments, the HAV-BM sequence comprises INPISGQ (SEQ ID NO:22), LNPISGQ (SEQ ID NO:23), IDPVSGQ (SEQ ID NO:24) or KIDPVNGQ (SEQ ID NO:25). For example, HAV-BM sequences include, but are not limited to N-Ac-NLKIDPVNGQI-NH$_2$ (SEQ ID NO:20) and H-LKIDPVNGQI-OH (SEQ ID NO:21).

Within other embodiments, an HAV-BM sequence may comprise at least five consecutive residues of one of the following peptides: INPISGQ (SEQ ID NO:22), LNPISGQ (SEQ ID NO:23), NLKIDPVNGQI (SEQ ID NO:20) and WLKIDPVNGQI (SEQ ID NO: 13). For example, a modulating agent may comprise the sequence PISGQ (SEQ ID NO:26), PVNGQ (SEQ ID NO:27), PVSGR (SEQ ID NO:28), KIDPV (SEQ ID NO:31), IDPVN (SEQ ID NO:29), INPIS (SEQ ID NO:30) or KIDPVN (SEQ ID NO:50) As noted above, within any of the above embodiments, an HAV-BM sequence may be present within a cyclic peptide, such as <u>PVNGQ</u> (SEQ ID NO:51), <u>PISGQ</u> (SEQ ID NO:52), <u>PVSGR</u> (SEQ ID NO:53), <u>KIDPV</u> (SEQ ID NO:54), <u>KIDPVN</u> (SEQ ID NO:55), <u>IDPVN</u> (SEQ ID NO:56), <u>INPIS</u> (SEQ ID NO:57), <u>CPVNGQC</u> (SEQ ID NO:58), <u>CPISGQC</u> (SEQ ID NO:59), <u>CPVSGRC</u> (SEQ ID NO:60), <u>CKIDPVNC</u> (SEQ ID NO:61), <u>CIDPVNC</u> (SEQ ID NO:62), <u>CINPISC</u> (SEQ ID NO:63) or <u>CKIDPVC</u> (SEQ ID NO:85), in which cyclization is indicated by the underline.

Other HAV-BM sequences include sequences in which a native sequence is modified. For example, the peptides H-LKIDPANGQI-OH (SEQ ID NO:64) and H-LKIDAVNGQI-OH (SEQ ID NO:65) comprise HAV-BM sequences.

As noted above, the present invention further contemplates native HAV-BM sequences from other cadherins not specifically recited herein. Additional native HAV-BM sequences may be identified based upon sequence similarity to one or more of the native HAV-BMs provided herein. In general, a native HAV-BM sequence should retain at least three amino acid residues of a native HAV-BM provided herein, and a total of at least seven amino acid residues should be identical or contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity on polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. The critical determining features of a native HAV-BM are the ability to bind to an HAV sequence and the ability to modulate a cadherin-mediated function. Such abilities may be evaluated using the representative assays provided herein.

As noted above, modulating agents as described herein may comprise a native HAV-BM sequence, or an analogue or peptidomimetic thereof. An analogue generally retains at least three amino acid residues of a native HAV-BM, and binds to an HAV sequence and modulates a cadherin-mediated function as described below. In particular, an analogue should bind to a classical cadherin and modulate a cadherin-mediated function at least as well as a native HAV-BM sequence within at least one of the assays provided herein. A peptidomimetic is a non-peptide compound that is structurally similar to an HAV-BM sequence, such that it binds to HAV sequences and modulates a cadherin-mediated function as described below. Such peptidomimetics may be designed based on techniques that evaluate the three dimensional structure of a peptide. For example, nuclear magnetic resonance (NMR) and computational techniques may be used to determine the conformation of an HAV-BM sequence. NMR is widely used for structural analyses of both peptidyl and non-peptidyl compounds. Nuclear Overhauser Enhancements (NOE's), coupling constants and chemical shifts depend on the conformation of a compound. NOE data provides the interproton distance between protons through space and can be used to calculate of the lowest energy conformation for the HAV-BM sequence. This information can then be used to design peptidomimetics of the preferred conformation. Linear peptides in solution exist in many conformations. By using conformational restriction techniques it is possible to fix the peptide in the active conformation. Conformational restriction can be achieved by i) introduction of an alkyl group such as a methyl which sterically restricts free bond rotation; ii) introduction of unsaturation which fixes the relative positions of the terminal and geminal substituents; and/or iii) cyclization, which fixes the relative positions of the sidechains. Peptidomimetics of an HAV-BM sequence may be synthesized where one or more of the amide linkages has been replaced by isosteres, substituents or groups which have the same size or volume such as, but not limited to, —CH$_2$NH—, —CSNH—, —CH$_2$S—, —CH=CH—, —CH$_2$CH$_2$—, —CONMe— and others. These backbone amide linkages can be also be part of a ring structure (i.e., lactam). Peptidomimetics of an HAV-BM sequence may be designed where one or more of the side chain functionalities of the HAV-BM sequence can be replaced by groups that do not necessarily have the same size or volume, but have similar chemical and/or physical properties which produce similar biological responses. It should be understood that, within embodiments described below, an analogue or peptidomimetic may be substituted for an HAV-BM sequence.

Modulating agents, or peptide portions thereof, may generally comprise from 5 to about 1000 amino acid residues, preferably from 6 to 50 residues. When non-peptide linkers are employed, each CAR sequence of the modulating agent is present within a peptide that generally ranges in size from 5 to 50 residues in length, preferably from 5 to 25 residues, more preferably from 5 to 16 residues and still more preferably from 5 or 6 to 10 residues.

Modulating agents, or peptide portions thereof, may be linear or cyclic peptides. The term "cyclic peptide," as used herein, refers to a peptide or salt thereof that comprises (1) an intramolecular covalent bond between two non-adjacent residues and (2) at least one HAV-BM sequence or an analogue thereof present within the peptide ring. The intramolecular bond may be a backbone to backbone, side-chain to backbone or side-chain to side-chain bond (i.e., terminal functional groups of a linear peptide and/or side chain functional groups of a terminal or interior residue may be linked to achieve cyclization). Preferred intramolecular bonds include, but are not limited to, disulfide, amide and thioether bonds. As noted above, in addition to one or more HAV-BM sequence or analogue thereof, a modulating agent may comprise additional CAR sequences, which may or may not be cadherin CAR sequences, and/or antibodies or fragments thereof that specifically recognize a CAR sequence. Antibodies and antigen-binding fragments thereof are typically present in a non-cyclic portion of a modulating agent.

The size of a cyclic peptide ring generally ranges from 4 to about 15 residues, preferably from 5 to 10 residues. Additional residue(s) may be present on the N-terminal and/or C-terminal side of an HAV-BM sequence, and may be derived from sequences that flank a native HAV-BM sequence, with or without amino acid substitutions and/or other modifications. Additional residue(s) that may be present on the N-terminal and/or C-terminal side of an HAV-BM sequence may be derived from sequences that flank the HAV-BM sequence within one or more naturally occurring cadherins, with or without amino acid substitutions and/or other modifications. Flanking sequences for endogenous N-, E-, P- and R-cadherin HAV-BMs are shown in FIGS. 2 and 3, and SEQ ID NOs: 32 to 49. Alternatively, additional residues present on one or both sides of the CAR sequence(s) may be unrelated to an endogenous sequence (e.g., residues that facilitate cyclization, purification or other manipulation and/or residues having a targeting or other function).

In certain preferred embodiments, a modulating agent comprises a cyclic peptide having one of the following structures:

(i)
$(Z_1)$—$(Y_1)$—$(X_1)$—PISGQ—$(X_2)$—$(Y_2)$—$(Z_2)$;

(ii)
$(Z_1)$—$(Y_1)$—$(X_1)$—PVNGQ—$(X_2)$—$(Y_2)$—$(Z_2)$;

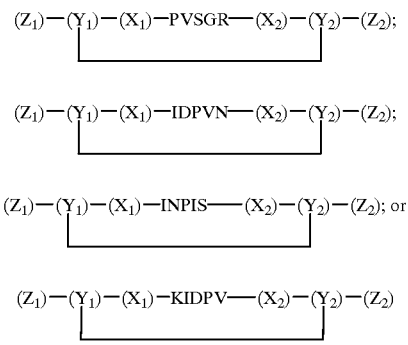

-continued (iii)

$(Z_1)-(Y_1)-(X_1)-PVSGR-(X_2)-(Y_2)-(Z_2)$;

(iv)

$(Z_1)-(Y_1)-(X_1)-IDPVN-(X_2)-(Y_2)-(Z_2)$;

(v)

$(Z_1)-(Y_1)-(X_1)-INPIS-(X_2)-(Y_2)-(Z_2)$; or (vi)

$(Z_1)-(Y_1)-(X_1)-KIDPV-(X_2)-(Y_2)-(Z_2)$

In these structures, $X_1$, and $X_2$ are optional, and if present, are independently selected amino acid residues and combinations thereof in which the residues are linked by peptide bonds. In general, $X_1$ and $X_2$ independently range in size from 0 to 10 residues, such that the sum of residues contained within $X_1$ and $X_2$ ranges from 1 to 12. $Y_1$ and $Y_2$ are independently selected amino acid residues, and a covalent bond is formed between residues $Y_1$ and $Y_2$. $Z_1$ and $Z_2$ are optional, and if present, are independently selected amino acid residues and combinations thereof in which the residues are linked by peptide bonds. Representative examples of such structures are provided in FIGS. 4A–4D.

A modulating agent that contains sequences that flank the HAV-BM sequence on one or both sides may be specific for cell adhesion mediated by one or more specific cadherins, resulting in tissue and/or cell-type specificity. Suitable flanking sequences for conferring specificity include, but are not limited to, endogenous sequences present in one or more naturally occurring cadherins. Modulating agents having a desired specificity may be identified using the representative screens provided herein.

As noted above, multiple CAR sequences may be present within a modulating agent. The total number of CAR sequences present within a modulating agent may range from 1 to a large number, such as 100, preferably from 1 to 10, and more preferably from 1 to 5. CAR sequences that may be included within a modulating agent are any sequences specifically bound by an adhesion molecule (i.e., a molecule that mediates cell adhesion via a receptor on the cell's surface). Adhesion molecules include members of the cadherin gene superfamily that are not classical cadherins (e.g., proteins that do not contain an HAV sequence and/or one or more of the other characteristics recited above for classical cadherins), such as desmogleins (Dsg) and desmocollins (Dsc); integrins; members of the immunoglobulin supergene family, such as N-CAM; and other uncategorized transmembrane proteins, such as occludin, as well as extracellular matrix proteins such as laminin, fibronectin, collagens, vitronectin, entactin and tenascin. Within certain embodiments, preferred CAR sequences for inclusion within a modulating agent include Arg-Gly-Asp (RGD), which is bound by integrins (see Cardarelli et al., *J. Biol. Chem.* 267:23159–64, 1992); Tyr-Ile-Gly-Ser-Arg (YIGSR; SEQ ID NO:66), which is bound by α6β1 integrin; KYSFNYDGSE (SEQ ID NO:67), which is bound by N-CAM; the N-CAM heparin sulfate-binding site IWKHKGRDVILKKDVRF (SEQ ID NO:68), the putative Dsc CAR sequences YAT, FAT and YAS; the putative Dsg CAR sequence RAL; and/or the occludin CAR sequence GVNPTAQSSGSLYGSQIYALCNQFYTPAATGLY VDQYLYHYCVVDPQE (SEQ ID NO:69), or derivatives or portions thereof such as LYHY (SEQ ID NO:70).

Within certain embodiments, another preferred CAR sequence is the OB-cadherin CAR sequence DDK. A variety of peptides comprising this sequence may be included, such as IDDK (SEQ ID NO:71), DDKS (SEQ ID NO:72), VIDDK (SEQ ID NO:73), IDDKS (SEQ ID NO:74), VIDDKS (SEQ ID NO:75), DDKSG (SEQ ID NO:76), IDDKSG (SEQ ID NO:77), VIDDKSG (SEQ ID NO:78), FVIDDK (SEQ ID NO:79), FVIDDKS (SEQ ID NO:80), FVIDDKSG (SEQ ID NO:81), IFVIDDK (SEQ ID NO:82), IFVIDDKS (SEQ ID NO:83), or IFVIDDKSG (SEQ ID NO:84). In certain preferred embodiments, at least one terminal amino acid residue of such a peptide is modified (e.g, the N-terminal amino group is modified by, for example, acetylation or alkoxybenzylation and/or an amide or ester is formed at the C-terminus). Certain preferred modulating agents contain modifications at the N- and C-terminal residues, such as N-Ac-IFVIDDKSG-$NH_2$ (SEQ ID NO:84). Analogues of any of the foregoing sequences may also be used. An analogue generally retains at least 50% of a native OB-cadherin CAR sequence, and modulates OB-cadherin-mediated cell adhesion.

Linkers may, but need not, be used to separate CAR sequences and/or antibody sequences within a modulating agent. Linkers may also, or alternatively, be used to attach one or more modulating agents to a support molecule or material, as described below. A linker may be any molecule (including peptide and/or non-peptide sequences as well as single amino acids or other molecules), that does not contain a CAR sequence and that can be covalently linked to at least two peptide sequences. Using a linker, HAV-BM-containing peptides and other peptide or protein sequences may be joined head-to-tail (i.e., the linker may be covalently attached to the carboxyl or amino group of each peptide sequence), head-to-side chain and/or tail-to-side chain. Modulating agents comprising one or more linkers may form linear or branched structures. Within one embodiment, modulating agents having a branched structure comprise three different CAR sequences, such as RGD, YIGSR (SEQ ID NO:66) and an HAV-BM sequence. Within another embodiment, modulating agents having a branched structure may comprise RGD, YIGSR (SEQ ID NO:66), an HAV-BM sequence and KYSFNYDGSE (SEQ ID NO:67). In a third embodiment, modulating agents having a branched structure comprise an HAV-BM sequence, YAT, FAT, YAS, LYHY (SEQ ID NO:70) and RAL.

Linkers preferably produce a distance between CAR sequences between 0.1 to 10,000 nm, more preferably about 0.1–400 nm. A separation distance between recognition sites may generally be determined according to the desired function of the modulating agent. For inhibitors of cell adhesion, the linker distance between HAV-BM sequences should be small (0.1–400 nm). For enhancers of cell adhesion, the linker distance between HAV-BM sequences should be 400–10,000 nm. One linker that can be used for such purposes is $(H_2N(CH_2)_nCO_2H)_m$, or derivatives thereof, where n ranges from 1 to 10 and m ranges from 1 to 4000. For example, if glycine ($H_2NCH_2CO_2H$) or a multimer thereof is used as a linker, each glycine unit corresponds to a linking distance of 2.45 angstroms, or 0.245 nm, as determined by calculation of its lowest energy conformation when linked to other amino acids using molecular modeling techniques. Similarly, aminopropanoic acid corresponds to a linking distance of 3.73 angstroms, aminobutanoic acid to 4.96 angstroms, aminopentanoic acid to 6.30 angstroms and amino hexanoic acid to 6.12 angstroms. Other linkers that may be used will be apparent to those of ordinary skill in the art and include, for example, linkers based on repeat units of 2,3-diaminopropanoic acid, lysine and/or ornithine. 2,3-Diaminopropanoic acid can provide a linking distance of either 2.51 or 3.11 angstroms depending on whether the side-chain amino or terminal amino is used in the linkage. Similarly, lysine can provide linking distances of either 2.44 or 6.95 angstroms and ornithine 2.44 or 5.61 angstroms. Peptide and non-peptide linkers may generally be incorporated into a modulating agent using any appropriate method known in the art.

Modulating agents that inhibit cell adhesion typically contain one HAV-BM sequence or multiple HAV-BM sequences, which may be adjacent to one another (i.e., without intervening sequences) or in close proximity (i.e., separated by peptide and/or non-peptide linkers to give a distance between the CAR sequences that ranges from about 0.1 to 400 nm). Within one such embodiment, a modulating agent contains two HAV-BM sequences. Such a modulating agent may additionally comprise a CAR sequence for one or more different adhesion molecules (including, but not limited to, other CAMs) and/or one or more antibodies or fragments thereof that bind to such sequences. Linkers may, but need not, be used to separate such CAR sequence(s) and/or antibody sequence(s) from the HAV-BM sequence(s) and/or each other. Such modulating agents may generally be used within methods in which it is desirable to simultaneously disrupt cell adhesion mediated by multiple adhesion molecules. Within certain preferred embodiments, the second CAR sequence is derived from fibronectin and is recognized by an integrin (i.e., RGD; see Cardarelli et al., *J. Biol. Chem.* 267:23159–23164, 1992), or is an occludin CAR sequence (e.g., LYHY; SEQ ID NO:70). One or more antibodies, or fragments thereof, may similarly be used within such embodiments.

Modulating agents that enhance cell adhesion may contain multiple HAV-BM sequences, and/or antibodies that specifically bind to such sequences, joined by linkers as described above. Enhancement of cell adhesion may also be achieved by attachment of multiple modulating agents to a support molecule or material, as discussed further below. Such modulating agents may additionally comprise one or more CAR sequence for one or more different adhesion molecules (including, but not limited to, other CAMs) and/or one or more antibodies or fragments thereof that bind to such sequences, to enhance cell adhesion mediated by multiple adhesion molecules.

As noted above, modulating agents may be polypeptides or salts thereof, containing only amino acid residues linked by peptide bonds, or may contain non-peptide regions, such as linkers. Peptide regions of a modulating agent may comprise residues of L-amino acids, D-amino acids, or any combination thereof. Amino acids may be from natural or non-natural sources, provided that at least one amino group and at least one carboxyl group are present in the molecule; α- and β-amino acids are generally preferred. The 20 L-amino acids commonly found in proteins are identified herein by the conventional three-letter or one-letter abbreviations.

A modulating agent may also contain rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylation), with or without any of a wide variety of side-chain modifications and/or substitutions (e.g., methylation, benzylation, t-butylation, tosylation, alkoxycarbonylation, and the like). Preferred derivatives include amino acids having a C-terminal amide group. Residues other than common amino acids that may be present with a modulating agent include, but are not limited to, 2-mercaptoaniline, 2-mercaptoproline, ornithine, diaminobutyric acid, α-aminoadipic acid, m-aminomethylbenzoic acid and α,β-diaminopropionic acid.

Peptide modulating agents (and peptide portions of modulating agents) as described herein may be synthesized by methods well known in the art, including chemical synthesis and recombinant DNA methods. For modulating agents up to about 50 residues in length, chemical synthesis may be performed using solid phase peptide synthesis techniques, in which a peptide linkage occurs through the direct condensation of the α-amino group of one amino acid with the α-carboxy group of the other amino acid with the elimination of a water molecule. Peptide bond synthesis by direct condensation, as formulated above, requires suppression of the reactive character of the amino group of the first and of the carboxyl group of the second amino acid. The masking substituents must permit their ready removal, without inducing breakdown of the labile peptide molecule.

Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., *J. Am. Chem. Soc.* 85:2149, 1963, which involves assembling a linear peptide chain on a resin support using protected amino acids. Solid phase peptide synthesis typically utilizes either the Boc or Fmoc strategy. The Boc strategy uses a 1% cross-linked polystyrene resin. The standard protecting group for α-amino functions is the tert-butyloxycarbonyl (Boc) group. This group can be removed with dilute solutions of strong acids such as 25% trifluoroacetic acid (TFA). The next Boc-amino acid is typically coupled to the amino acyl resin using dicyclohexylcarbodiimide (DCC). Following completion of the assembly, the peptide-resin is treated with anhydrous HF to cleave the benzyl ester link and liberate the free peptide. Side-chain functional groups are usually blocked during synthesis by benzyl-derived blocking groups, which are also cleaved by HF. The free peptide is then extracted from the resin with a suitable solvent, purified and characterized. Newly synthesized peptides can be purified, for example, by gel filtration, HPLC, partition chromatography and/or ion-exchange chromatography, and may be characterized by, for example, mass spectrometry or amino acid sequence analysis. In the Boc strategy, C-terminal amidated peptides can be obtained using benzhydrylamine or methylbenzhydrylamine resins, which yield peptide amides directly upon cleavage with HF.

In the procedures discussed above, the selectivity of the side-chain blocking groups and of the peptide-resin link depends upon the differences in the rate of acidolytic cleavage. Orthoganol systems have been introduced in which the side-chain blocking groups and the peptide-resin link are completely stable to the reagent used to remove the α-protecting group at each step of the synthesis. The most common of these methods involves the 9-fluorenylmethyloxycarbonyl (Fmoc) approach. Within this method, the side-chain protecting groups and the peptide-resin link are completely stable to the secondary amines used for cleaving the N-α-Fmoc group. The side-chain protection and the peptide-resin link are cleaved by mild acidolysis. The repeated contact with base makes the Merrifield resin unsuitable for Emoc chemistry, and p-alkoxybenzyl esters linked to the resin are generally used. Deprotection and cleavage are generally accomplished using TFA.

Those of ordinary skill in the art will recognize that, in solid phase synthesis, deprotection and coupling reactions must go to completion and the side-chain blocking groups must be stable throughout the entire synthesis. In addition, solid phase synthesis is generally most suitable when peptides are to be made on a small scale.

Acetylation of the N-terminus can be accomplished by reacting the final peptide with acetic anhydride before cleavage from the resin. C-amidation is accomplished using an appropriate resin such as methylbenzhydrylamine resin using the Boc technology.

Following synthesis of a linear peptide, with or without N-acetylation and/or C-amidation, cyclization may be achieved if desired by any of a variety of techniques well known in the art. Within one embodiment, a bond may be generated between reactive amino acid side chains. For example, a disulfide bridge may be formed from a linear peptide comprising two thiol-containing residues by oxidizing the peptide using any of a variety of methods. Within one such method, air oxidation of thiols can generate disulfide linkages over a period of several days using either basic or neutral aqueous media. The peptide is used in high dilution to minimize aggregation and intermolecular side reactions. This method suffers from the disadvantage of being slow but has the advantage of only producing $H_2O$ as a side product. Alternatively, strong oxidizing agents such as $I_2$ and $K_3Fe(CN)_6$ can be used to form disulfide linkages. Those of ordinary skill in the art will recognize that care must be taken not to oxidize the sensitive side chains of Met, Tyr, Trp or His. Cyclic peptides produced by this method require purification using standard techniques, but this oxidation is applicable at acid pHs. Oxidizing agents also allow concurrent deprotection/oxidation of suitable S-protected linear precursors to avoid premature, nonspecific oxidation of free cysteine.

DMSO, unlike $I_2$ and $K_3Fe(CN)_6$, is a mild oxidizing agent which does not cause oxidative side reactions of the nucleophilic amino acids mentioned above. DMSO is miscible with $H_2O$ at all concentrations, and oxidations can be performed at acidic to neutral pHs with harmless byproducts. Methyltrichlorosilane-diphenylsulfoxide may alternatively be used as an oxidizing agent, for concurrent deprotection/oxidation of S-Acm, S-Tacm or S-t-Bu of cysteine without affecting other nucleophilic amino acids. There are no polymeric products resulting from intermolecular disulfide bond formation. Suitable thiol-containing residues for use in such oxidation methods include, but are not limited to, cysteine, β,β-dimethyl cysteine (penicillamine or Pen), β,β-tetramethylene cysteine (Tmc), β,β-pentamethylene cysteine (Pmc), β-mercaptopropionic acid (Mpr), β,β-pentamethylene-β-mercaptopropionic acid (Pmp), 2-mercaptobenzene, 2-mercaptoaniline and 2-mercaptoproline.

Within another embodiment, cyclization may be achieved by amide bond formation. For example, a peptide bond may be formed between terminal functional groups (i.e., the amino and carboxy termini of a linear peptide prior to cyclization). Within another such embodiment, the linear peptide comprises a D-amino acid. Alternatively, cyclization may be accomplished by linking one terminus and a residue side chain or using two side chains, with or without an N-terminal acetyl group and/or a C-terminal amide. Residues capable of forming a lactam bond include lysine, ornithine (Orn), α-amino adipic acid, m-aminomethylbenzoic acid, α,β-diaminopropionic acid, glutamate or aspartate.

Methods for forming amide bonds are well known in the art and are based on well established principles of chemical reactivity. Within one such method, carbodiimide-mediated lactam formation can be accomplished by reaction of the carboxylic acid with DCC, DIC, EDAC or DCCI, resulting in the formation of an O-acylurea that can be reacted immediately with the free amino group to complete the cyclization. The formation of the inactive N-acylurea, resulting from O→N migration, can be circumvented by converting the O-acylurea to an active ester by reaction with an N-hydroxy compound such as 1-hydroxybenzotriazole, 1-hydroxysuccinimide, 1-hydroxynorbornene carboxamide or ethyl 2-hydroximino-2-cyanoacetate. In addition to minimizing O→N migration, these additives also serve as catalysts during cyclization and assist in lowering racemization. Alternatively, cyclization can be performed using the azide method, in which a reactive azide intermediate is generated from an alkyl ester via a hydrazide. Hydrazinolysis of the terminal ester necessitates the use of a t-butyl group for the protection of side chain carboxyl functions in the acylating component. This limitation can be overcome by using diphenylphosphoryl acid (DPPA), which furnishes an azide directly upon reaction with a carboxyl group. The slow reactivity of azides and the formation of isocyanates by their disproportionation restrict the usefulness of this method. The mixed anhydride method of lactam formation is widely used because of the facile removal of reaction by-products. The anhydride is formed upon reaction of the carboxylate anion with an alkyl chloroformate or pivaloyl chloride. The attack of the amino component is then guided to the carbonyl carbon of the acylating component by the electron donating effect of the alkoxy group or by the steric bulk of the pivaloyl chloride t-butyl group, which obstructs attack on the wrong carbonyl group. Mixed anhydrides with phosphoric acid derivatives have also been successfully used. Alternatively, cyclization can be accomplished using activated esters. The presence of electron withdrawing substituents on the alkoxy carbon of esters increases their susceptibility to aminolysis. The high reactivity of esters of p-nitrophenol, N-hydroxy compounds and polyhalogenated phenols has made these "active esters" useful in the synthesis of amide bonds. The last few years have witnessed the development of benzotriazolyloxytris-(dimethylamino) phosphonium bexafluorophosphonate (BOP) and its congeners as advantageous coupling reagents. Their performance is generally superior to that of the well established carbodiimide amide bond formation reactions.

Within a further embodiment, a thioether linkage may be formed between the side chain of a thiol-containing residue and an appropriately derivatized α-amino acid. By way of example, a lysine side chain can be coupled to bromoacetic acid through the carbodiimide coupling method (DCC, EDAC) and then reacted with the side chain of any of the thiol containing residues mentioned above to form a thioether linkage. In order to form dithioethers, any two thiol containing side-chains can be reacted with dibromoethane and diisopropylamine in DMF.

For longer modulating agents, recombinant methods are preferred for synthesis. Within such methods, all or part of a modulating agent can be synthesized in living cells, using any of a variety of expression vectors known to those of ordinary skill in the art to be appropriate for the particular host cell. Suitable host cells may include bacteria, yeast cells, mammalian cells, insect cells, plant cells, algae and other animal cells (e.g., hybridoma, CHO, myeloma). The DNA sequences expressed in this manner may encode portions of an endogenous cadherin or other adhesion molecule. Such sequences may be prepared based on known cDNA or genomic sequences (see Blaschuk et al., *J. Mol.*

Biol. 211:679–682, 1990), or from sequences isolated by screening an appropriate library with probes designed based on the sequences of known cadherins. Such screens may generally be performed as described in Sambrook et al., *Molecular Cloning: A Laboratory Manual*, Cold Spring Harbor Laboratories, Cold Spring Harbor, N.Y., 1989 (and references cited therein). Polymerase chain reaction (PCR) may also be employed, using oligonucleotide primers in methods well known in the art, to isolate nucleic acid molecules encoding all or a portion of an endogenous adhesion molecule. To generate a nucleic acid molecule encoding a desired modulating agent, an endogenous cadherin sequence may be modified using well known techniques. For example, portions encoding one or more CAR sequences may be joined, with or without separation by nucleic acid regions encoding linkers, as discussed above. Alternatively, portions of the desired nucleic acid sequences may be synthesized using well known techniques, and then ligated together to form a sequence encoding the modulating agent.

As noted above, instead of (or in addition to) an HAV-BM sequence, a modulating agent may comprise an antibody, or antigen-binding fragment thereof, that specifically binds to an HAV-BM sequence. As used herein, an antibody, or antigen-binding fragment thereof, is said to "specifically bind" to an HAV-BM sequence (with or without flanking amino acids) if it reacts at a detectable level with a peptide containing that sequence, and does not react detectably with peptides containing a different CAR sequence or a sequence in which the order of amino acid residues in the cadherin CAR sequence and/or flanking sequence is altered. Such antibody binding properties may be assessed using an ELISA, as described by Newton et al., *Develop. Dynamics* 197:1–13, 1993.

Polyclonal and monoclonal antibodies may be raised against an HAV-BM sequence using conventional techniques. See, e.g., Harlow and Lane, *Antibodies: A Laboratory Manual*, Cold Spring Harbor Laboratory, 1988. In one such technique, an immunogen comprising the HAV-BM sequence is initially injected into any of a wide variety of mammals (e.g., mice, rats, rabbits, sheep or goats). The smaller immunogens (i.e., less than about 20 amino acids) should be joined to a carrier protein, such as bovine serum albumin or keyhole limpet hemocyanin. Following one or more injections, the animals are bled periodically. Polyclonal antibodies specific for the CAR sequence may then be purified from such antisera by, for example, affinity chromatography using the modulating agent or antigenic portion thereof coupled to a suitable solid support.

Monoclonal antibodies specific for the HAV-BM sequence may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity from spleen cells obtained from an animal immunized as described above. The spleen cells are immortalized by, for example, fusion with a myeloma cell fusion partner, preferably one that is syngeneic with the immunized animal. Single colonies are selected and their culture supernatants tested for binding activity against the modulating agent or antigenic portion thereof. Hybridomas having high reactivity and specificity are preferred.

Monoclonal antibodies may be isolated from the supernatants of growing hybridoma colonies, with or without the use of various techniques known in the art to enhance the yield. Contaminants may be removed from the antibodies by conventional techniques, such as chromatography, gel filtration, precipitation and extraction. Antibodies having the desired activity may generally be identified using immunofluorescence analyses of tissue sections, cell or other samples where the target cadherin is localized.

Within preferred embodiments, such monoclonal antibodies are specific for particular cadherins (e.g., the antibodies bind to E-cadherin, but do not bind significantly to N-cadherin, or vise versa). Such antibodies may be prepared as described above, using an immunogen that comprises (in addition to a minimal HAV-BM sequence) sufficient flanking sequence to generate the desired specificity. To evaluate the specificity of a particular antibody, representative assays as described herein and/or conventional antigen-binding assays may be employed. Such antibodies may generally be used for therapeutic, diagnostic and assay purposes, as described herein. For example, such antibodies may be linked to a drug and administered to a mammal to target the drug to a particular cadherin-expressing cell.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988; see especially page 309) and digested by papain to yield Fab and Fc fragments. The Fab and Fc fragments may be separated by affinity chromatography on protein A bead columns (Harlow and Lane, 1988, pages 628–29).

Within certain embodiments, antibodies may be used within methods in which enhanced cell adhesion is desired, as described above. For example, antibodies may be used within the above methods for enhancing and/or directing neurite outgrowth in vitro or in vivo. Antibodies may be used within the lumen of a tubular nerve guide or may be attached to a fiber nerve guide, suture or other solid support and used as described above for peptide modulating agents. Antibody dosages are sufficient to enhance or direct neurite outgrowth, and will vary with the method of administration and the condition to be treated.

Antibodies may also be used as a "biological glue," as described above to bind multiple cadherin-expressing cells within a variety of contexts, such as to enhance wound healing and/or reduce scar tissue, and/or to facilitate cell adhesion in skin grafting or prosthetic implants. In general, the amount of matrix-linked antibody administered to a wound, graft or implant site varies with the severity of the wound and/or the nature of the wound, graft, or implant, but may vary as discussed above. Antibodies may also be linked to any of a variety of support materials, as described above, for use in tissue culture or bioreactors.

Antibodies (or, preferably, antigen-binding fragments thereof) may also be used in situations where inhibition of cell adhesion is desired. Such antibodies or fragments may be used, for example, for treatment of demyelinating diseases, such as MS, or to inhibit interactions between tumor cells, as described above. The use of Fab fragments is generally preferred.

EVALUATION OF MODULATING AGENT ACTIVITY

As noted above, native HAV-BM sequences, as well as analogues and mimetics thereof, bind to a classical cadherin, preferably within or near an HAV sequence, and modulate a cadherin-mediated response. The ability to bind to a cadherin sequence may generally be evaluated using any binding assay known to those of ordinary skill in the art. For example, a Pharmacia Biosensor machine may be used, as discussed in Jonsson et al., *Biotechniques* 11:520–27, 1991. A specific example of the technology that measures the interaction of peptides with molecules can be found in Williams et al., *J. Biol. Chem.* 272:8539–8545, 1997. Real-time BIA (Biomolecular Interaction Analysis) uses the optical phenomenon surface plasmon resonance to monitor biomolecular interactions. The detection depends upon changes in the mass concentration of macromolecules at the biospecific interface, which in turn depends upon the immobilization of test molecule or peptide (referred to as the ligand) to the surface of a Biosensor chip, followed by binding of the interacting molecule (referred to as the analyte) to the ligand. Binding to the chip is measured in real-time in arbitrary units of resonance (RU).

For example, surface plasmon resonance experiments may be carried out using a BIAcore X™ Biosensor (Pharmacia Ltd., BIAcore, Uppsala, Sweden). Parallel flow cells of CM 5 sensor chips may be derivatized, using the amine coupling method, with streptavidin (200 µg/ml) in 10 mM Sodium Acetate, pH 4.0, according to the manufacturer's protocol. Approximately 2100–2600 resonance units (RU) of ligand may be immobilized, corresponding to a concentration of about 2.1–2.6 ng/mm$^2$. The chips may then coated be with a peptide comprising a known or putative HAV-BM, or analogue or mimetic thereof. Any non-specifically bound peptide is removed.

To determine binding, test analytes (e.g., cadherin peptides, such as HAV-containing peptides) may be placed in running buffer and passed simultaneously over test and control flow cells. After a period of free buffer flow, any analyte remaining bound to the surface may be removed with, for example, a pulse of 0.1% SDS bringing the signal back to baseline. Specific binding to the derivatized sensor chips may be determined automatically by the system by subtraction of test from control flow cell responses. In general, an HAV-BM, or a mimetic or analogue thereof, binds an HAV-containing peptide at a detectable level within such as assay. Preferably, the level of binding is at least that observed for a native HAV-BM as provided herein under similar conditions.

The ability to modulate a cadherin-mediated function may be evaluated using any of a variety of in vitro assays designed to measure the effect of the peptide on a typical cadherin response. As noted above, modulating agents may be capable of enhancing or inhibiting a cadherin-mediated function. The ability of an agent to modulate cell adhesion may generally be evaluated in vitro by assaying the effect on one or more of the following: (1) neurite outgrowth, (2) Schwann cell-astrocyte adhesion, (3) Schwann cell migration on astrocyte monolayers, (4) adhesion between endothelial cells, (5) adhesion between epithelial cells (e.g., normal rat kidney cells and/or human skin) and/or (6) adhesion between cancer cells. In general, a modulating agent is an inhibitor of cell adhesion if, within one or more of these representative assays, contact of the test cells with the modulating agent results in a discernible disruption of cell adhesion. Modulating agents that enhance cell adhesion (e.g., agents comprising multiple HAV-BM sequences and/or linked to a support material) are considered to be modulators of cell adhesion if they are capable of enhancing neurite outgrowth as described below or are capable of promoting cell adhesion, as judged by plating assays to assess epithelial cell adhesion to a modulating agent attached to a support material, such as tissue culture plastic.

Within a representative neurite outgrowth assay, neurons may be cultured on a monolayer of cells (e.g., 3T3 fibroblasts) that express N-cadherin. Neurons grown on such cells (under suitable conditions and for a sufficient period of time) extend neurites that are typically, on average, twice as long as neurites extended from neurons cultured on 3T3 cells that do not express N-cadherin. For example, neurons may be cultured on monolayers of 3T3 cells transfected with cDNA encoding N-cadherin essentially as described by Doherty and Walsh, *Curr. Op. Neurobiol.* 4:49–55, 1994; Williams et al., *Neuron* 13:583–594, 1994; Hall et al., *Cell Adhesion and Commun.* 3:441–450, 1996; Doherty and Walsh, *Mol. Cell. Neurosci.* 8:99–111, 1994; and Safell et al., *Neuron* 18:231–242, 1997. Briefly, monolayers of control 3T3 fibroblasts and 3T3 fibroblasts that express N-cadherin may be established by overnight culture of 80,000 cells in individual wells of an 8-chamber well tissue culture slide. 3000 cerebellar neurons isolated from post-natal day 3 mouse brains may be cultured for 18 hours on the various monolayers in control media (SATO/2% FCS), or media supplemented with various concentrations of the modulating agent or control peptide. The cultures may then be fixed and stained for GAP43 which specifically binds to the neurons and their neurites. The length of the longest neurite on each GAP43 positive neuron may be measured by computer assisted morphometry.

A modulating agent that modulates N-cadherin-mediated cell adhesion may inhibit or enhance such neurite outgrowth. Under the conditions described above, the presence of 500 μg/mL of a modulating agent that disrupts neural cell adhesion should result in a decrease in the mean neurite length by at least 50%, relative to the length in the absence of modulating agent or in the presence of a negative control peptide. Alternatively, the presence of 500 μg/mL of a modulating agent that enhances neural cell adhesion should result in an increase in the mean neurite length by at least 50%.

The effect of a modulating agent on Schwann cell adhesion to astrocytes may generally be evaluated using a cell adhesion assay. Briefly, Schwann cells fluorescently labeled with Di-I may be plated onto an astrocytic surface (e.g., a glass coverslip coated with a monolayer of astrocytes) and incubated on a shaking platform (e.g., 25 rpm for 30 minutes) in the presence and absence of modulating agent at a concentration of approximately 1 mg/mL. Cells may then be washed (e.g., in Hanks medium) to remove non-attached cells. The attached cells may then be fixed and counted (e.g., using a fluorescent microscope). In general, 1 mg/mL of a modulating agent results in an increase or decrease in cell adhesion of at least 50%. This assay evaluates the effect of a modulating agent on N-cadherin mediated cell adhesion.

Schwann cell migration may generally be evaluated using a micro-inverted-coverslip assay. In this assay, a dense Schwann cell culture is established on coverslip fragments and Schwann cell migration away from the fragment edge is measured. Briefly, Schwann cells fluorescently labeled with Di-I may be plated on polylysine- and laminin-coated fragments of a glass coverslip and allowed to bind to the surface for 16–18 hours. Cells may then be washed (e.g., in Hanks medium) to remove non-attached cells, and then inverted, with cells facing downward onto an astrocyte-coated surface. Cultures are then incubated further for 2 days in the presence or absence of modulating agent at a concentration of approximately 1 mg/mL and fixed. The maximum migration distance from the edge of the coverslip fragment may then be measured. At a level of 1 mg/mL, a modulating agent results in an increase or decrease in the maximum migration distance of at least 50%. This assay evaluates the effect of a modulating agent on N-cadherin mediated cell adhesion.

Within certain cell adhesion assays, the addition of a modulating agent to cells that express a cadherin results in disruption of cell adhesion. A "cadherin-expressing cell," as used herein, may be any type of cell that expresses at least one cadherin on the cell surface at a detectable level, using standard techniques such as immunocytochemical protocols (e.g., Blaschuk and Farookhi, Dev. Biol. 136:564–567, 1989). Cadherin-expressing cells include endothelial, epithelial and/or cancer cells. For example, such cells may be plated under standard conditions that, in the absence of modulating agent, permit cell adhesion. In the presence of modulating agent (e.g., 500 µg/mL), disruption of cell adhesion may be determined visually within 24 hours, by observing retraction of the cells from one another.

For use within one such assay, bovine pulmonary artery endothelial cells may be harvested by sterile ablation and digestion in 0.1% collagenase (type II; Worthington Enzymes, Freehold, N.J.). Cells may be maintained in Dulbecco's minimum essential medium supplemented with 10% fetal calf serum and 1% antibiotic-antimycotic at 37° C. in 7% $CO_2$ in air. Cultures may be passaged weekly in trypsin-EDTA and seeded onto tissue culture plastic at 20,000 cells/$cm^2$. Endothelial cultures may be used at 1 week in culture, which is approximately 3 days after culture confluency is established. The cells may be seeded onto coverslips and treated (e.g., for 30 minutes) with modulating agent or a control compound at, for example, 500 µg/ml and then fixed with 1% paraformaldehyde. As noted above, disruption of cell adhesion may be determined visually within 24 hours, by observing retraction of the cells from one another. This assay evaluates the effect of a modulating agent on N-cadherin mediated cell adhesion.

Within another such assay, the effect of a modulating agent on normal rat kidney (NRK) cells may be evaluated. According to a representative procedure, NRK cells (ATCC #1571-CRL) may be plated at 10–20,000 cells per 35 mm tissue culture flasks containing DMEM with 10% FCS and sub-cultured periodically (Laird et al., J. Cell Biol. 131:1193–1203, 1995). Cells may be harvested and replated in 35 mm tissue culture flasks containing 1 mm coverslips and incubated until 50–65% confluent (24–36 hours). At this time, coverslips may be transferred to a 24-well plate, washed once with fresh DMEM and exposed to modulating agent at a concentration of, for example, 1 mg/mL for 24 hours. Fresh modulating agent may then be added, and the cells left for an additional 24 hours. Cells may be fixed with 100% methanol for 10 minutes and then washed three times with PBS. Coverslips may be blocked for 1 hour in 2% BSA/PBS and incubated for a further 1 hour in the presence of mouse anti-E-cadherin antibody (Transduction Labs, 1:250 dilution). Primary and secondary antibodies may be diluted in 2% BSA/PBS. Following incubation in the primary antibody, coverslips may be washed three times for 5 minutes each in PBS and incubated for 1 hour with donkey anti-mouse antibody conjugated to fluorescein (diluted 1:200). Following further washes in PBS (3×5 min) coverslips can be mounted and viewed by confocal microscopy.

In the absence of modulating agent, NRK cells form characteristic tightly adherent monolayers with a cobblestone morphology in which cells display a polygonal shape. NRK cells that are treated with a modulating agent that disrupts E-cadherin mediated cell adhesion may assume a non-polygonal and elongated morphology (i.e., a fibroblast-like shape) within 48 hours of treatment with 1 mg/mL of modulating agent. Gaps appear in confluent cultures of such cells. In addition, 1 mg/mL of such a modulating agent reproducibly induces a readily apparent reduction in cell surface staining of E-cadherin, as judged by immunofluorescence microscopy (Laird et al., J. Cell Biol. 131:1193–1203, 1995), of at least 75% within 48 hours.

A third cell adhesion assay involves evaluating the effect of a modulating agent on permeability of adherent epithelial and/or endothelial cell layers. For example, the effect of permeability on human skin may be evaluated. Such skin may be derived from a natural source or may be synthetic. Human abdominal skin for use in such assays may generally be obtained from humans at autopsy within 24 hours of death. Briefly, a modulating agent (e.g., 500 µg/ml) and a test marker (e.g., the fluorescent markers Oregon Green™ and Rhodamine Green™ Dextran) may be dissolved in a sterile buffer (e.g., phosphate buffer, pH 7.2), and the ability of the marker to penetrate through the skin and into a receptor fluid (e.g., phosphate buffer) may be measured using a Franz Cell apparatus (Franz, Curr. Prob. Dermatol. 7:58–68, 1978; Franz, J. Invest. Dermatol. 64:190–195, 1975). The penetration of the markers through the skin may be assessed at, for example, 6, 12, 24, 36, and 48 hours after the start of the experiment. In general, a modulating agent that enhances the permeability of human skin results in a statistically significant increase in the amount of marker in the receptor compartment after 6–48 hours in the presence of 500 µg/mL modulating agent. This assay evaluates the effect of a modulating agent on E-cadherin mediated cell adhesion.

MODULATING AGENT MODIFICATION AND FORMULATIONS

A modulating agent as described herein may, but need not, be linked to one or more additional molecules. In particular, as discussed below, it may be beneficial for certain applications to link multiple modulating agents (which may, but need not, be identical) to a support material, such as a support molecule (e.g., keyhole limpet hemocyanin) or a solid support, such as a polymeric matrix (which may be formulated as a membrane or microstructure, such as an ultra thin film), a container surface (e.g., the surface of a tissue culture plate or the interior surface of a bioreactor), or a bead or other particle, which may be prepared from a variety of materials including glass, plastic or ceramics. For certain applications, biodegradable support materials are preferred, such as cellulose and derivatives thereof, collagen, spider silk or any of a variety of polyesters (e.g., those derived from hydroxy acids and/or lactones) or sutures (see U.S. Pat. No. 5,245,012). Within certain embodiments, modulating agents and molecules comprising other CAR sequence(s) (e.g, HAV, RGD or LYHY (SEQ ID NO:70)) may be attached to a support such as a polymeric matrix, preferably in an alternating pattern.

Suitable methods for linking a modulating agent to a support material will depend upon the composition of the support and the intended use, and will be readily apparent to those of ordinary skill in the art. Attachment may generally be achieved through noncovalent association, such as adsorption or affinity or, preferably, via covalent attachment (which may be a direct linkage between a modulating agent and functional groups on the support, or may be a linkage by way of a cross-linking agent). Attachment of a modulating agent by adsorption may be achieved by contact, in a suitable buffer, with a solid support for a suitable amount of time. The contact time varies with temperature, but is generally between about 5 seconds and 1 day, and typically between about 10 seconds and 1 hour.

Covalent attachment of a modulating agent to a molecule or solid support may generally be achieved by first reacting the support material with a bifunctional reagent that will also react with a functional group, such as a hydroxyl or amino group, on the modulating agent. For example, a modulating agent may be bound to an appropriate polymeric support or coating using benzoquinone, by condensation of an aldehyde group on the support with an amine and an active hydrogen on the modulating agent or by condensation of an amino group on the support with a carboxylic acid on the modulating agent. A preferred method of generating a linkage is via amino groups using glutaraldehyde. A modulating agent may be linked to cellulose via ester linkages. Similarly, amide linkages may be suitable for linkage to other molecules such as keyhole limpet hemocyanin or other support materials. Multiple modulating agents and/or molecules comprising other CAR sequences may be attached, for example, by random coupling, in which equimolar amounts of such molecules are mixed with a matrix support and allowed to couple at random.

Although modulating agents as described herein may preferentially bind to specific tissues or cells, and thus may be sufficient to target a desired site in vivo, it may be beneficial for certain applications to include an additional targeting agent. Accordingly, a targeting agent may also, or alternatively, be linked to a modulating agent to facilitate targeting to one or more specific tissues. As used herein, a "targeting agent," may be any substance (such as a compound or cell) that, when linked to a modulating agent enhances the transport of the modulating agent to a target tissue, thereby increasing the local concentration of the modulating agent. Targeting agents include antibodies or fragments thereof, receptors, ligands and other molecules that bind to cells of, or in the vicinity of, the target tissue. Known targeting agents include serum hormones, antibodies against cell surface antigens, lectins, adhesion molecules, tumor cell surface binding ligands, steroids, cholesterol, lymphokines, fibrinolytic enzymes and those drugs and proteins that bind to a desired target site. Among the many monoclonal antibodies that may serve as targeting agents are anti-TAC, or other interleukin-2 receptor antibodies; 9.2.27 and NR-ML-05, reactive with the 250 kilodalton human melanoma-associated proteoglycan; and NR-LU-10, reactive with a pancarcinoma glycoprotein. An antibody targeting agent may be an intact (whole) molecule, a fragment thereof, or a functional equivalent thereof. Examples of antibody fragments are F(ab')2, -Fab', Fab and F[v] fragments, which may be produced by conventional methods or by genetic or protein engineering. Linkage is generally covalent and may be achieved by, for example, direct condensation or other reactions, or by way of bi- or multifunctional linkers. Within other embodiments, it may also be possible to target a polynucleotide encoding a modulating agent to a target tissue, thereby increasing the local concentration of modulating agent. Such targeting may be achieved using well known techniques, including retroviral and adenoviral infection.

For certain embodiments, it may be beneficial to also, or alternatively, link a drug to a modulating agent. As used herein, the term "drug" refers to any bioactive agent intended for administration to a mammal to prevent or treat a disease or other undesirable condition. Drugs include hormones, growth factors, proteins, peptides and other compounds. The use of certain specific drugs within the context of the present invention is discussed below.

Within certain aspects of the present invention, one or more modulating agents as described herein may be present within a pharmaceutical composition. A pharmaceutical composition comprises one or more modulating agents in combination with one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. One or more modulating agents (alone or in combination with a targeting agent and/or drug) may, but need not, be encapsulated within liposomes using well known technology. Compositions of the present invention may be formulated for any appropriate manner of administration, including for example, topical, oral, nasal, intravenous, intracranial, intraperitoneal, subcutaneous, or intramuscular administration.

For certain embodiments, as discussed below, a pharmaceutical composition may further comprise a modulator of cell adhesion that is mediated by one or more molecules other than cadherins. Such modulators may generally be prepared as described above, incorporating one or more non-cadherin CAR sequences and/or antibodies thereto in place of the HAV-BM sequences and antibodies. Such compositions are particularly useful for situations in which it is desirable to inhibit cell adhesion mediated by multiple cell-adhesion molecules, such as other members of the cadherin gene superfamily that are not classical cadherins (e.g., Dsg and Dsc); integrins; members of the immunoglobulin supergene family, such as N-CAM; and other uncategorized transmembrane proteins, such as occludin, as well as extracellular matrix proteins such as laminin, fibronectin, collagens, vitronectin, entactin and tenascin. Preferred CAR sequences for use within such a modulator include HAV, RGD, YIGSR (SEQ ID NO:66), KYSFNYDGSE (SEQ ID NO:67), IWKHKGRDVILKKDVRF (SEQ ID NO:68), YAT, FAT, YAS, RAL and/or GVNPTAQSSGSLYGSQIY-ALCNQFYTPAATGLYVDQYLYHYCVVDPQE (SEQ ID NO:69), or derivatives or portions thereof such as LYHY (SEQ ID NO:70).

A pharmaceutical composition may also, or alternatively, contain one or more drugs, which may be linked to a modulating agent or may be free within the composition. Virtually any drug may be administered in combination with a modulating agent as described herein, for a variety of purposes as described below. Examples of types of drugs that may be administered with a modulating agent include analgesics, anesthetics, antianginals, antifungals, antibiotics, anticancer drugs (e.g., taxol or mitomycin C), antiinflammatories (e.g., ibuprofen and indomethacin), anthelmintics, antidepressants, antidotes, antiemetics, antihistamines, antihypertensives, antimalarials, antimicrotubule agents (e.g., colchicine or vinca alkaloids), antimigraine agents, antimicrobials, antiphsychotics, antipyretics, antiseptics, anti-signaling agents (e.g., protein kinase C inhibitors or inhibitors of intracellular calcium mobilization), antiarthritics, antithrombin agents, antituberculotics, antitussives, antivirals, appetite suppressants, cardioactive drugs, chemical dependency drugs, cathartics, chemotherapeutic agents, coronary, cerebral or peripheral vasodilators, contraceptive agents, depressants, diuretics, expectorants, growth factors, hormonal agents, hypnotics, immunosuppression agents, narcotic antagonists, parasympathomimetics, sedatives, stimulants, sympathomimetics, toxins (e.g., cholera toxin), tranquilizers and urinary antiinfectives.

For imaging purposes, any of a variety of diagnostic agents may be incorporated into a pharmaceutical composition, either linked to a modulating agent or free within the composition. Diagnostic agents include any substance administered to illuminate a physiological function within a patient, while leaving other physiological functions generally unaffected. Diagnostic agents include metals, radioactive isotopes and radioopaque agents (e.g., gallium, technetium, indium, strontium, iodine, barium, bromine and phosphorus-containing compounds), radiolucent agents, contrast agents, dyes (e.g., fluorescent dyes and chromophores) and enzymes that catalyze a calorimetric or fluorometric reaction. In general, such agents may be attached using a variety of techniques as described above, and may be present in any orientation.

The compositions described herein may be administered as part of a sustained release formulation (i.e., a formulation such as a capsule or sponge that effects a slow release of modulating agent following administration). Such formulations may generally be prepared using well known technology and administered by, for example, oral, rectal or subcutaneous implantation, or by implantation at the desired target site. Sustained-release formulations may contain a modulating agent dispersed in a carrier matrix and/or contained within a reservoir surrounded by a rate controlling membrane (see, e.g., European Patent Application 710,491 A). Carriers for use within such formulations are biocompatible, and may also be biodegradable; preferably the formulation provides a relatively constant level of modulating agent release. The amount of modulating agent contained within a sustained release formulation depends upon the site of implantation, the rate and expected duration of release and the nature of the condition to be treated or prevented.

Pharmaceutical compositions of the present invention may be administered in a manner appropriate to the disease to be treated (or prevented). Appropriate dosages and a suitable duration and frequency of administration will be determined by such factors as the condition of the patient, the type and severity of the patient's disease and the method of administration. In general, an appropriate dosage and treatment regimen provides the modulating agent(s) in an amount sufficient to provide therapeutic and/or prophylactic benefit. Within particularly preferred embodiments of the invention, a modulating agent or pharmaceutical composition as described herein may be administered at a dosage ranging from 0.001 to 50 mg/kg body weight, preferably from 0.1 to 20 mg/kg, on a regimen of single or multiple daily doses. For topical administration, a cream typically comprises an amount of modulating agent ranging from 0.00001% to 1%, preferably 0.0001% to 0.002%. Fluid compositions typically contain about 10 ng/ml to 5 mg/ml, preferably from about 10 μg to 2 mg/mL modulating agent. Appropriate dosages may generally be determined using experimental models and/or clinical trials. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

THERAPEUTIC METHODS EMPLOYING MODULATING AGENTS

In general, the modulating agents and compositions described herein may be used for modulating the adhesion of cadherin-expressing cells (i.e., cells that express one or more of E-cadherin, N-cadherin, P-cadherin, R-cadherin and/or other cadherin(s) containing the HAV-BM sequence, including as yet undiscovered cadherins). Such modulation may be performed in vitro and/or in vivo, preferably in a mammal such as a human. As noted above, modulating agents for purposes that involve the disruption of cadherin-mediated cell adhesion may comprise an HAV-BM sequence, multiple HAV-BM sequences in close proximity and/or an antibody (or an antigen-binding fragment thereof) that recognizes an HAV-BM sequence. When it is desirable to also disrupt cell adhesion mediated by other adhesion molecules, a modulating agent may additionally comprise one or more CAR sequences bound by such adhesion molecules (and/or antibodies or fragments thereof that bind such sequences), preferably separated from each other and from the HAV-BM sequence by linkers. As noted above, such linkers may or may not comprise one or more amino acids. For enhancing cell adhesion, a modulating agent may contain multiple HAV-BM sequences or antibodies (or fragments), preferably separated by linkers, and/or may be linked to a single molecule or to a support material as described above.

Certain methods involving the disruption of cell adhesion as described herein have an advantage over prior techniques in that they permit the passage of molecules that are large and/or charged across barriers of cadherin-expressing cells. As described in greater detail below, modulating agents as described herein may also be used to disrupt or enhance cell adhesion in a variety of other contexts. Within each of the methods described herein, one or more modulating agents may generally be administered alone, or within a pharmaceutical composition. In each specific method described herein, as noted above, a targeting agent may be employed to increase the local concentration of modulating agent at the target site.

In general, within methods for modulating cell adhesion, a cadherin-expressing cell is contacted with a modulating agent under conditions and for a time sufficient to permit inhibition or enhancement of a cadherin-mediated function. Cadherin-expressing cells include, but are not limited to, epithelial cells, endothelial cells, neural cells, tumor cells and lymphocytes. Such contact may be achieved in vitro, or in vivo by administration of a pharmaceutical composition as provided herein.

Within certain aspects, methods are provided in which cell adhesion is diminished. In one such aspect, the present invention provides methods for reducing unwanted cellular adhesion by administering a modulating agent as described herein. Unwanted cellular adhesion can occur between tumor cells, between tumor cells and normal cells or between normal cells as a result of surgery, injury, chemotherapy, disease, inflammation or other condition jeopardizing cell viability or function. Preferred modulating agents for use within such methods include those comprising one or more of the sequences INPISGQ (SEQ ID NO:22), LNPISGQ (SEQ ID NO:23), IDPVSGQ (SEQ ID NO:24), KIDPVNGQ (SEQ ID NO:25), PISGQ (SEQ ID NO:26), KIDPVN (SEQ ID NO:50), <u>PVNGQ</u> (SEQ ID NO:51), <u>PISGQ</u> (SEQ ID NO:52), <u>PVSGR</u> (SEQ ID NO:53), <u>KIDPV</u> (SEQ ID NO:54), <u>KIDPVN</u> (SEQ ID NO:55), <u>IDPVN</u> (SEQ ID NO:56), <u>INPIS</u> (SEQ ID NO:57), <u>CPVNGQC</u> (SEQ ID NO:58), <u>CPISGQC</u> (SEQ ID NO:59), <u>CPVSGRC</u> (SEQ ID NO:60), <u>CKIDPVNC</u> (SEQ ID NO:61), <u>CIDPVNC</u> (SEQ ID NO:62), <u>CINPISC</u> (SEQ ID NO:63) or <u>CKIDPVC</u> (SEQ ID NO:85), in which cyclization is indicated by an underline. Modulating agents may alternatively, or in addition, comprise a derivative of one of the foregoing sequences. In addition, a modulating agent may comprise the sequence RGD, which is bound by integrins, the sequence LYHY (SEQ ID NO:70), which is bound by occludin, and/or one or more of the sequences HAV, YAT, FAT, YAS or RAL. Preferably, such sequences are separated from the HAV-BM sequence via a linker. Alternatively, a separate modulator of cell adhesion (e.g., integrin- and/or occludin-mediated) may be administered in conjunction with the modulating agent (s), either within the same pharmaceutical composition or separately. Topical administration of the modulating agent (s) is generally preferred, but other means may also be employed. Preferably, a fluid composition for topical administration (comprising, for example, physiological saline) comprises an amount of modulating agent as described above, and more preferably from 10 µg/mL to 1 mg/mL. Creams may generally be formulated as described above. Topical administration in the surgical field may be given once at the end of surgery by irrigation of the wound or as an intermittent or continuous irrigation with the use of surgical drains in the post-operative period or by the use of drains specifically inserted in an area of inflammation, injury or disease in cases where surgery does not need to be performed. Alternatively, parenteral or transcutaneous administration may be used to achieve similar results.

Within another such aspect, methods are provided for enhancing the delivery of a drug through the skin of a mammal. Transdermal delivery of drugs is a convenient and non-invasive method that can be used to maintain relatively constant blood levels of a drug. In general, to facilitate drug delivery via the skin, it is necessary to perturb adhesion between the epithelial cells (keratinocytes) and the endothelial cells of the microvasculature. Using currently available techniques, only small, uncharged molecules may be delivered across skin in vivo. The methods described herein are not subject to the same degree of limitation. Accordingly, a wide variety of drugs may be transported across the epithelial and endothelial cell layers of skin, for systemic or topical administration. Such drugs may be delivered to melanomas or may enter the blood stream of the mammal for delivery to other sites within the body.

To enhance the delivery of a drug through the skin, a modulating agent as described herein and a drug are contacted with the skin surface. Preferred modulating agents for use within such methods include those comprising one or more of the sequences INPISGQ (SEQ ID NO:22), LNPISGQ (SEQ ID NO:23), IDPVSGQ (SEQ ID NO:24), KIDPVNGQ (SEQ ID NO:25), PISGQ (SEQ ID NO:26), KIDPVN (SEQ ID NO:50), PVNGQ (SEQ ID NO:51), PISGQ (SEQ ID NO:52), PVSGR (SEQ ID NO:53), KIDPV (SEQ ID NO:54), KIDPVN (SEQ ID NO:55), IDPVN (SEQ ID NO:56), INPIS (SEQ ID NO:57), CPVNGQC (SEQ ID NO:58), CPISGQC (SEQ ID NO:59), CPVSGRC (SEQ ID NO:60), CKIDPVNC (SEQ ID NO:61), CIDPVNC (SEQ ID NO:62), CINPISC (SEQ ID NO:63) or CKIDPVC (SEQ ID NO:85), in which cyclization is indicated by an underline. Modulating agents may alternatively, or in addition, comprise a derivative of one of the foregoing sequences. Multifunctional modulating agents comprising the cadherin CAR sequence HAV-BM linked to one or more of the Dsc CAR sequences YAT, FAT and YAS and/or the Dsg CAR sequence RAL may also be used to disrupt epithelial cell adhesion. Such modulating agents may also, or alternatively, comprise the fibronectin CAR sequence RGD, which is recognized by integrins, and/or the occludin CAR sequence LYHY (SEQ ID NO:70). Alternatively, a separate modulator of cell adhesion may be administered in conjunction with the modulating agent(s), either within the same pharmaceutical composition or separately.

Contact may be achieved by direct application of the modulating agent, generally within a composition formulated as a cream or gel, or using any of a variety of skin contact devices for transdermal application (such as those described in European Patent Application No. 566,816 A; U.S. Pat. No. 5,613,958; U.S. Pat. No. 5,505,956). A skin patch provides a convenient method of administration (particularly for slow-release formulations). Such patches may contain a reservoir of modulating agent and drug separated from the skin by a membrane through which the drug diffuses. Within other patch designs, the modulating agent and drug may be dissolved or suspended in a polymer or adhesive matrix that is then placed in direct contact with the patient's skin. The modulating agent and drug may then diffuse from the matrix into the skin. Modulating agent(s) and drug(s) may be contained within the same composition or skin patch, or may be separately administered, although administration at the same time and site is preferred. In general, the amount of modulating agent administered via the skin varies with the nature of the condition to be treated or prevented, but may vary as described above. Such levels may be achieved by appropriate adjustments to the device used, or by applying a cream formulated as described above. Transfer of the drug across the skin and to the target tissue may be predicted based on in vitro studies using, for example, a Franz cell apparatus, and evaluated in vivo by appropriate means that will be apparent to those of ordinary skill in the art. As an example, monitoring of the serum level of the administered drug over time provides an easy measure of the drug transfer across the skin.

Transdermal drug delivery as described herein is particularly useful in situations in which a constant rate of drug delivery is desired, to avoid fluctuating blood levels of a drug. For example, morphine is an analgesic commonly used immediately following surgery. When given intermittently in a parenteral form (intramuscular, intravenous), the patient usually feels sleepy during the first hour, is well during the next 2 hours and is in pain during the last hour because the blood level goes up quickly after the injection and goes down below the desirable level before the 4 hour interval prescribed for re-injection is reached. Transdermal administration as described herein permits the maintenance of constant levels for long periods of time (e.g., days), which allows adequate pain control and mental alertness at the same time. Insulin provides another such example. Many diabetic patients need to maintain a constant baseline level of insulin which is different from their needs at the time of meals. The baseline level may be maintained using transdermal administration of insulin, as described herein. Antibiotics may also be administered at a constant rate, maintaining adequate bactericidal blood levels, while avoiding the high levels that are often responsible for the toxicity (e.g., levels of gentamycin that are too high typically result in renal toxicity).

Drug delivery by the methods of the present invention also provide a more convenient method of drug administration. For example, it is often particularly difficult to administer parenteral drugs to newborns and infants because of the difficulty associated with finding veins of acceptable caliber to catheterize. However, newborns and infants often have a relatively large skin surface as compared to adults. Transdermal drug delivery permits easier management of such patients and allows certain types of care that can presently be given only in hospitals to be given at home. Other patients who typically have similar difficulties with venous catheterization are patients undergoing chemotherapy or patients on dialysis. In addition, for patients undergoing prolonged therapy, transdermal administration as described herein is more convenient than parenteral administration.

Transdermal administration as described herein also allows the gastrointestinal tract to be bypassed in situations where parenteral uses would not be practical. For example, there is a growing need for methods suitable for administration of therapeutic small peptides and proteins, which are typically digested within the gastrointestinal tract. The methods described herein permit administration of such compounds and allow easy administration over long periods of time. Patients who have problems with absorption through their gastrointestinal tract because of prolonged ileus or specific gastrointestinal diseases limiting drug absorption may also benefit from drugs formulated for transdermal application as described herein.

Further, there are many clinical situations where it is difficult to maintain compliance. For example, patients with mental problems (e.g., patients with Alzheimer's disease or psychosis) are easier to manage if a constant delivery rate of drug is provided without having to rely on their ability to take their medication at specific times of the day. Also patients who simply forget to take their drugs as prescribed are less likely to do so if they merely have to put on a skin patch periodically (e.g., every 3 days). Patients with diseases that are without symptoms, like patients with hypertension, are especially at risk of forgetting to take their medication as prescribed.

For patients taking multiple drugs, devices for transdermal application such as skin patches may be formulated with combinations of drugs that are frequently used together. For example, many heart failure patients are given digoxin in combination with furosemide. The combination of both drugs into a single skin patch facilitates administration, reduces the risk of errors (taking the correct pills at the appropriate time is often confusing to older people), reduces the psychological strain of taking "so many pills," reduces skipped dosage because of irregular activities and improves compliance.

The methods described herein are particularly applicable to humans, but also have a variety of veterinary uses, such as the administration of growth factors or hormones (e.g., for fertility control) to an animal.

As noted above, a wide variety of drugs may be administered according to the methods provided herein. Some examples of drug categories that may be administered transdermally include anti-inflammatory drugs (e.g., in arthritis and in other condition) such as all NSAID, indomethacin, prednisone, etc.; analgesics (especially when oral absorption is not possible, such as after surgery, and when parenteral administration is not convenient or desirable), including morphine, codeine, Demerol, acetaminophen and combinations of these (e.g., codeine plus acetaminophen); antibiotics such as Vancomycin (which is not absorbed by the GI tract and is frequently given intravenously) or a combination of INH and Rifampicin (e.g, for tuberculosis); anticoagulants such as heparin (which is not well absorbed by the GI tract and is generally given parenterally, resulting in fluctuation in the blood levels with an increased risk of bleeding at high levels and risks of inefficacy at lower levels) and Warfarin (which is absorbed by the GI tract but cannot be administered immediately after abdominal surgery because of the normal ileus following the procedure); antidepressants (e.g., in situations where compliance is an issue as in Alzheimer's disease or when maintaining stable blood levels results in a significant reduction of anti-cholinergic side effects and better tolerance by patients), such as amitriptylin, imipramin, prozac, etc.; antihypertensive drugs (e.g., to improve compliance and reduce side effects associated with fluctuating blood levels), such as diuretics and beta-blockers (which can be administered by the same patch; e.g, furosemide and propanolol); antipsychotics (e.g., to facilitate compliance and make it easier for care giver and family members to make sure that the drug is received), such as haloperidol and chlorpromazine; and anxiolytics or sedatives (e.g., to avoid the reduction of alertness related to high blood levels after oral administration and allow a continual benefit throughout the day by maintaining therapeutic levels constant).

Numerous other drugs may be administered as described herein, including naturally occurring and synthetic hormones, growth factors, proteins and peptides. For example, insulin and human growth hormone, growth factors like erythropoietin, interleukins and inteferons may be delivered via the skin.

Kits for administering a drug via the skin of a mammal are also provided within the present invention. Such kits generally comprise a device for transdermal application (e.g., a skin patch) in combination with, or impregnated with, one or more modulating agents. A drug may additionally be included within such kits.

Within a related aspect, the use of modulating agents as described herein to increase the permeability of endothelial and epithelial cell layers, thereby facilitating sampling of the blood compartment by passive diffusion. Such methods permit the detection and/or measurement of the levels of specific molecules circulating in the blood. In general, to sample the blood compartment, it is necessary to perturb adhesion between the epithelial cells (keratinocytes) and the endothelial cells of the microvasculature. Using currently available techniques, only small, uncharged molecules may be detected across skin in vivo. The methods described herein are not subject to the same degree of limitation. Accordingly, a wide variety of blood components may be sampled across epithelial and endothelial cell layers. Such sampling may be achieved across any such cell layers, including skin and gums.

For example, application of one or more modulating agents to the skin, via a skin patch as described herein, permits the patch to function like a sponge to accumulate a small quantity of fluid containing a representative sample of the serum. The patch is then removed after a specified amount of time and analyzed by suitable techniques for the compound of interest (e.g., a medication, hormone, growth factor, metabolite or marker). Alternatively, a patch may be impregnated with reagents to permit a color change if a specific substance (e.g., an enzyme) is detected. Substances that can be detected in this manner include, but are not limited to, illegal drugs such as cocaine, HIV enzymes, glucose and PSA. This technology is of particular benefit for home testing kits.

To facilitate sampling of blood in a patient, a modulating agent as described herein is contacted with the skin surface. Multifunctional modulating agents comprising an HAV-BM sequence linked to one or more of the OB-cadherin CAR sequence DDK, the Dsc CAR sequences YAT, FAT and YAS and/or the Dsg CAR sequence RAL may also be used to disrupt epithelial cell adhesion. Such modulating agents may also, or alternatively, comprise the fibronectin CAR sequence RGD, which is recognized by integrins, and/or the occludin CAR sequence LYHY (SEQ ID NO:70). Alternatively, a separate modulator of non-classical cadherin-mediated cell adhesion may be administered in conjunction with the modulating agent(s), either within the same pharmaceutical composition or separately.

Contact may be achieved as described herein for transdermal drug delivery. Modulating agent(s) and reagents for assaying blood components may, but need not, be contained within the same composition or skin patch. In general, the amount of modulating agent administered via the skin may vary as described above. Such levels may be achieved by appropriate adjustments to the device used, or by applying a cream formulated as described above. Transfer of the blood component across the skin may be predicted based on in vitro studies using, for example, a Franz cell apparatus, and evaluated in vivo by appropriate means that will be apparent to those of ordinary skill in the art.

Kits for sampling blood component via, for example, the skin or gums of a mammal, are also provided within the present invention. Such kits generally comprise a device for transdermal application (i.e., skin patch) in combination with, or impregnated with, one or more modulating agents. A reagent for detection of a blood component may additionally be included within such kits.

Within a further aspect, methods are provided for enhancing delivery of a drug to a tumor in a mammal, comprising administering a modulating agent in combination with a drug to a tumor-bearing mammal. Modulating agents for use within such methods include those designed to disrupt E-cadherin and/or N-cadherin mediated cell adhesion, such as those comprising one or more of the sequences INPISGQ (SEQ ID NO:22), LNPISGQ (SEQ ID NO:23), IDPVSGQ (SEQ ID NO:24), KIDPVNGQ (SEQ ID NO:25), PISGQ (SEQ ID NO:26), KIDPVN (SEQ ID NO:50), PVNGQ (SEQ ID NO:51), PISGQ (SEQ ID NO:52), PVSGR (SEQ ID NO:53), KIDPV (SEQ ID NO:54), KIDPVN (SEQ ID NO:55), IDPVN (SEQ ID NO:56), INPIS (SEQ ID NO:57), CPVNGQC (SEQ ID NO:58), CPISGQC (SEQ ID NO:59), CPVSGRC (SEQ ID NO:60), CKIDPVNC (SEQ ID NO:61), CIDPVNC (SEQ ID NO:62), CINPISC (SEQ ID NO:63) or CKIDPVC (SEQ ID NO:85), in which cyclization is indicated by an underline. Modulating agents may alternatively, or in addition, comprise a derivative of one of the foregoing sequences. Bi-functional modulating agents that comprise an HAV-BM sequence with flanking E-cadherin-specific sequences joined via a linker to an HAV-BM sequence with flanking N-cadherin-specific sequences are also preferred. Preferably, the peptide portion(s) of a modulating agent comprises 6–16 amino acids, since longer peptides are difficult to dissolve in aqueous solution and are more likely to be degraded by peptidases.

In one particularly preferred embodiment, a modulating agent is capable of disrupting cell adhesion mediated by multiple adhesion molecules. For example, a single branched modulating agent (or multiple agents linked to a single molecule or support material) may disrupt E-cadherin, N-cadherin, occludin, Dsc and Dsg mediated cell adhesion, thereby disrupting adherens junctions, tight junctions and desmosomes. Such an agent may comprise one or more of the HAV-BM sequence, as well as the putative Dsc CAR sequences YAT, FAT, and YAS; the putative Dsg CAR sequence RAL; the OB-cadherin CAR sequence DKK; and the occludin CAR sequence GVNPTAQSSGSLYGSQIYALCNQFYT-PAATGLYVDQYLYHYCVVDPQE (SEQ ID NO:69) or a derivative thereof such as LYHY (SEQ ID NO:70). Such agents serve as multifunctional disrupters of cell adhesion. Alternatively, a separate modulator of non-classical cadherin-mediated cell adhesion may be administered in conjunction with the modulating agent(s), either within the same pharmaceutical composition or separately. Preferred antibody modulating agents include Fab fragments directed against either the N-cadherin HAV-BM sequence or E-cadherin HAV-BM sequence. Fab fragments directed against the occludin CAR sequence GVNPTAQSSGSLYGSQIYALCNQFYTPAATGLYVDQYLYHYCVVDPQE (SEQ ID NO:69) may also be employed, either incorporated into a modulating agent or within a separate modulator that is administered concurrently.

Preferably, the modulating agent and the drug are formulated within the same composition or drug delivery device prior to administration. In general, a modulating agent may enhance drug delivery to any tumor, and the method of administration may be chosen based on the type of target tumor. For example, injection or topical administration as described above may be preferred for melanomas and other accessible tumors (e.g., metastases from primary ovarian tumors may be treated by flushing the peritoneal cavity with the composition). Other tumors (e.g., bladder tumors) may be treated by injection of the modulating agent and the drug (such as mitomycin C) into the site of the tumor. In other instances, the composition may be administered systemically, and targeted to the tumor using any of a variety of specific targeting agents. Suitable drugs may be identified by those of ordinary skill in the art based upon the type of cancer to be treated (e.g., mitomycin C for bladder cancer). In general, the amount of modulating agent administered varies with the method of administration and the nature of the tumor, within the typical ranges provided above, preferably ranging from about 1 $\mu$g/mL to about 2 mg/mL, and more preferably from about 10 $\mu$g/mL to 1 mg/mL. Transfer of the drug to the target tumor may be evaluated by appropriate means that will be apparent to those of ordinary skill in the art. Drugs may also be labeled (e.g., using radionuclides) to permit direct observation of transfer to the target tumor using standard imaging techniques.

Within a related aspect, the present invention provides methods for treating cancer and/or inhibiting metastasis in a mammal. Cancer tumors are solid masses of cells, growing out of control, which require nourishment via blood vessels. The formation of new capillaries is a prerequisite for tumor growth and the emergence of metastases. Administration of modulating agents as described herein may disrupt the growth of such blood vessels, thereby providing effective therapy for the cancer and/or inhibiting metastasis. Modulating agents may also be used to treat leukemias. Preferred modulating agents for use within such methods include those that disrupt N-cadherin and/or E-cadherin mediated cell adhesion, such as those comprising one or more of the sequences INPISGQ (SEQ ID NO:22), LNPISGQ (SEQ ID NO:23), IDPVSGQ (SEQ ID NO:24), KIDPVNGQ (SEQ ID NO:25), PISGQ (SEQ ID NO:26), KIDPVN (SEQ ID NO:50), <u>PVNGQ</u> (SEQ ID NO:51), <u>PISGQ</u> (SEQ ID NO:52), <u>PVSGR</u> (SEQ ID NO:53), <u>KIDPV</u> (SEQ ID NO:54), <u>KIDPVN</u> (SEQ ID NO:55), <u>IDPVN</u> (SEQ ID NO:56), <u>INPIS</u> (SEQ ID NO:57), <u>CPVNGQC</u> (SEQ ID NO:58), <u>CPISGQC</u> (SEQ ID NO:59), <u>CPVSGRC</u> (SEQ ID NO:60), <u>CKIDPVNC</u> (SEQ ID NO:61), <u>CIDPVNC</u> (SEQ ID NO:62), <u>CINPISC</u> (SEQ ID NO:63) or <u>CKIDPVC</u> (SEQ ID NO:85), in which cyclization is indicated by an underline. Modulating agents may alternatively, or in addition, comprise a derivative of one of the foregoing sequences. Preferably, the peptide portion(s) of such modulating agents comprise 6–16 amino acids. In addition, a modulating agent may comprise the sequence RGD, which is recognized by integrins, the occludin CAR sequence LYHY (SEQ ID NO:70), the OB-cadherin CAR sequence DKK and/or one or more of the putative Dsc CAR sequences YAT, FAT, and YAS; the putative Dsg CAR sequence RAL; and the occludin CAR sequence GVNPTAQSSGSLYGSQIYALCNQFYTPAATGLYVDQYLYHYCVVDPQE (SEQ ID NO:69) or a derivative thereof such as LYHY (SEQ ID NO:70). Preferably such sequences are separated from the HAV-BM sequence via a linker. Alternatively, a separate modulator of integrin- and/or occludin-mediated cell adhesion may be administered in conjunction with the modulating agents(s), either within the same pharmaceutical composition or separately.

A modulating agent may be administered alone (e.g., via the skin) or within a pharmaceutical composition. For melanomas and certain other accessible tumors, injection or topical administration as described above may be preferred. For ovarian cancers, flushing the peritoneal cavity with a composition comprising one or more modulating agents may prevent metastasis of ovarian tumor cells. Other tumors (e.g., bladder tumors, bronchial tumors or tracheal tumors) may be treated by injection of the modulating agent into the cavity. In other instances, the composition may be administered systemically, and targeted to the tumor using any of a variety of specific targeting agents, as described above. In general, the amount of modulating agent administered varies depending upon the method of administration and the nature of the cancer, but may vary within the ranges identified above. The effectiveness of the cancer treatment or inhibition of metastasis may be evaluated using well known clinical observations, such as the level of serum tumor markers (e.g., CEA or PSA).

In yet another related aspect, the present invention provides methods for inducing apoptosis in a cadherin-expressing cell. In general, patients afflicted with cancer may benefit from such treatment. Certain preferred modulating agents for use within such methods comprise one or more of the sequences INPISGQ (SEQ ID NO:22), LNPISGQ (SEQ ID NO:23), IDPVSGQ (SEQ ID NO:24), KIDPVNGQ (SEQ ID NO:25), PISGQ (SEQ ID NO:26), KIDPVN (SEQ ID NO:50), PVNGQ (SEQ ID NO:51), PISGQ (SEQ ID NO:52), PVSGR (SEQ ID NO:53), KIDPV (SEQ ID NO:54), KIDPVN (SEQ ID NO:55), IDPVN (SEQ ID NO:56), INPIS (SEQ ID NO:57), CPVNGQC (SEQ ID NO:58), CPISGQC (SEQ ID NO:59), CPVSGRC (SEQ ID NO:60), CKIDPVNC (SEQ ID NO:61), CIDPVNC (SEQ ID NO:62), CINPISC (SEQ ID NO:63) or CKIDPVC (SEQ ID NO:85), in which cyclization is indicated by an underline. Modulating agents may alternatively, or in addition, comprise a derivative of one of the foregoing sequences. Modulating agents comprising an additional CAR sequence (e.g., HAV, RGD, YAT, FAT, YAS, RAL and/or LYHY (SEQ ID NO:70) are also preferred. As noted above, such additional sequences may be separated from the HAV-BM sequence via a linker. Alternatively, a separate modulator of integrin-mediated cell adhesion may be administered in conjunction with the modulating agent(s), either within the same pharmaceutical composition or separately. Administration may be topical, via injection or by other means, and the addition of a targeting agent may be beneficial, particularly when the administration is systemic. Suitable modes of administration and dosages depend upon the location and nature of the cells for which induction of apoptosis is desired but, in general, dosages may vary as described above. A biopsy may be performed to evaluate the level of induction of apoptosis.

Within a further related aspect, a modulating agent may be used to inhibit angiogenesis (i.e., the growth of blood vessels from pre-existing blood vessels) in a mammal. Inhibition of angiogenesis may be beneficial, for example, in patients afflicted with diseases such as cancer or arthritis. Preferred modulating agents for inhibition of angiogenesis include those comprising one or more of the sequences INPISGQ (SEQ ID NO:22), LNPISGQ (SEQ ID NO:23), IDPVSGQ (SEQ ID NO:24), KIDPVNGQ (SEQ ID NO:25), PISGQ (SEQ ID NO:26), KIDPVN (SEQ ID NO:50), PVNGQ (SEQ ID NO:51), PISGQ (SEQ ID NO:52), PVSGR (SEQ ID NO:53), KIDPV (SEQ ID NO:54), KIDPVN (SEQ ID NO:55), IDPVN (SEQ ID NO:56), INPIS (SEQ ID NO:57), CPVNGQC (SEQ ID NO:58), CPISGQC (SEQ ID NO:59), CPVSGRC (SEQ ID NO:60), CKIDPVNC (SEQ ID NO:61), CIDPVNC (SEQ ID NO:62), CINPISC (SEQ ID NO:63) or CKIDPVC (SEQ ID NO:85), in which cyclization is indicated by an underline. Modulating agents may alternatively, or in addition, comprise a derivative of one of the foregoing sequences. In addition, a modulating agent for use in inhibiting angiogenesis may comprise the sequence RGD, which is recognized by integrins, the OB-cadherin CAR sequence DKK, and/or the occludin CAR sequence LYHY (SEQ ID NO:70), separated from the HAV-BM sequence via a linker. Alternatively, a separate modulator of integrin- or occludin-mediated cell adhesion may be administered in conjunction with the modulating agent(s), either within the same pharmaceutical composition or separately.

The effect of a particular modulating agent on angiogenesis may generally be determined by evaluating the effect of the agent on blood vessel formation. Such a determination may generally be performed, for example, using a chick chorioallantoic membrane assay (Iruela-Arispe et al., *Molecular Biology of the Cell* 6:327–343, 1995). Briefly, a modulating agent may be embedded in a mesh composed of vitrogen at one or more concentrations (e.g., ranging from about 1 to 100 μg/mesh). The mesh(es) may then be applied to chick chorioallantoic membranes. After 24 hours, the effect of the modulating agent may be determined using computer assisted morphometric analysis. A modulating agent should inhibit angiogenesis by at least 25% at a concentration of 33 μg/mesh.

The addition of a targeting agent as described above may be beneficial, particularly when the administration is systemic. Suitable modes of administration and dosages depend upon the condition to be prevented or treated but, in general, administration by injection is appropriate. Dosages may vary as described above. The effectiveness of the inhibition may be evaluated grossly by assessing the inability of the tumors to maintain their growth and microscopically by observing an absence of nerves at the periphery of the tumor.

The present invention also provides methods for enhancing drug delivery to the central nervous system of a mammal. The blood/brain barrier is largely impermeable to most neuroactive agents, and delivery of drugs to the brain of a mammal often requires invasive procedures. Using a modulating agent as described herein, however, delivery may be by, for example, systemic administration of a modulating agent-drug-targeting agent combination, injection of a modulating agent (alone or in combination with a drug and/or targeting agent) into the carotid artery or application of a skin patch comprising a modulating agent to the head of the patient. Certain preferred modulating agents for use within such methods comprise one or more of the sequences INPISGQ (SEQ ID NO:22), LNPISGQ (SEQ ID NO:23), IDPVSGQ (SEQ ID NO:24), KIDPVNGQ (SEQ ID NO:25), PISGQ (SEQ ID NO:26), KIDPVN (SEQ ID NO:50), PVNGQ (SEQ ID NO:51), PISGQ (SEQ ID NO:52), PVSGR (SEQ ID NO:53), KIDPV (SEQ ID NO:54), KIDPVN (SEQ ID NO:55), IDPVN (SEQ ID NO:56), INPIS (SEQ ID NO:57), CPVNGQC (SEQ ID NO:58), CPISGQC (SEQ ID NO:59), CPVSGRC (SEQ ID NO:60), CKIDPVNC (SEQ ID NO:61), CIDPVNC (SEQ ID NO:62), CINPISC (SEQ ID NO:63) or CKIDPVC (SEQ ID NO:85), in which cyclization is indicated by an underline. Modulating agents may alternatively, or in addition, comprise a derivative of one of the foregoing sequences. Also preferred are bi-functional modulating agents comprising an HAV-BM sequence and an occludin CAR sequence G V N P T A Q S S G S L Y G S Q I Y A L C N Q F Y T- PAATGLYVDQYLYHYCVVDPQE (SEQ ID NO:69), or derivatives or portions thereof such as LYHY (SEQ ID NO:70), preferably joined by a linker. Alternatively, a separate modulator of occludin-mediated cell adhesion may be administered in conjunction with the modulating agent(s), either within the same pharmaceutical composition or separately. Preferably, the peptide portion(s) of such modulating agents comprise 6–16 amino acids. Modulating agents may further comprise antibodies or Fab fragments directed against an N-cadherin HAV-BM sequence. Fab fragments directed against the occludin CAR sequence GVNPTAQSSGSLYGSQIYALCNQFYT-PAATGLYVDQYLYHYCVVDPQE (SEQ ID NO:69) may also be employed, either incorporated into the modulating agent or administered concurrently as a separate modulator.

In general, the amount of modulating agent administered varies with the method of administration and the nature of the condition to be treated or prevented, but typically varies as described above. Transfer of the drug to the central nervous system may be evaluated by appropriate means that will be apparent to those of ordinary skill in the art, such as magnetic resonance imaging (MRI) or PET scan (positron emitted tomography).

In certain other aspects, the present invention provides methods for enhancing adhesion of cadherin-expressing cells. Within certain embodiments, a modulating agent may be linked to a solid support, resulting in a matrix that comprises multiple modulating agents. Within one such embodiment, the support is a polymeric matrix to which modulating agents and molecules comprising other CAR sequence(s) are attached (e.g., modulating agents and molecules comprising an RGD sequence may be attached to the same matrix, preferably in an alternating pattern). Such matrices may be used in contexts in which it is desirable to enhance adhesion mediated by multiple cell adhesion molecules. Alternatively, the modulating agent itself may comprise multiple HAV-BM sequences or antibodies (or fragments thereof), separated by linkers as described above. Either way, the modulating agent(s) function as a "biological glue" to bind multiple cadherin-expressing cells within a variety of contexts.

Within one aspect, such modulating agents may be used to enhance wound healing and/or reduce scar tissue in a mammal. Peptides that may be linked to a support, and/or to one another via a linker, to generate a suitable modulating agent include, but are not limited to, those comprising one or more of the sequences INPISGQ (SEQ ID NO:22), LNPISGQ (SEQ ID NO:23), IDPVSGQ (SEQ ID NO:24), KIDPVNGQ (SEQ ID NO:25), PISGQ (SEQ ID NO:26), KIDPVN (SEQ ID NO:50), PVNGQ (SEQ ID NO:51), PISGQ (SEQ ID NO:52), PVSGR (SEQ ID NO:53), KIDPV (SEQ ID NO:54), KIDPVN (SEQ ID NO:55), IDPVN (SEQ ID NO:56), INPIS (SEQ ID NO:57), CPVNGQC (SEQ ID NO:58), CPISGQC (SEQ ID NO:59), CPVSGRC (SEQ ID NO:60), CKIDPVNC (SEQ ID NO:61), CIDPVNC (SEQ ID NO:62), CINPISC (SEQ ID NO:63) or CKIDPVC (SEQ ID NO:85), in which cyclization is indicated by an underline. Modulating agents may alternatively, or in addition, comprise a derivative of one of the foregoing sequences. Modulating agents that are linked to a biocompatible and biodegradable matrix such as cellulose or collagen are particularly preferred. For use within such methods, a modulating agent should have a free amino or hydroxyl group. Multi-functional modulating agents comprising the HAV-BM sequence, the fibronectin CAR sequence RGD, which is recognized by integrins, the OB-cadherin CAR sequence DKK, and/or the putative Dsc and Dsg CAR sequences YAT, FAT, YAS and RAL may also be used as potent stimulators of wound healing and/or to reduce scar tissue. Such agents may also, or alternatively, comprise the occludin CAR sequence LYHY (SEQ ID NO:70). Alternatively, one or more separate modulator of integrin-, Dsc-, Dsg- and/or occludin-mediated cell adhesion may be administered in conjunction with the modulating agent(s), either within the same pharmaceutical composition or separately.

The modulating agents are generally administered topically to the wound, where they may facilitate closure of the wound and may augment, or even replace, stitches. Similarly, administration of matrix-linked modulating agents may facilitate cell adhesion in foreign tissue implants (e.g., skin grafting and prosthetic implants) and may prolong the duration and usefulness of collagen injection. In general, the amount of matrix-linked modulating agent administered to a wound, graft or implant site varies with the severity of the wound and/or the nature of the wound, graft, or implant, but may vary as discussed above.

Within another aspect, one or more modulating agents may be linked to the interior surface of a tissue culture plate or other cell culture support, such as for use in a bioreactor. Such linkage may be performed by any suitable technique, as described above. Modulating agents linked in this fashion may generally be used to immobilize cadherin-expressing cells. For example, dishes or plates coated with one or more modulating agents may be used to immobilize cadherin-expressing cells within a variety of assays and screens. Within bioreactors (i.e., systems for large scale production of cells or organoids), modulating agents may generally be used to improve cell attachment and stabilize cell growth. Modulating agents may also be used within bioreactors to support the formation and function of highly differentiated organoids derived, for example, from dispersed populations of fetal mammalian cells. Bioreactors containing biomatrices of modulating agent(s) may also be used to facilitate the production of specific proteins.

Modulating agents as described herein may be used within a variety of bioreactor configurations. In general, a bioreactor is designed with an interior surface area sufficient to support large numbers of adherent cells. This surface area can be provided using membranes, tubes, microtiter wells, columns, hollow fibers, roller bottles, plates, dishes, beads or a combination thereof. A bioreactor may be compartmentalized. The support material within a bioreactor may be any suitable material known in the art; preferably, the support material does not dissolve or swell in water. Preferred support materials include, but are not limited to, synthetic polymers such as acrylics, vinyls, polyethylene, polypropylene, polytetrafluoroethylene, nylons, polyurethanes, polyamides, polysulfones and poly(ethylene terephthalate); ceramics; glass and silica.

The present invention also provides, within further aspects, methods for enhancing and/or directing neurological growth. In one such aspect, neurite outgrowth may be enhanced and/or directed by contacting a neuron with one or more modulating agents. Preferred modulating agents for use within such methods are linked to a polymeric matrix or other support and/or contain multiple HAV-BM sequences separated by one or more linkers. Peptides that may be linked to a support material (and/or to one another via a linker to generate a suitable modulating agent) include, but are not limited to, those comprising one or more of the sequences INPISGQ (SEQ ID NO:22), LNPISGQ (SEQ ID NO:23), IDPVSGQ (SEQ ID NO:24), KIDPVNGQ (SEQ ID NO:25), PISGQ (SEQ ID NO:26), KIDPVN (SEQ ID NO:50), PVNGQ (SEQ ID NO:51), PISGQ (SEQ ID NO:52), PVSGR (SEQ ID NO:53), KIDPV (SEQ ID NO:54), KIDPVN (SEQ ID NO:55), IDPVN (SEQ ID NO:56), INPIS (SEQ ID NO:57), CPVNGQC (SEQ ID NO:58), CPISGQC (SEQ ID NO:59), CPVSGRC (SEQ ID NO:60), CKIDPVNC (SEQ ID NO:61), CIDPVNC (SEQ ID NO:62), CINPISC (SEQ ID NO:63) or CKIDPVC (SEQ ID NO:85), in which cyclization is indicated by an underline. Certain preferred modulating agents comprise one or more of N-Ac-INPISGQ-NH$_2$ (SEQ ID NO:22), H-INPISGQ-OH (SEQ ID NO:22), N-Ac-NLKIDPVNGQI-NH$_2$ (SEQ ID NO:20), H-WLKIDPVNGQI-OH (SEQ ID NO:13), H-LKIDPVNGQI-OH (SEQ ID NO:21), H-LKIDPANGQI-OH (SEQ ID NO:64) or H-LKIDAVNGQI-OH (SEQ ID NO:65).

Modulating agents may alternatively, or in addition, comprise a derivative of one of the foregoing sequences. In addition, a modulating agent comprising HAV, RGD and/or YIGSR (SEQ ID NO:66), which are bound by integrins, and/or the N-CAM CAR sequence KYSFNYDGSE (SEQ ID NO:67) may further facilitate neurite outgrowth. Modulating agents comprising antibodies, or fragments thereof, may be used within this aspect of the present invention without the use of linkers or support materials. Preferred antibody modulating agents include Fab fragments directed against an N-cadherin HAV-BM sequence. Fab fragments directed against the N-CAM CAR sequence KYSFNYDGSE (SEQ ID NO:67) may also be employed, either incorporated into the modulating agent or administered concurrently as a separate modulator.

The method of achieving contact and the amount of modulating agent used will depend upon the location of the neuron and the extent and nature of the outgrowth desired. For example, a neuron may be contacted (e.g., via implantation) with modulating agent(s) linked to a support material such as a suture, fiber nerve guide or other prosthetic device such that the neurite outgrowth is directed along the support material. Alternatively, a tubular nerve guide may be employed, in which the lumen of the nerve guide contains a composition comprising the modulating agent(s). In vivo, such nerve guides or other supported modulating agents may be implanted using well known techniques to, for example, facilitate the growth of severed neuronal connections and/or to treat spinal cord injuries. It will be apparent to those of ordinary skill in the art that the structure and composition of the support should be appropriate for the particular injury being treated. In vitro, a polymeric matrix may similarly be used to direct the growth of neurons onto patterned surfaces as described, for example, in U.S. Pat. No. 5,510,628.

Within another aspect, one or more modulating agents may be used for therapy of a demyelinating neurological disease in a mammal. There are a number of demyelinating diseases, such as multiple sclerosis, characterized by oligodendrocyte death. Since Schwann cell migration on astrocytes is inhibited by N-cadherin, modulating agents that disrupt N-cadherin mediated cell adhesion as described herein, when implanted with Schwann cells into the central nervous system, may facilitate Schwann cell migration and permit the practice of Schwann cell replacement therapy.

Multiple sclerosis patients suitable for treatment may be identified by criteria that establish a diagnosis of clinically definite or clinically probable MS (see Poser et al., *Ann. Neurol.* 13:227, 1983). Candidate patients for preventive therapy may be identified by the presence of genetic factors, such as HLA-type DR2a and DR2b, or by the presence of early disease of the relapsing remitting type.

Schwann cell grafts may be implanted directly into the brain along with the modulating agent(s) using standard techniques. Preferred peptide modulating agents for use within such methods include those comprising one or more of the sequences INPISGQ (SEQ ID NO:22), LNPISGQ (SEQ ID NO:23), IDPVSGQ (SEQ ID NO:24), KIDPVNGQ (SEQ ID NO:25), PISGQ (SEQ ID NO:26), KIDPVN (SEQ ID NO:50), PVNGQ (SEQ ID NO:51), PISGQ (SEQ ID NO:52), PVSGR (SEQ ID NO:53), KIDPV (SEQ ID NO:54), KIDPVN (SEQ ID NO:55), IDPVN (SEQ ID NO:56), INPIS (SEQ ID NO:57), CPVNGQC (SEQ ID NO:58), CPISGQC (SEQ ID NO:59), CPVSGRC (SEQ ID NO:60), CKIDPVNC (SEQ ID NO:61), CIDPVNC (SEQ ID NO:62), CINPISC (SEQ ID NO:63) or CKIDPVC (SEQ ID NO:85), in which cyclization is indicated by an underline. Modulating agents may alternatively, or in addition, comprise a derivative of one of the foregoing sequences. Modulating agents may further comprise HAV, RGD and/or YIGSR (SEQ ID NO:66), which are bound by integrins, and/or the N-CAM CAR sequence KYSFNYDGSE (SEQ ID NO:67). Preferred antibody modulating agents include Fab fragments directed against the N-cadherin CAR sequence KYSFNYDGSE (SEQ ID NO:67). Such antibodies and fragments can be prepared using standard techniques, as discussed above. Suitable amounts of modulating agent generally range as described above, preferably from about 10 µg/mL to about 1 mg/mL.

Alternatively, a modulating agent may be implanted with oligodendrocyte progenitor cells (OPs) derived from donors not afflicted with the demyelinating disease. The myelinating cell of the CNS is the oligodendrocyte. Although mature oligodendrocytes and immature cells of the oligodendrocyte lineage, such as the oligodendrocyte type 2 astrocyte progenitor, have been used for transplantation, OPs are more widely used. OPs are highly motile and are able to migrate from transplant sites to lesioned areas where they differentiate into mature myelin-forming oligodendrocytes and contribute to repair of demyelinated axons (see e.g., Groves et al., *Nature* 362:453–55, 1993; Baron-Van Evercooren et al., *Glia* 16:147–64, 1996). OPs can be isolated using routine techniques known in the art (see e.g., Milner and French-Constant, *Development* 120:3497–3506, 1994), from many regions of the CNS including brain, cerebellum, spinal cord, optic nerve and olfactory bulb. Substantially greater yields of OP's are obtained from embryonic or neonatal rather than adult tissue. OPs may be isolated from human embryonic spinal cord and cultures of neurospheres established. Human fetal tissue is a potential valuable and renewable source of donor OP's for future, long range transplantation therapies of demyelinating diseases such as MS.

OPs can be expanded in vitro if cultured as "homotypic aggregates" or "spheres" (Avellana-Adalid et al, *J. Neurosci. Res.* 45:558–70, 1996). Spheres (sometimes called "oligospheres" or "neurospheres") are formed when OPs are grown in suspension in the presence of growth factors such as PDGF and FGF. OPs can be harvested from spheres by mechanical dissociation and used for subsequent transplantation or establishment of new spheres in culture. Alternatively, the spheres themselves may be transplanted, providing a "focal reservoir" of OPs (Avellana-Adalid et al, *J. Neurosci. Res.* 45:558–70, 1996).

An alternative source of OP may be spheres derived from CNS stem cells. Recently, Reynolds and Weiss, *Dev. Biol.* 165:1–13, 1996 have described spheres formed from EGF-responsive cells derived from embryonic neuroepithelium, which appear to retain the pluripotentiality exhibited by neuroepithelium in vivo. Cells dissociated from these spheres are able to differentiate into neurons, oligodendrocytes and astrocytes when plated on adhesive substrates in the absence of EGF, suggesting that EGF-responsive cells derived from undifferentiated embryonic neuroepithelium may represent CNS stem cells (Reynolds and Weiss, *Dev. Biol.* 165:1–13, 1996). Spheres derived from CNS stem cells provide an alternative source of OP which may be manipulated in vitro for transplantation in vivo. Spheres composed of CNS stem cells may further provide a microenvironment conducive to increased survival, migration, and differentiation of the OPs in vivo.

The use of neurospheres for the treatment of MS may be facilitated by modulating agents that enhance cell migration from the spheres. In the absence of modulating agent, the cells within the spheres adhere tightly to one another and migration out of the spheres is hindered. Modulating agents that disrupt N-cadherin mediated cell adhesion as described herein, when injected with neurospheres into the central nervous system, may improve cell migration and increase the efficacy of OP replacement therapy.

Neurosphere grafts may be implanted directly into the central nervous system along with the modulating agent(s) using standard techniques. Preferred peptide modulating agents for use within such methods include those comprising one or more of the sequences INPISGQ (SEQ ID NO:22), LNPISGQ (SEQ ID NO:23), IDPVSGQ (SEQ ID NO:24), KIDPVNGQ (SEQ ID NO:25), PISGQ (SEQ ID NO:26), KIDPVN (SEQ ID NO:50), PVNGQ (SEQ ID NO:51), PISGQ (SEQ ID NO:52), PVSGR (SEQ ID NO:53), KIDPV (SEQ ID NO:54), KIDPVN (SEQ ID NO:55), IDPVN (SEQ ID NO:56), INPIS (SEQ ID NO:57), CPVNGQC (SEQ ID NO:58), CPISGQC (SEQ ID NO:59), CPVSGRC (SEQ ID NO:60), CKIDPVNC (SEQ ID NO:61), CIDPVNC (SEQ ID NO:62), CINPISC (SEQ ID NO:63) or CKIDPVC (SEQ ID NO:85), in which cyclization is indicated by an underline. Modulating agents may alternatively, or in addition, comprise a derivative of one of the foregoing sequences. Modulating agents comprising one or more of these sequences or derivatives thereof are also preferred. Preferred antibody modulating agents include Fab fragments directed against an N-cadherin HAV-BM sequence (e.g, INPISGQ (SEQ ID NO:22)). Such antibodies and fragments can be prepared using standard techniques, as discussed above. Suitable amounts of modulating agent generally range as described above, preferably from about 10 µg/mL to about 1 mg/mL.

Alternatively, a modulating agent may be administered alone or within a pharmaceutical composition. The duration and frequency of administration will be determined by such factors as the condition of the patient, and the type and severity of the patient's disease. Within particularly preferred embodiments of the invention, the modulating agent or pharmaceutical composition may be administered at a dosage ranging from 0.1 mg/kg to 20 mg/kg although appropriate dosages may be determined by clinical trials. Methods of administration include injection, intravenous or intrathecal (i.e., directly in cerebrospinal fluid). A modulating agent or pharmaceutical composition may further comprise a drug (e.g., an immunomodulatory drug).

Effective treatment of multiple sclerosis may be evidenced by any of the following criteria: EDSS (extended disability status scale), appearance of exacerbations or MRI (magnetic resonance imaging). The EDSS is a means to grade clinical impairment due to MS (Kurtzke, *Neurology* 33:1444, 1983), and a decrease of one fill step defines an effective treatment in the context of the present invention (Kurtzke, *Ann. Neurol* 36:573–79, 1994). Exacerbations are defined as the appearance of a new symptom that is attributable to MS and accompanied by an appropriate new neurologic abnormality (Sipe et al., *Neurology* 34:1368, 1984). Therapy is deemed to be effective if there is a statistically significant difference in the rate or proportion of exacerbation-free patients between the treated group and the placebo group or a statistically significant difference in the time to first exacerbation or duration and severity in the treated group compared to control group. MRI can be used to measure active lesions using gadolinium-DTPA-enhanced imaging (McDonald et al. *Ann. Neurol.* 36:14, 1994) or the location and extent of lesions using $T_2$-weighted techniques. The presence, location and extent of MS lesions may be determined by radiologists using standard techniques. Improvement due to therapy is established when there is a statistically significant improvement in an individual patient compared to baseline or in a treated group versus a placebo group.

Efficacy of the modulating agent in the context of prevention may be judged based on clinical measurements such as the relapse rate and EDSS. Other criteria include a change in area and volume of T2 images on MRI, and the number and volume of lesions determined by gadolinium enhanced images.

Within further aspects, modulating agents as described herein may be used for modulating the immune system of a mammal in any of several ways. Cadherins are expressed on immature B and T cells (thymocytes and bone marrow pre-B cells), as well as on specific subsets of activated B and T lymphocytes and some hematological malignancies (see Lee et al., *J. Immunol.* 152:5653–5659, 1994; Munro et al., *Cellular Immunol.* 169:309–312, 1996; Tsutsui et al., *J. Biochem.* 120:1034–1039, 1996; Cepek et al., *Proc. Natl. Acad. Sci. USA* 93:6567–6571, 1996). Modulating agents may generally be used to modulate specific steps within cellular interactions during an immune response or during the dissemination of malignant lymphocytes.

For example, a modulating agent as described herein may be used to treat diseases associated with excessive generation of otherwise normal T cells. Without wishing to be bound by any particular theory, it is believed that the interaction of cadherins on maturing T cells and B cell subsets contributes to protection of these cells from programmed cell death. A modulating agent may decrease such interactions, leading to the induction of programmed cell death. Accordingly, modulating agents may be used to treat certain types of diabetes and rheumatoid arthritis, particularly in young children where the cadherin expression on thymic pre-Tcells is greatest.

Modulating agents may also be administered to patients afflicted with certain skin disorders (such as cutaneous lymphomas), acute B cell leukemia and excessive immune reactions involving the humoral immune system and generation of immunoglobulins, such as allergic responses and antibody-mediated graft rejection. In addition, patients with circulating cadherin-positive malignant cells (e.g., during regimes where chemotherapy or radiation therapy is eliminating a major portion of the malignant cells in bone marrow and other lymphoid tissue) may benefit from treatment with a modulating agent. Such treatment may also benefit patients undergoing transplantation with peripheral blood stem cells.

Preferred modulating agents for use within such methods include those that disrupt E-cadherin and/or N-cadherin mediated cell adhesion, such as those comprising one or more of the sequences INPISGQ (SEQ ID NO:22), LNPISGQ (SEQ ID NO:23), IDPVSGQ (SEQ ID NO:24), KIDPVNGQ (SEQ ID NO:25), PISGQ (SEQ ID NO:26), KIDPVN (SEQ ID NO:50), PVNGQ (SEQ ID NO:51), PISGQ (SEQ ID NO:52), PVSGR (SEQ ID NO:53), KIDPV (SEQ ID NO:54), KIDPVN (SEQ ID NO:55), IDPVN (SEQ ID NO:56), INPIS (SEQ ID NO:57), CPVNGQC (SEQ ID NO:58), CPISGQC (SEQ ID NO:59), CPVSGRC (SEQ ID NO:60), CKIDPVNC (SEQ ID NO:61), CIDPVNC (SEQ ID NO:62), CINPISC (SEQ ID NO:63) or CKIDPVC (SEQ ID NO:85), in which cyclization is indicated by an underline. Modulating agents may alternatively, or in addition, comprise a derivative of one of the foregoing sequences. In addition, a preferred modulating agent may comprise one or more additional CAR sequences, such as HAV, RGD and/or KYSFNYDGSE (SEQ ID NO:67). As noted above, such additional sequence(s) may be separated from the HAV-BM sequence via a linker. Alternatively, a separate modulator of integrin-mediated cell adhesion may be administered in conjunction with the modulating agent(s), either within the same pharmaceutical composition or separately.

Within the above methods, the modulating agent(s) are preferably administered systemically (usually by injection) or topically. A modulating agent may be linked to a targeting agent. For example, targeting to the bone marrow may be beneficial. A suitable dosage is sufficient to effect a statistically significant reduction in the population of B and/or T cells that express cadherin and/or an improvement in the clinical manifestation of the disease being treated. Typical dosages generally range as described above.

Within further aspects, the present invention provides methods and kits for preventing pregnancy in a mammal. In general, disruption of E-cadherin function prevents the adhesion of trophoblasts and their subsequent fusion to form syncitiotrophoblasts. In one embodiment, one or more modulating agents as described herein may be incorporated into any of a variety of well known contraceptive devices, such as sponges suitable for intravaginal insertion (see, e.g., U.S. Pat. No. 5,417,224) or capsules for subdermal implantation. Other modes of administration are possible, however, including transdermal administration, for modulating agents linked to an appropriate targeting agent. Preferred modulating agents for use within such methods include those comprising one or more of the sequences INPISGQ (SEQ ID NO:22), LNPISGQ (SEQ ID NO:23), IDPVSGQ (SEQ ID NO:24), KIDPVNGQ (SEQ ID NO:25), PISGQ (SEQ ID NO:26), KIDPVN (SEQ ID NO:50), PVNGQ (SEQ ID NO:51), PISGQ (SEQ ID NO:52), PVSGR (SEQ ID NO:53), KIDPV (SEQ ID NO:54), KIDPVN (SEQ ID NO:55), IDPVN (SEQ ID NO:56), INPIS (SEQ ID NO:57), CPVNGQC (SEQ ID NO:58), CPISGQC (SEQ ID NO:59), CPVSGRC (SEQ ID NO:60), CKIDPVNC (SEQ ID NO:61), CIDPVNC (SEQ ID NO:62), CINPISC (SEQ ID NO:63) or CKIDPVC (SEQ ID NO:85), in which cyclization is indicated by an underline. Modulating agents may alternatively, or in addition, comprise a derivative of one of the foregoing sequences. In addition, a preferred modulating agent may comprise additional CAR sequences, such as HAV, DKK and/or RGD. As noted above, such additional sequences may be separated from the HAV-BM sequence via a linker. Alternatively, a separate modulator of integrin-mediated cell adhesion may be administered in conjunction with the modulating agent(s), either within the same pharmaceutical composition or separately.

Suitable methods for incorporation into a contraceptive device depend upon the type of device and are well known in the art. Such devices facilitate administration of the modulating agent(s) to the uterine region and may provide a sustained release of the modulating agent(s). In general, modulating agent(s) may be administered via such a contraceptive device at a dosage ranging from 0.1 to 50 mg/kg, although appropriate dosages may be determined by monitoring hCG levels in the urine. hCG is produced by the placenta, and levels of this hormone rise in the urine of pregnant women. The urine hCG levels can be assessed by radio-immunoassay using well known techniques. Kits for preventing pregnancy generally comprise a contraceptive device impregnated with one or more modulating agents.

Alternatively, a sustained release formulation of one or more modulating agents may be implanted, typically subdermally, in a mammal for the prevention of pregnancy. Such implantation may be performed using well known techniques. Preferably, the implanted formulation provides a dosage as described above, although the minimum effective dosage may be determined by those of ordinary skill in the art using, for example, an evaluation of hCG levels in the urine of women.

The present invention also provides methods for increasing vasopermeability in a mammal by administering one or more modulating agents or pharmaceutical compositions. Within blood vessels, endothelial cell adhesion (mediated by N-cadherin) results in decreased vascular permeability. Accordingly, modulating agents as described herein that decrease N-cadherin mediated adhesion may be used to increase vascular permeability. Particularly preferred modulating agents include those comprising one or more of the sequences INPISGQ (SEQ ID NO:22), LNPISGQ (SEQ ID NO:23), IDPVSGQ (SEQ ID NO:24), KIDPVNGQ (SEQ ID NO:25), PISGQ (SEQ ID NO:26), KIDPVN (SEQ ID NO:50), PVNGQ (SEQ ID NO:51), PISGQ (SEQ ID NO:52), PVSGR (SEQ ID NO:53), KIDPV (SEQ ID NO:54), KIDPVN (SEQ ID NO:55), IDPVN (SEQ ID NO:56), INPIS (SEQ ID NO:57), CPVNGQC (SEQ ID NO:58), CPISGQC (SEQ ID NO:59), CPVSGRC (SEQ ID NO:60), CKIDPVNC (SEQ ID NO:61), CIDPVNC (SEQ ID NO:62), CINPISC (SEQ ID NO:63) or CKIDPVC (SEQ ID NO:85), in which cyclization is indicated by an underline. Modulating agents may alternatively, or in addition, comprise a derivative of one of the foregoing sequences. In addition, a preferred modulating agent may comprise an occludin CAR sequence LYHY (SEQ ID NO:70) and/or an OB-cadherin CAR sequence DKK. As noted above, such an additional sequence may be separated from the HAV sequence via a linker. Alternatively, a separate modulator of occludin mediated cell adhesion may be administered in conjunction with one or modulating agents, either within the same pharmaceutical composition or separately.

Within certain embodiments, preferred modulating agents for use within such methods include peptides capable of decreasing both endothelial and tumor cell adhesion. Such modulating agents may be used to facilitate the penetration of anti-tumor therapeutic or diagnostic agents (e.g., monoclonal antibodies) through endothelial cell permeability barriers and tumor barriers. For example, a modulating agent may further comprise an E-cadherin HAV or HAV-BM sequence. Alternatively, separate modulating agents capable of disrupting N- and E-cadherin mediated adhesion may be administered concurrently.

In one particularly preferred embodiment, a modulating agent is further capable of disrupting cell adhesion mediated by multiple adhesion molecules. Such an agent may comprise an HAV-BM sequence, as well as an RGD sequence, the Dsc CAR sequences YAT, FAT and YAS, the Dsg CAR sequence RAL and/or the occludin CAR sequence LYHY (SEQ ID NO:70). Alternatively, a separate modulator cell adhesion that comprises a CAR sequence other than an HAV-BM sequence may be administered in conjunction with the modulating agent(s), either within the same pharmaceutical composition or separately.

Treatment with a modulating agent may be appropriate, for example, prior to administration of an anti-tumor therapeutic or diagnostic agent (e.g., a monoclonal antibody or other macromolecule), an antimicrobial agent or an anti-inflammatory agent, in order to increase the concentration of such agents in the vicinity of the target tumor, organism or inflammation without increasing the overall dose to the patient. Modulating agents for use within such methods may be linked to a targeting agent to further increase the local concentration of modulating agent, although systemic administration of a vasoactive agent even in the absence of a targeting agent increases the perfusion of certain tumors relative to other tissues. Suitable targeting agents include antibodies and other molecules that specifically bind to tumor cells or to components of structurally abnormal blood vessels. For example, a targeting agent may be an antibody that binds to a fibrin degradation product or a cell enzyme such as a peroxidase that is released by granulocytes or other cells in necrotic or inflamed tissues.

Administration via intravenous injection or transdermal administration is generally preferred. Effective dosages are generally sufficient to increase localization of a subsequently administered diagnostic or therapeutic agent to an extent that improves the clinical efficacy of therapy of accuracy of diagnosis to a statistically significant degree. Comparison may be made between treated and untreated tumor host animals to whom equivalent doses of the diagnostic or therapeutic agent are administered. In general, dosages range as described above.

Within a further aspect, modulating agents as described herein may be used for controlled inhibition of synaptic stability, resulting in increased synaptic plasticity. Within this aspect, administration of one or more modulating agents may be advantageous for repair processes within the brain, as well as learning and memory, in which neural plasticity is a key early event in the remodeling of synapses. Cell adhesion molecules, particularly N-cadherin and E-cadherin, can function to stabilize synapses, and loss of this function is thought to be the initial step in the remodeling of the synapse that is associated with learning and memory (Doherty et al., *J. Neurobiology,* 26:437–446, 1995; Martin and Kandel, *Neuron,* 17:567–570, 1996; Fannon and Colman, *Neuron,* 17:423–434, 1996). Inhibition of cadherin function by administration of one or more modulating agents that inhibit cadherin function may stimulate learning and memory. Preferred modulating agents for use within such methods include those that disrupt E-cadherin and/or N-cadherin mediated cell adhesion, such as those comprising one or more of the sequences INPISGQ (SEQ ID NO:22), LNPISGQ (SEQ ID NO:23), IDPVSGQ (SEQ ID NO:24), KIDPVNGQ (SEQ ID NO:25), PISGQ (SEQ ID NO:26), KIDPVN (SEQ ID NO:50), PVNGQ (SEQ ID NO:51), PISGQ (SEQ ID NO:52), PVSGR (SEQ ID NO:53), KIDPV (SEQ ID NO:54), KIDPVN (SEQ ID NO:55), IDPVN (SEQ ID NO:56), INPIS (SEQ ID NO:57), CPVNGQC (SEQ ID NO:58), CPISGQC (SEQ ID NO:59), CPVSGRC (SEQ ID NO:60), CKIDPVNC (SEQ ID NO:61), CIDPVNC (SEQ ID NO:62), CINPISC (SEQ ID NO:63) or CKIDPVC (SEQ ID NO:85), in which cyclization is indicated by an underline. Modulating agents may alternatively, or in addition, comprise a derivative of one of the foregoing sequences. In addition, a preferred modulating agent may comprise one or more additional CAR sequences, such as the sequence RGD, which is bound by integrins and/or the N-CAM CAR sequence KYSFNYDGSE (SEQ ID NO:67). As noted above, such additional sequence(s) may be separated from the HAV-BM sequence via a linker.

Alternatively, a separate modulator of integrin and/or N-CAM mediated cell adhesion may be administered in conjunction with the modulating agent(s), either within the same pharmaceutical composition or separately. For such aspects, administration may be via encapsulation into a delivery vehicle such as a liposome, using standard techniques, and injection into, for example, the carotid artery. Alternatively, a modulating agent may be linked to a disrupter of the blood-brain barrier. In general dosages range as described above.

ASSAYS EMPLOYING ANTI-HAV-BM ANTIBODIES

Other aspects of the present invention provide methods that employ antibodies raised against an HAV-BM sequence for diagnostic and assay purposes. Such polyclonal and monoclonal antibodies may be raised against a peptide using conventional techniques and as described above. Assays employing antibodies typically involve using an antibody to detect the presence or absence of a cadherin (free or on the surface of a cell), or proteolytic fragment containing the EC1 or EC4 domain in a suitable biological sample, such as tumor or normal tissue biopsies, blood, lymph node, serum or urine samples, or other tissue, homogenate, or extract thereof obtained from a patient.

There are a variety of assay formats known to those of ordinary skill in the art for using an antibody to detect a target molecule in a sample. See, e.g., Harlow and Lane, *Antibodies: A Laboratory Manual*, Cold Spring Harbor Laboratory, 1988. For example, the assay may be performed in a Western blot format, wherein a protein preparation from the biological sample is submitted to gel electrophoresis, transferred to a suitable membrane and allowed to react with the antibody. The presence of the antibody on the membrane may then be detected using a suitable detection reagent, as described below.

In another embodiment, the assay involves the use of antibody immobilized on a solid support to bind to the target cadherin, or a proteolytic fragment containing the EC1 or EC4 domain and encompassing the CAR sequence, and remove it from the remainder of the sample. The bound cadherin may then be detected using a second antibody or reagent that contains a reporter group. Alternatively, a competitive assay may be utilized, in which a cadherin is labeled with a reporter group and allowed to bind to the immobilized antibody after incubation of the antibody with the sample. The extent to which components of the sample inhibit the binding of the labeled cadherin to the antibody is indicative of the reactivity of the sample with the immobilized antibody, and as a result, indicative of the level of the cadherin in the sample.

The solid support may be any material known to those of ordinary skill in the art to which the antibody may be attached, such as a test well in a microtiter plate, a nitrocellulose filter or another suitable membrane. Alternatively, the support may be a bead or disc, such as glass, fiberglass, latex or a plastic such as polystyrene or polyvinylchloride. The antibody may be immobilized on the solid support using a variety of techniques known to those in the art, which are amply described in the patent and scientific literature.

In certain embodiments, the assay for detection of a cadherin in a sample is a two-antibody sandwich assay. This assay may be performed by first contacting an antibody that has been immobilized on a solid support, commonly the well of a microtiter plate, with the biological sample, such that the cadherin within the sample is allowed to bind to the immobilized antibody (a 30 minute incubation time at room temperature is generally sufficient). Unbound sample is then removed from the immobilized cadherin-antibody complexes and a second antibody (containing a reporter group such as an enzyme, dye, radionuclide, luminescent group, fluorescent group or biotin) capable of binding to a different site on the cadherin is added. The amount of second antibody that remains bound to the solid support is then determined using a method appropriate for the specific reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products. Standards and standard additions may be used to determine the level of cadherin in a sample, using well known techniques.

The present invention also provides kits for use in such immunoassays. Such kits generally comprise one or more antibodies, as described above. In addition, one or more additional compartments or containers of a kit generally enclose elements, such as reagents, buffers and/or wash solutions, to be used in the immunoassay.

Within further aspects, modulating agents or antibodies (or fragments thereof) may be used to facilitate cell identification and sorting in vitro or imaging in vivo, permitting the selection of cells expressing different cadherins (or different cadherin levels). Preferably, the modulating agent (s) or antibodies for use in such methods are linked to a detectable marker. Suitable markers are well known in the art and include radionuclides, luminescent groups, fluorescent groups, enzymes, dyes, constant immunoglobulin domains and biotin. Within one preferred embodiment, a modulating agent linked to a fluorescent marker, such as fluorescein, is contacted with the cells, which are then analyzed by fluorescence activated cell sorting (FACS).

Antibodies or fragments thereof may also be used within screens of combinatorial or other nonpeptide-based libraries to identify other compounds capable of modulating cadherin-mediated cell adhesion. Such screens may generally be performed using an ELISA or other method well known to those of ordinary skill in the art that detect compounds with a shape and structure similar to that of the modulating agent. In general, such screens may involve contacting an expression library producing test compounds with an antibody, and detecting the level of antibody bound to the candidate compounds. Compounds for which the antibody has a higher affinity may be further characterized as described herein, to evaluate the ability to modulate cadherin-mediated cell adhesion.

IDENTIFICATION OF HAV-BM BINDING COMPOUNDS

The present invention further provides methods for identifying compounds that bind to an HAV-BM sequence. Such agents may generally be identified by contacting a polypeptide as provided herein with a candidate compound or agent under conditions and for a time sufficient to allow interaction with a polypeptide comprising an HAV-BM sequence. Any of a variety of well known binding assays may then be performed to assess the ability of the candidate compound to bind to the polypeptide. In general, a candidate compound that binds to the polypeptide at a significantly greater level than a similar polypeptide that does not contain an HAV-BM sequence, is considered a compound that binds to an HAV-BM sequence. Preferably, the candidate compound generates a signal within a binding assay that is at least three standard deviations above the level of signal detected for a polypeptide that does not contain an HAV-BM sequence. Depending on the design of the assay, a polypeptide comprising an HAV-BM sequence may be free in solution, affixed to a solid support, present on a cell surface or located within the cell. Large scale screens may be performed using automation.

Within certain embodiments, the polypeptide may be immobilized onto a solid support material, and used to affinity purify binding compounds from, for example, cell or tissue extracts. The solid support material may be any material known to those of ordinary skill in the art to which the polypeptide may be attached. For example, the solid support may be a test well in a microtiter plate or a nitrocellulose filter or other suitable membrane. Alternatively, the support may be a bead or disc, such as glass, fiberglass, latex or a plastic material such as polystyrene or polyvinylchloride. The polypeptide may be immobilized on the solid support using a variety of techniques known to those in the art, which are amply described in the patent and scientific literature. In the context of the present invention, the term "immobilization" refers to both noncovalent association, such as adsorption, and covalent attachment (which may be a direct linkage between the polypeptide and functional groups on the support or may be a linkage by way of a cross-linking agent). Adsorption may be achieved by contacting the polypeptide, in a suitable buffer, with the solid support for a suitable amount of time. The contact time varies with temperature, but is typically between about 1 hour and 1 day. Covalent attachment of polypeptide to a solid support may also generally be achieved by first reacting the support with a bifunctional reagent that will react with both the support and a functional group, such as a hydroxyl or amino group, on the polypeptide using well known techniques.

Alternatively, a polypeptide may be incubated with whole cells, and interacting proteins may then be cross-linked to the polypeptide using standard techniques. Such polypeptides may be labeled with a detectable marker (e.g., a radionuclide) or may be subsequently detected using a detection reagent (e.g., an antibody) that is linked to such a marker. Within other assays, cDNA expression libraries may be screened with a labeled polypeptide to identify polynucleotides encoding proteins that interact with the labeled polypeptide. Similarly, a yeast two-hybrid system may be employed to identify interacting proteins. Other assays may be performed in a Western blot format, wherein a protein preparation from a biological sample such as a cell or tissue extract is submitted to gel electrophoresis, transferred to a suitable membrane and allowed to react with the polypeptide. The presence of the polypeptide on the membrane may then be detected using a label linked to the polypeptide or to a suitable detection reagent, such as an antibody. All of the above assays are well known to those of ordinary skill in the art, and may be performed according to standard protocols. These assays are representative only, and it will be apparent that other assays designed to evaluate binding may also be employed.

Following identification of a compound that binds to an HAV-BM sequence (or a polynucleotide encoding such a compound), standard structural analyses may be performed. In general, a polynucleotide may be sequenced using well known techniques employing such enzymes as Klenow fragment of DNA polymerase I, Sequenase® (US Biochemical Corp., Cleveland Ohio) Taq polymerase (Perkin Elmer, Foster City Calif.) or thermostable T7 polymerase (Amersham, Chicago, Ill.). An automated sequencing system may be used, using instruments available from commercial suppliers such as Perkin Elmer and Pharmacia. Proteins may be partially sequenced using standard techniques, and the sequence information used to retrieve a cDNA molecule encoding the protein (e.g., using PCR or hybridization screens employing degenerate oligonucleotides).

The following examples are offered by way of illustration and not by way of limitation.

EXAMPLES

Example 1

Preparation of Representative Modulating Agents

This Example illustrates the solid phase synthesis of representative peptide modulating agents.

The peptides were synthesized on a 431A Applied Biosystems peptide synthesizer using p-Hydroxymethylphenoxymethyl polystyrene (HMP) resin and standard Fmoc chemistry. After synthesis and deprotection, the peptides were de-salted on a Sephadex G-10 column and lyophilized. The peptides were analyzed for purity by analytical HPLC, and in each case a single peak was observed. Peptides were made as stock solutions at 10 to 25 mg/mL in dimethylsulfoxide (DMSO) or water and stored at −20° C. before use.

Example 2

Disruption of the Ability of Mouse Cerebellar Neurons to Extend Neurites

N-cadherin and N-CAM are established as CAMs that can regulate neurite outgrowth (Doherty and Walsh, Curr. Op. Neurobiol. 4:49–55, 1994; Williams et al., Neuron 13:583–594, 1994; Hall et al., Cell Adhesion and Commun. 3:441–450, 1996; Doherty and Walsh, Mol. Cell. Neurosci. 8:99–111, 1996; Saffell et al., Neuron 18:231–242, 1997). Neurons cultured on monolayers of 3T3 cells that have been transfected with cDNAs encoding N-cadherin or N-CAM extend longer neurites than neurons cultured on the untransfected parental 3T3 cells (commonly referred to as the control 3T3 cells). It has been determined that the neurite response stimulated by transfected N-CAM and N-cadherin initially depends upon a trans homophilic binding interaction between the transfected CAM in the 3T3 cell and the corresponding CAM in the neuron. This Example illustrates the use of representative modulating agents to disrupt neurite outgrowth stimulated by N-cadherin.

Neurons were cultured on monolayers of 3T3 cells transfected with cDNA encoding N-cadherin essentially as described by Doherty and Walsh, Curr. Op. Neurobiol. 4:49–55, 1994; Williams et al., Neuron 13:583–594, 1994; Hall et al., Cell Adhesion and Commun. 3:441–450, 1996; Doherty and Walsh, Mol. Cell. Neurosci. 8:99–111, 1994; Safell et al., Neuron 18:231–242, 1997. Briefly, monolayers of control 3T3 fibroblasts and 3T3 fibroblasts that express N-cadherin were established by overnight culture of 80,000 cells in individual wells of an 8-chamber well tissue culture slide. 3000 cerebellar neurons isolated from post-natal day 3 mouse brains were cultured for 18 hours on the various monolayers in control media (SATO/2% FCS), or media supplemented with various concentrations of the test peptide to be evaluated. The cultures were then fixed and stained for GAP43 which specifically binds to the neurons and their neurites. The length of the longest neurite on each GAP43 positive neuron was then measured by computer assisted morphometry. For each data point, measurements were made from 100–160 neurons, and the given values show the mean +/− the standard error of the mean.

Figure 5:
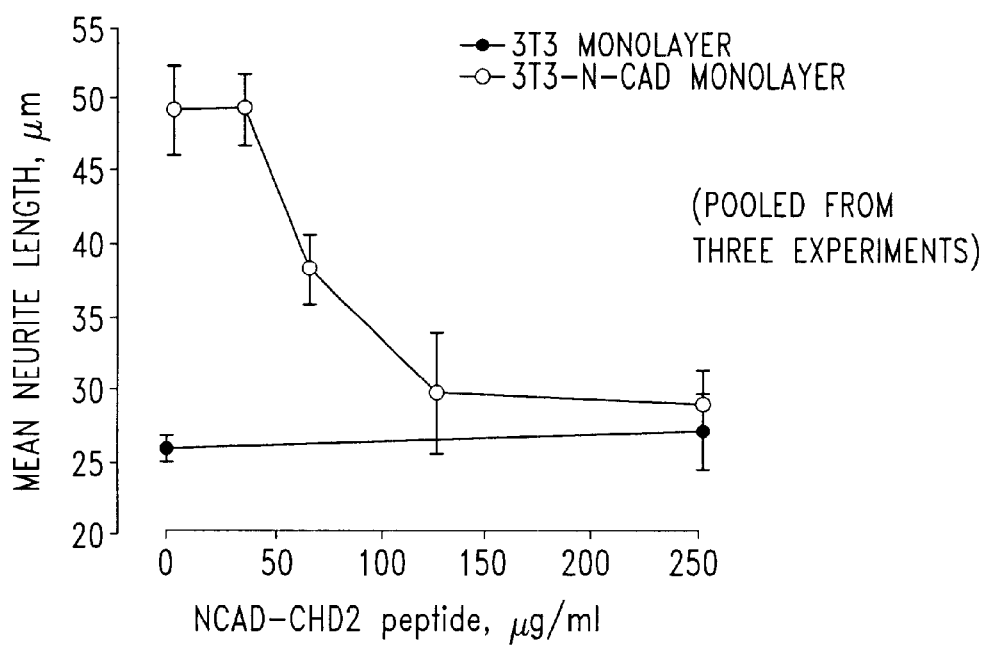
FIG. 5 is a graph showing the mean neurite length measured for neurons cultured on monolayers of 3T3 cells or 3T3 cells expressing N-cadherin in media containing varying concentrations of the linear peptide H-WLKIDPVNGQI-OH (SEQ ID NO:13; designated N-CAD-CHD2).

One modulating agent was H-WLKIDPVNGQI-OH (SEQ ID NO:13), an 11 amino acid peptide containing the ECD4 HAV-BM from human N-cadherin plus some flanking sequence. This peptide is designated N-CAD-CHD2. FIG. 5 shows the neurite outgrowth response for neurons cultured on monolayers of 3T3 cells or 3T3 cells expressing N-cadherin in media containing varying concentrations of the modulating agent. In the absence of the peptide, neurites were considerably longer on the N-cadherin monolayers. The peptide fully inhibited the N-cadherin response at a concentration of 125 and 250 µg/ml.

Figure 6:
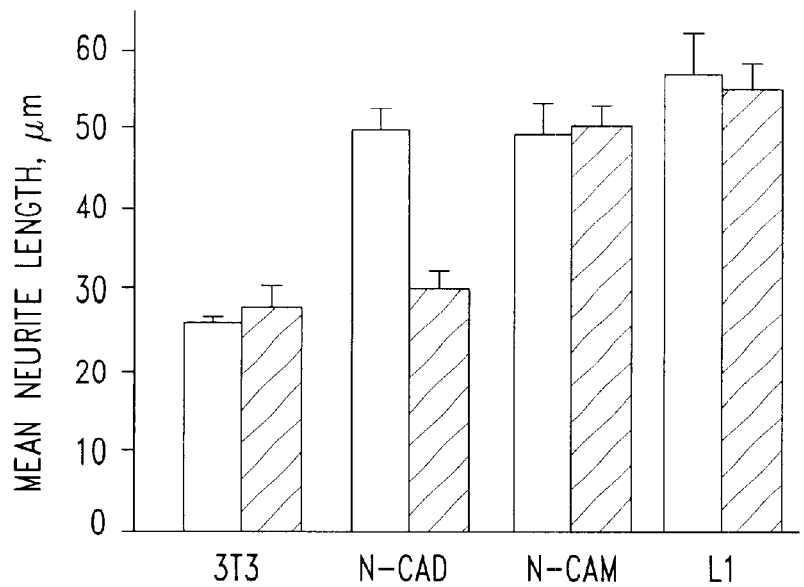
FIG. 6 is a graph showing the mean neurite length measured for neurons cultured on monolayers of either 3T3 cells, 3T3 cells expressing N-cadherin, 3T3 cells expressing NCAM, or 3T3 cells expressing L1 in media containing the linear peptide H-WLKIDPVNGQI-OH (SEQ ID NO:13; designated N-CAD-CHD2) at a concentration of 250 μg/ml.

The mean neurite length was further measured for neurons cultured on monolayers of 3T3 cells, 3T3 cells expressing N-cadherin, 3T3 cells expressing NCAM, and 3T3 cells expressing L1 in media containing the linear peptide H-WLKIDPVNGQI-OH (SEQ ID NO:13; designated N-CAD-CHD2) at a concentration of 250 µg/ml. The graph shown in FIG. 6 summarizes the results. Neurite outgrowth was approximately twice as long on 3T3 cells expressing either of the cell adhesion molecules N-cadherin, N-CAM, or L1, as compared to outgrowth on 3T3 cells in the absence of the peptide. Only neurite outgrowth on 3T3 cells expressing N-cadherin was inhibited by the peptide H-WLKIDPVNGQI-OH (SEQ ID NO:13). This peptide is therefore a specific inhibitor of N-cadherin function.

The ability of different modulating agents to inhibit neurite outgrowth was also evaluated. Table II shows the effects of the peptides N-Ac-INPISGQ-NH$_2$ (SEQ ID NO:22), H-INPISGQ-OH (SEQ ID NO:22), N-Ac-NLKIDPVNGQI-NH$_2$ (SEQ ID NO:20), H-WLKIDPVNGQI-OH (SEQ ID NO:13), H-LKIDPVNGQI-OH (SEQ ID NO:21), H-LKIDPANGQI-OH (SEQ ID NO:64) and H-LKIDAVNGQI-OH (SEQ ID NO:65) on neurite outgrowth. The peptides were tested at a concentration of 100 µg/ml. Rat neurons were grown for 20 hours on monolayers of either 3T3 cells, or 3T3 cells expressing N-cadherin. The cultures were then fixed, and the mean neurite length was determined by making measurements on at least 150 neurons for each treatment. The results are presented as the percentage inhibition of neurite outgrowth over 3T3 cells expressing N-cadherin. The peptides did not inhibit neurite outgrowth over 3T3 cells not expressing N-cadherin.

TABLE II

Effect of Representative Modulating Agents on Neurite Outgrowth on 3T3 Cells Expressing N-cadherin

| Treatment | Inhibition of Neurite Outgrowth (%) |
|---|---|
| no peptide (control) | 0% |
| N-Ac-INPISGQ-NH$_2$ (SEQ ID NO: 22) | 91% |
| H-INPISGQ-OH (SEQ ID NO: 22) | 35% |
| N-Ac-NLKIDPVNGQI-NH$_2$ (SEQ ID NO: 20) | 54% |
| H-WLKIDPVNGQI-OH (SEQ ID NO: 13) | 57% |
| H-LKIDPVNGQI-OH (SEQ ID NO: 21) | 31% |
| H-LKIDPANGQI-OH (SEQ ID NO: 64) | 45% |
| H-LKIDAVNGQI-OH (SEQ ID NO: 65) | 100% |

Table III shows the effects of various concentrations of peptide H-WLKIDPVNGQI-OH (SEQ ID NO:13) on mean neurite length of rat cerebellar neurons, isolated at post-natal day 2, and cultured on monolayers of 3T3 cells or 3T3 cells expressing N-cadherin, as described as above. The results are expressed as the percentage inhibition of neurite outgrowth over 3T3 cells expressing N-cadherin. The peptides did not inhibit neurite outgrowth over 3T3 cells not expressing N-cadherin.

TABLE III

Effect of Modulating Agent Concentration on Neurite Outgrowth on 3T3 Cells Expressing N-cadherin

| Concentration of H-WLKIDPVNGQI-OH (SEQ ID NO: 13) | Inhibition of Neurite Outgrowth (%) |
|---|---|
| 0 μg/ml | 0% |
| 33 μg/ml | 31% |
| 100 μg/ml | 57% |
| 250 μg/ml | 100% |

Table IV shows the effects of various concentrations of peptide H-NLKIDPVNGQI-OH (SEQ ID NO:20) on mean neurite length of rat cerebellar neurons, isolated at post-natal day 2, and cultured on monolayers of 3T3 cells or 3T3 cells expressing N-cadherin as described above. The results are expressed as the percentage inhibition of neurite outgrowth over 3T3 cells expressing N-cadherin. The peptides did not inhibit neurite outgrowth over 3T3 cells not expressing N-cadherin.

TABLE IV

Effect of Modulating Agent Concentration on Neurite Outgrowth on 3T3 Cells Expressing N-cadherin

| Concentration of H-NLKJDPVKGQI-OH (SEQ ID NO: 20) | Inhibition of Neurite Outgrowth (%) |
|---|---|
| 0 μg/ml | 0% |
| 33 μg/ml | 23% |
| 100 μg/ml | 54% |
| 250 μg/ml | 91% |

Table V shows the effects of various concentrations of peptide N-Ac-INPISGQ-NH2 (SEQ ID NO:22) on mean neurite length of rat cerebellar neurons, isolated at post-natal day 2, and cultured on monolayers of 3T3 cells or 3T3 cells expressing N-cadherin as described above. The results are expressed as the percentage inhibition of neurite outgrowth over 3T3 cells expressing N-cadherin. The peptides did not inhibit neurite outgrowth over 3T3 cells not expressing N-cadherin.

TABLE V

Effect of Modulating Agent Concentration on Neurite Outgrowth on 3T3 Cells Expressing N-cadherin

| Concentration of N-Ac-INPISGQ-NH2 (SEQ ID NO: 22) | Inhibition of Neurite Outgrowth (%) |
|---|---|
| 0 μg/ml | 0% |
| 11 μg/ml | 64% |
| 33 μg/ml | 91% |
| 100 μg/ml | 91% |
| 250 μg/ml | 100% |

Peptides N-Ac-INPISGQ-NH2 (SEQ ID NO:22), H-NKIDPVNGQI-OH (SEQ ID NO:20) and H-LKIDAVNGQI-OH (SEQ ID NO:21) were also tested for their ability to inhibit neurite outgrowth monolayers of 3T3 cells expressing the L1 adhesion molecule. The peptides did not inhibit the L1 response. These result demonstrate that modulating agents comprising an HAV-BM sequence are effective and specific inhibitors of N-cadherin function.

These results demonstrate that modulating agents comprising an HAV-BM sequence are effective and specific inhibitors of N-cadherin function.

Example 3

Modulating Agent Binding to N-Cadherin

This Example illustrates the ability of a representative modulating agent to bind to N-cadherin.

Figure 7:
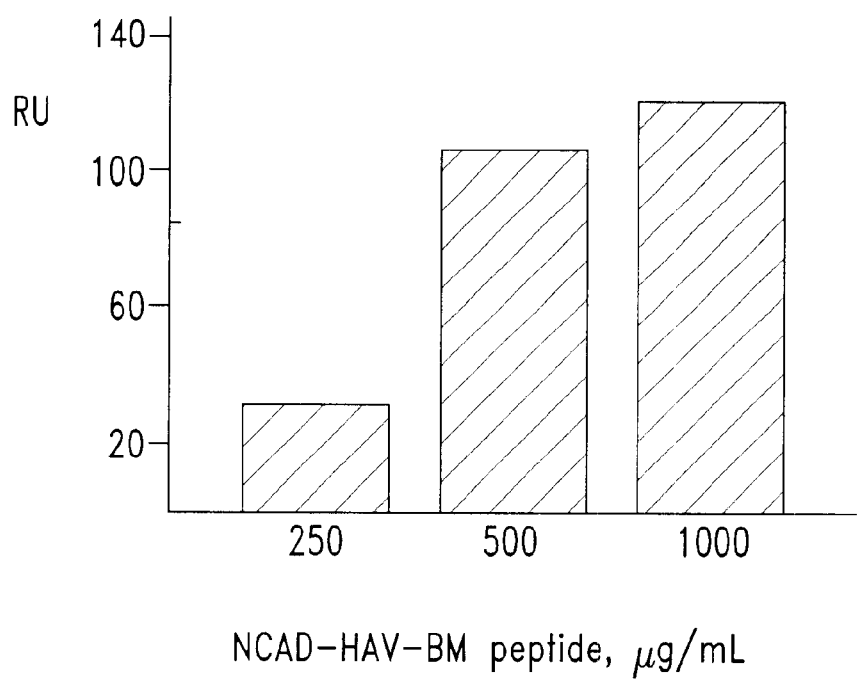
FIG. 7 is a graph illustrating the binding of the peptide H-WLKIDPVNGQI-OH (SEQ ID NO: 13) at various concentrations to a flow cell coated with an N-cadherin-Fc chimera or human IgG1. The peptide H-WLKIDPVNGQI-OH (SEQ ID NO: 13) was passed over both flow cells at a concentration of either 250, 500 or 1000 μg/ml. The results show the association of the peptide to the flow cell coated with the N-cadherin Fc chimera, with the binding to the control flow cell (coated with human IgG1) automatically subtracted.

The peptide H-WLKIDPVNGQI-OH (SEQ ID NO: 13) was passed over flow cells coated with an N-cadherin-Fc chimera or human IgG1 at a concentration of either 250, 500 or 1000 μg/ml. FIG. 7 is a graph illustrating the association of the peptide to the flow cell coated with the N-cadherin Fc chimera, with the binding to the control flow cell (coated with human IgG1) automatically subtracted.

Example 4

Effect of a Representative Modulating Agent on Tumor Cell Adhesion

This Example illustrates the ability of a modulating agent to disrupt tumor cell adhesion.

Figure 8A:
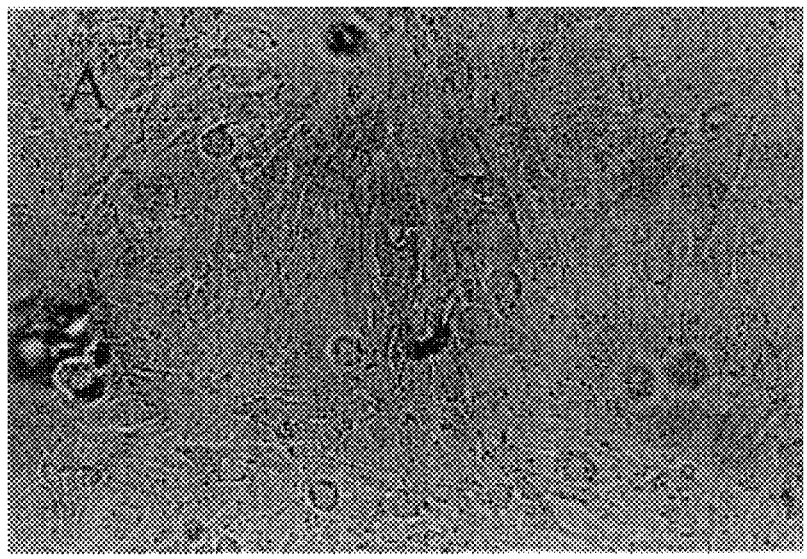
FIGS. 8A and 8B are photographs showing monolayer cultures of human ovarian cancer cells (SKOV3) in the presence (FIG. 8B) and absence (FIG. 8A) of the peptide N-Ac-INPISGQ-NH$_2$ (SEQ ID NO:22).
Figure 8B:
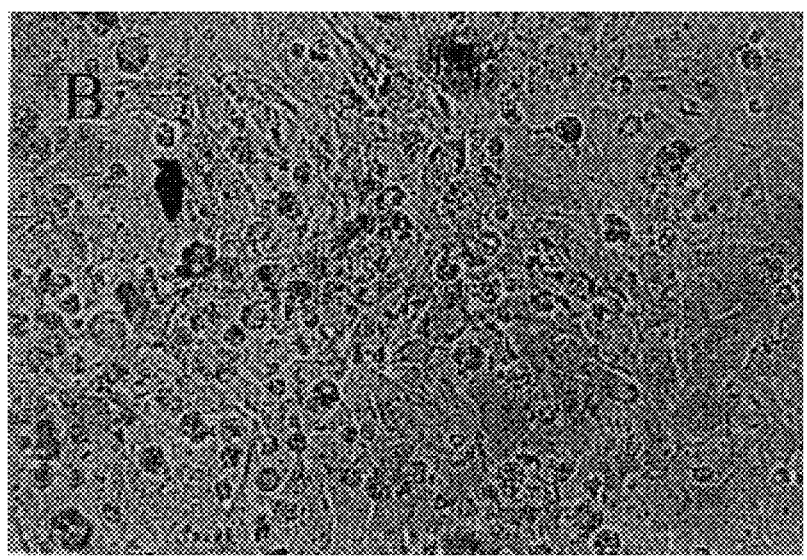

Monolayer cultures of human ovarian cancer cells (SKOV3) were grown in the presence and absence of the peptide N-Ac-INPlSGQ-NH$_2$ (SEQ ID NO:22). FIG. 8A shows the cells grown in the absence of peptide. FIG. 8B shows the cells 24 hours after being cultured in the presence of 1 mg/mL of N-Ac-INPISGQ (SEQ ID NO:22). The SKOV3 cells retract from one another and round-up when cultured in the presence of the peptide.

From the foregoing, it will be evident that although specific embodiments of the invention have been described herein for the purpose of illustrating the invention, various modifications may be made without deviating from the spirit and scope of the invention.

What is claimed is:

1. A cell adhesion modulating agent, wherein the agent comprises an HAV-BM sequence that is SEQ ID NO:22 present within a peptide ranging in size from 6 to 16 amino acid residues.

2. A modulating agent according to claim 1, wherein the HAV-BM sequence is present within a peptide comprising an N-terminal or C-terminal modification.

3. A modulating agent according to claim 1 linked to a solid support.

4. A modulating agent according to claim 3, wherein the solid support is a polymeric matrix.

5. A modulating agent according to claim 4, wherein the solid support is selected from the group consisting of plastic dishes, plastic tubes, sutures, membranes, ultra thin films, bioreactors and microparticles.

6. A modulating agent according to claim 1, further comprising:

a cell adhesion recognition sequence other than an HAV-BM sequence, wherein the cell adhesion recognition sequence is separated from any HAV-BM sequence(s) by a linker, and wherein said cell adhesion recognition sequence is selected from the group consisting of cadherins, integrins, occludin, N-CAM, desmogleins, desmocollins, fibronectin and laminin.

7. A modulating agent according to claim 1 linked to a detectable marker.

8. A modulating agent according to claim 1 linked to a targeting agent.

9. A pharmaceutical composition comprising a cell adhesion modulating agent according to claim 1, in combination with a pharmaceutically acceptable carrier.

10. A composition according to claim 9, wherein the cell adhesion modulating agent is present within a sustained-release formulation.

11. A pharmaceutical composition according to claim 9, further comprising a modulator of cell adhesion, wherein the modulator comprises:

a peptide comprising a cell adhesion recognition sequence other than an HAV-BM sequence, and wherein said cell adhesion recognition sequence is selected from the group consisting of cadherins, integrins, occludin, N-CAM, desmogleins, fibronectin and laminin.

* * * * *

UNITED STATES PATENT AND TRADEMARK OFFICE
CERTIFICATE OF CORRECTION

PATENT NO. : 6,277,824 B1
DATED : August 21, 2001
INVENTOR(S) : Patrick Doherty et al.

It is certified that error appears in the above-identified patent and that said Letters Patent is hereby corrected as shown below:

<u>Column 101,</u>
Line 34, "linker, and wherein said cell" should read -- linker, wherein said cell --.

<u>Column 102,</u>
Line 33, "N-CAM, desmogleins, fibronectin" should read -- N-CAM, desmogleins, desmocollins, fibronectin --.

Signed and Sealed this

Thirteenth Day of January, 2004

JON W. DUDAS
*Acting Director of the United States Patent and Trademark Office*